(12) United States Patent
Nagaoka

(10) Patent No.: US 8,852,904 B2
(45) Date of Patent: Oct. 7, 2014

(54) PROTEIN COMPLEX HAVING ACTIVITY CATALYZING ASYMMETRIC OXIDATION REACTION AND PROCESS FOR PRODUCING THE SAME

(75) Inventor: Hiroyuki Nagaoka, Maebashi (JP)

(73) Assignee: Sanyo Foods Co., Ltd., Tokyo (JP)

(*) Notice: Subject to any disclaimer, the term of this patent is extended or adjusted under 35 U.S.C. 154(b) by 0 days.

(21) Appl. No.: 13/321,520

(22) PCT Filed: May 20, 2010

(86) PCT No.: PCT/JP2010/058945
§ 371 (c)(1),
(2), (4) Date: Nov. 18, 2011

(87) PCT Pub. No.: WO2010/134642
PCT Pub. Date: Nov. 25, 2010

(65) Prior Publication Data
US 2012/0064588 A1    Mar. 15, 2012

(30) Foreign Application Priority Data
May 22, 2009   (JP) .................................. 2009-124645

(51) Int. Cl.
*C12P 7/02* (2006.01)
*A61L 33/00* (2006.01)
*C12P 7/26* (2006.01)
*C12N 11/04* (2006.01)
*C12P 41/00* (2006.01)
*C12N 9/96* (2006.01)
*C12N 9/02* (2006.01)

(52) U.S. Cl.
CPC ... *C12P 7/02* (2013.01); *C12P 7/26* (2013.01); *C12N 11/04* (2013.01); *C12P 41/002* (2013.01); *C12N 9/96* (2013.01); *C12N 9/0004* (2013.01)
USPC ............................................. 435/155; 522/87

(58) Field of Classification Search
None
See application file for complete search history.

(56) References Cited

FOREIGN PATENT DOCUMENTS

| JP | 5-508549 | 12/1993 |
|---|---|---|
| JP | 2001-19650 | 1/2001 |
| WO | WO 92/02617 | 2/1992 |
| WO | WO/98/12228 | * 3/1998 |
| WO | WO 99/34010 | 7/1999 |
| WO | WO/2005/066341 | * 7/2005 |

OTHER PUBLICATIONS

Nagaoka, Chiral Resolution Function with Immobilized Food Proteins., Biotechnol. Prog. (2003), vol. 19, pp. 1149-1155.*

(Continued)

*Primary Examiner* — Alexander Kim
(74) *Attorney, Agent, or Firm* — Christie, Parker & Hale, LLP

(57) ABSTRACT

A process for producing a cross-linked crystallized protein complex, which comprises: a first step of concentrating a crude protein derived from an animal or plant; a second step of encapsulating the protein in a gel, to thereby allow the protein to undergo air oxidation, and then extracting a protein complex from the gel; a third step of allowing the extracted protein complex to undergo crystallization and precipitation; and a fourth step of cross-linking the precipitated protein complex. Alternatively, by use of a fifth step of drying (FD) the obtained crosslinked crystallized protein complex, to thereby form a powder. As a result, there is provided an enzyme which is stable at room temperature storage, and has an activity in catalyzing an asymmetric oxidation reaction. That is, there is provided a useful material which enables an efficient enzyme-mimetic reaction under a mild condition.

28 Claims, 25 Drawing Sheets

(56) References Cited

OTHER PUBLICATIONS

Nagaoka et al., Resolution and Synthesis of Optically Active Alcohols with Immobilized Ovalbumin and Pea Protein as New Bio-catalysts, Bioscience, Biotechnology, and Biochemistry (2001), vol. 65 No. 3, pp. 634-637.*

Nagaoka et al., Resolution and Synthesis of Optically Active Alcohols with Immobilized Water-soluble Proteins from Green Pea, Soybean and Buckwheat as New Bio-catalysts., Bioscience, Biotechnology, and Biochemistry (2000), vol. 64 No. 4, pp. 781-784.*

International Search Report, dated Sep. 7, 2010, corresponding to PCT/JP2010/058945, 8 pages.

Nagaoka, "Seibutsu Zairyo no Fusei Sanka Kangen Hanno o Shokubai sum Noryoku", Japan Society for Bioscience, Biotechnology, and Agrochemistry 2004 Nendo (Heisei 16 Nendo) Taikai Koen Yoshishu, 2004, p. 250, 3A27p02.

Inaba, et al., "Crystal Structure of the DsbB-DsbA Complex Reveals a Mechanism of Disulfide Bond Generation" Cell, vol. 127, pp. 789-801, Nov. 17, 2006.

Japanese Office action issued on Aug. 12, 2014 in corresponding JP Application No. 2013-013467, 3pp.

* cited by examiner

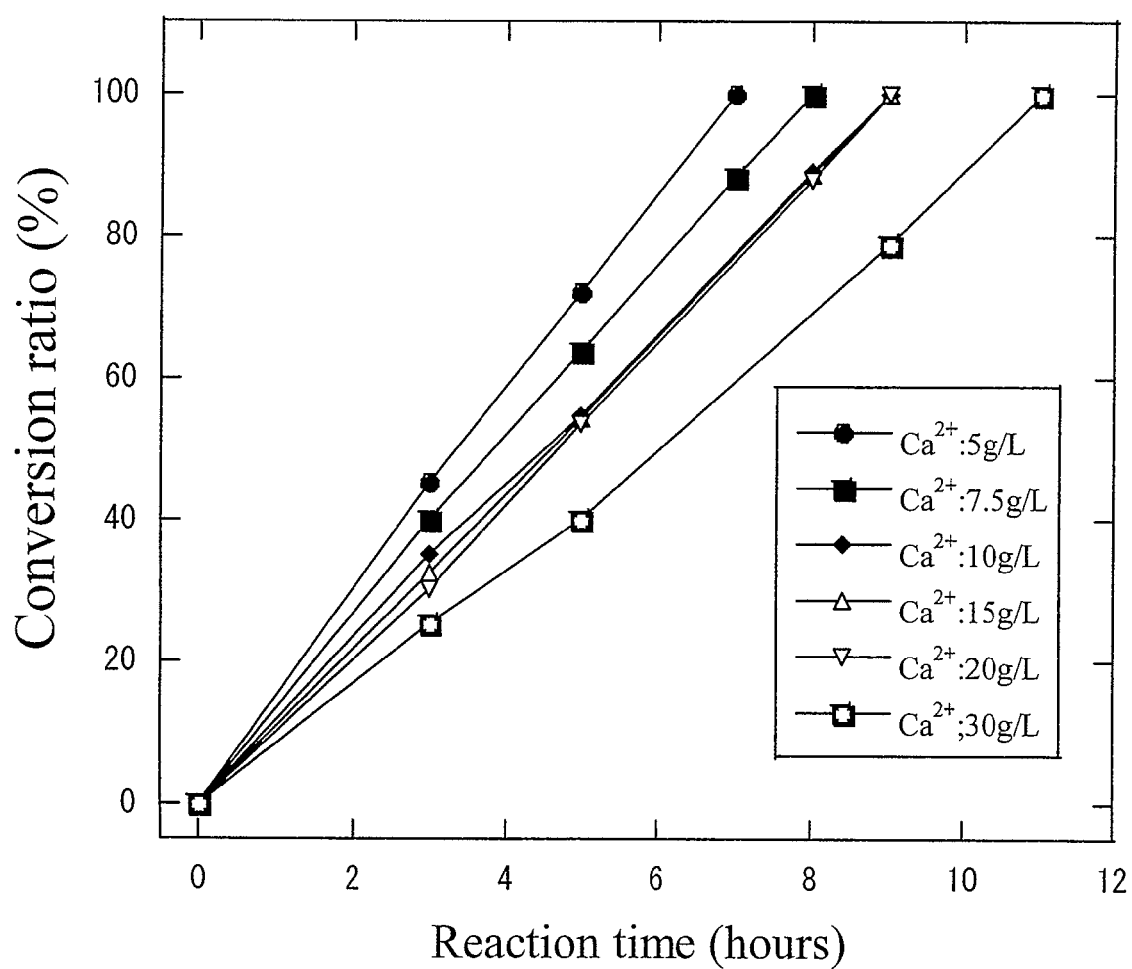

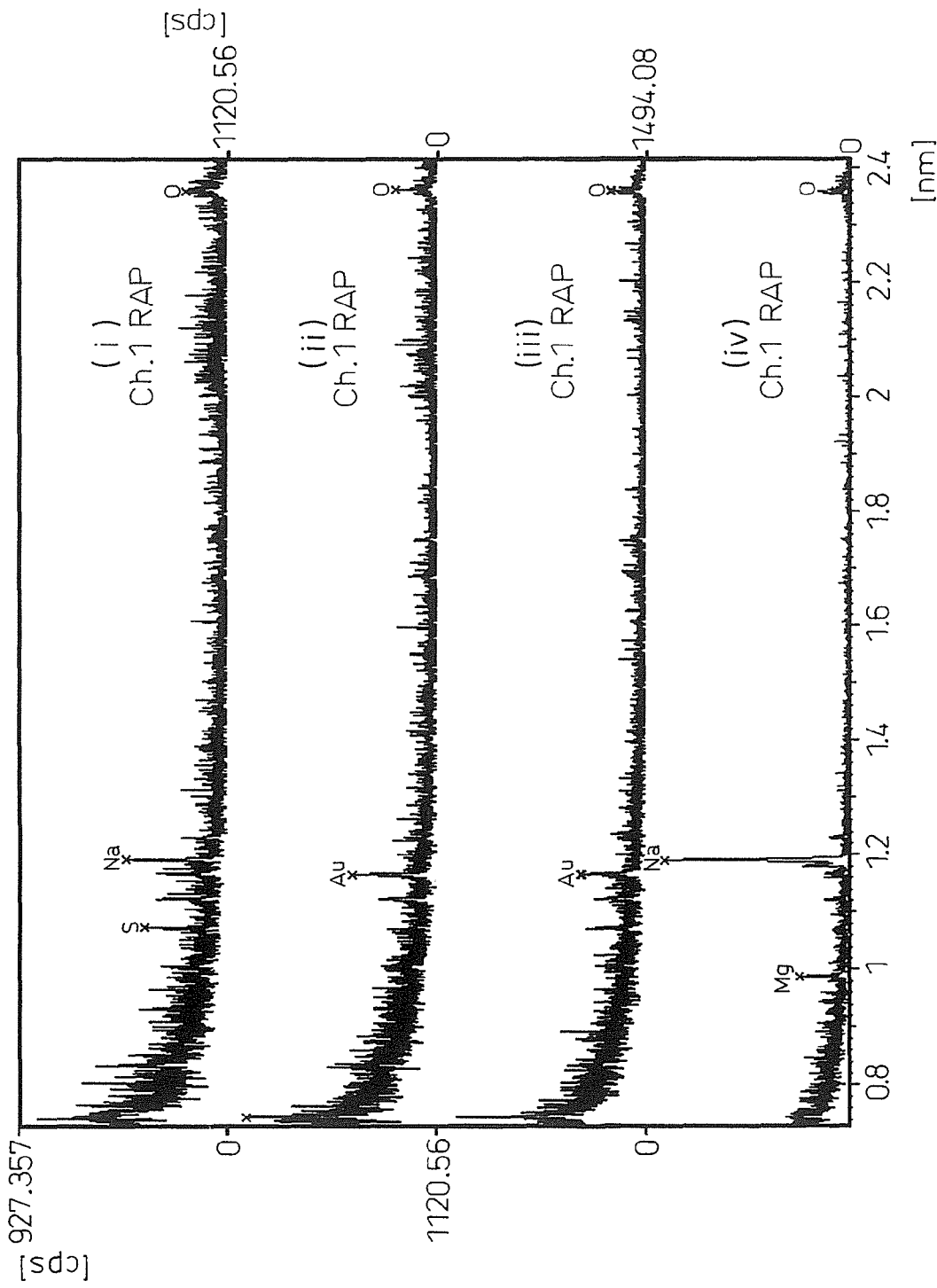

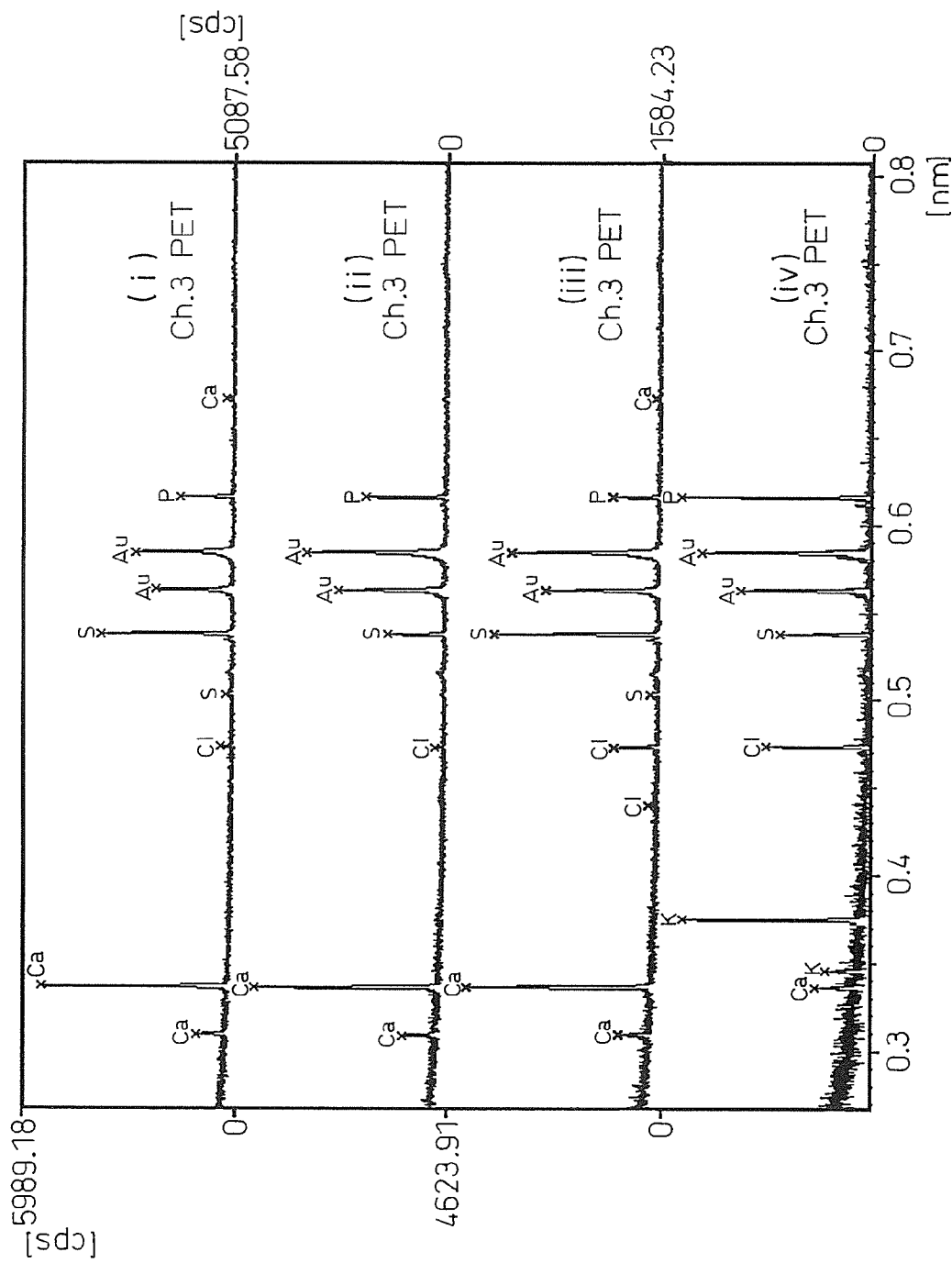

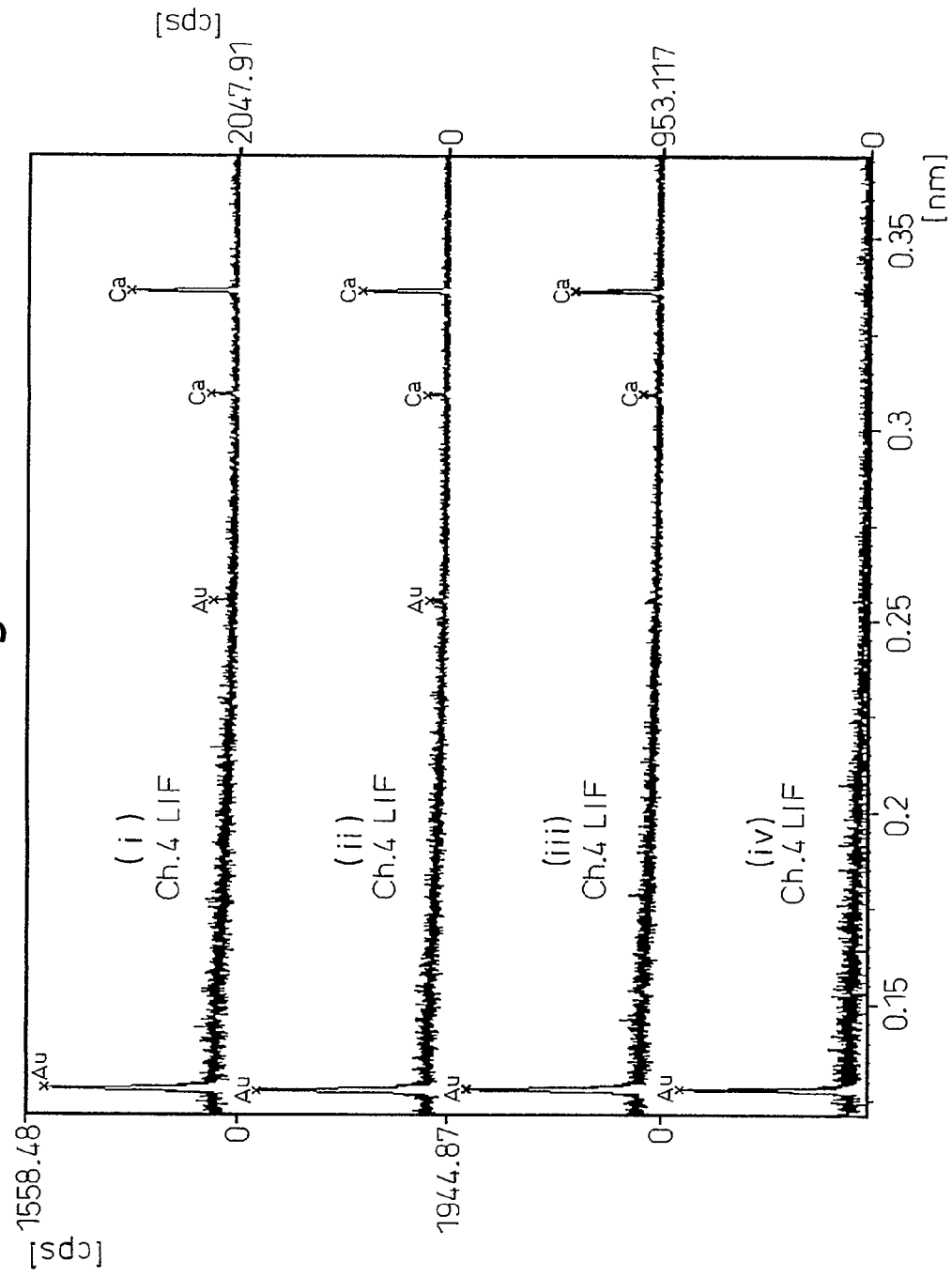

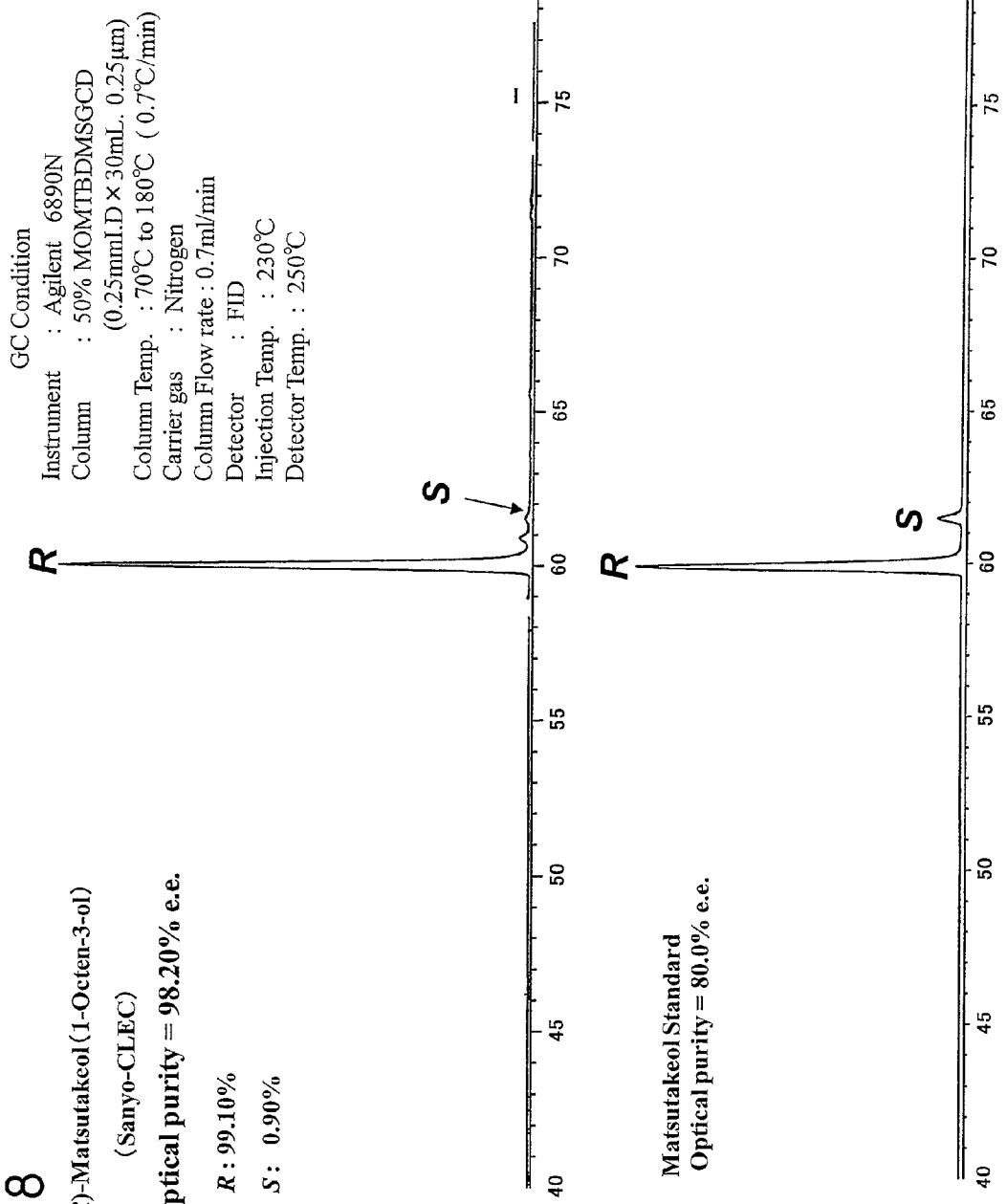

DO pH

DO pH

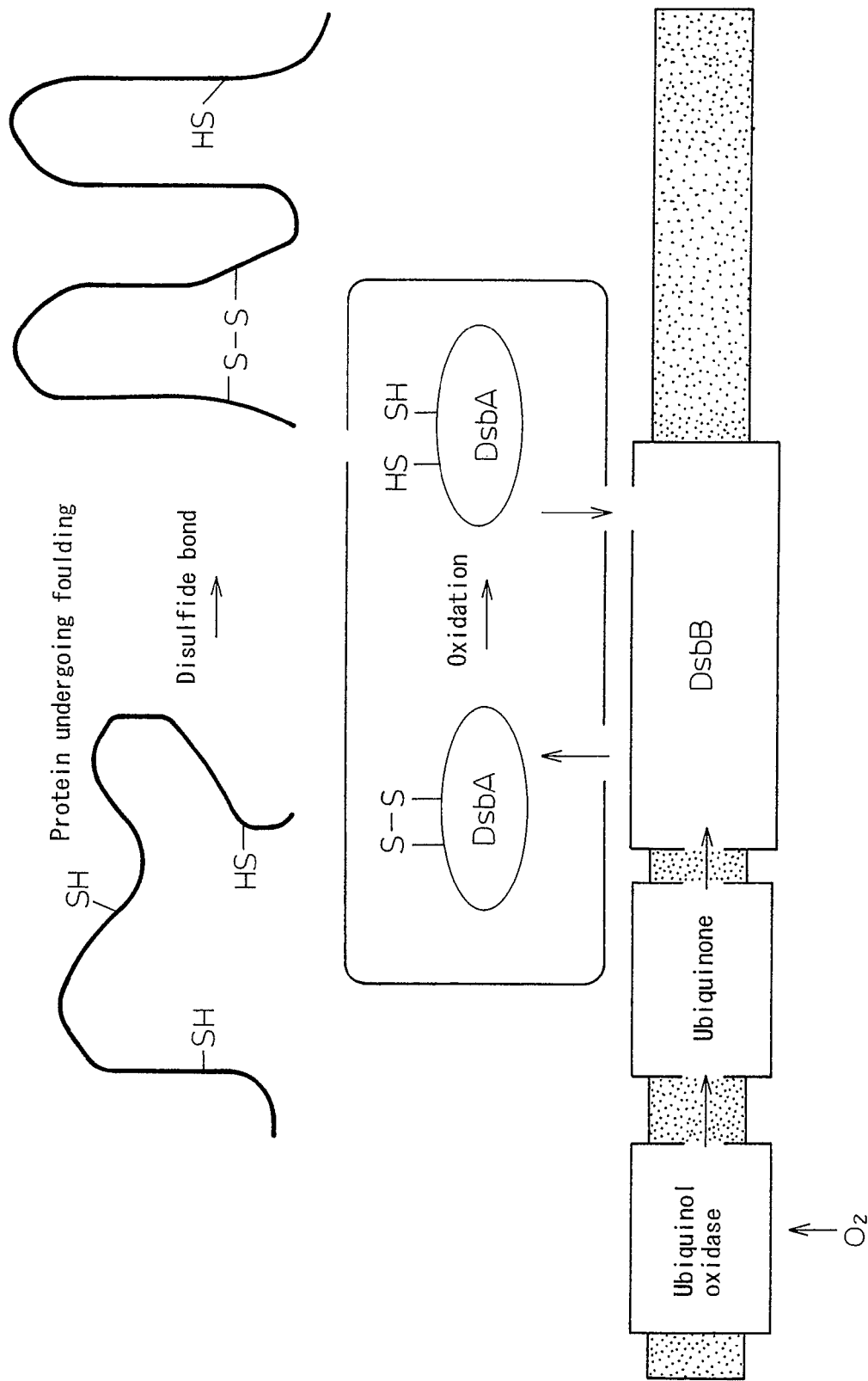

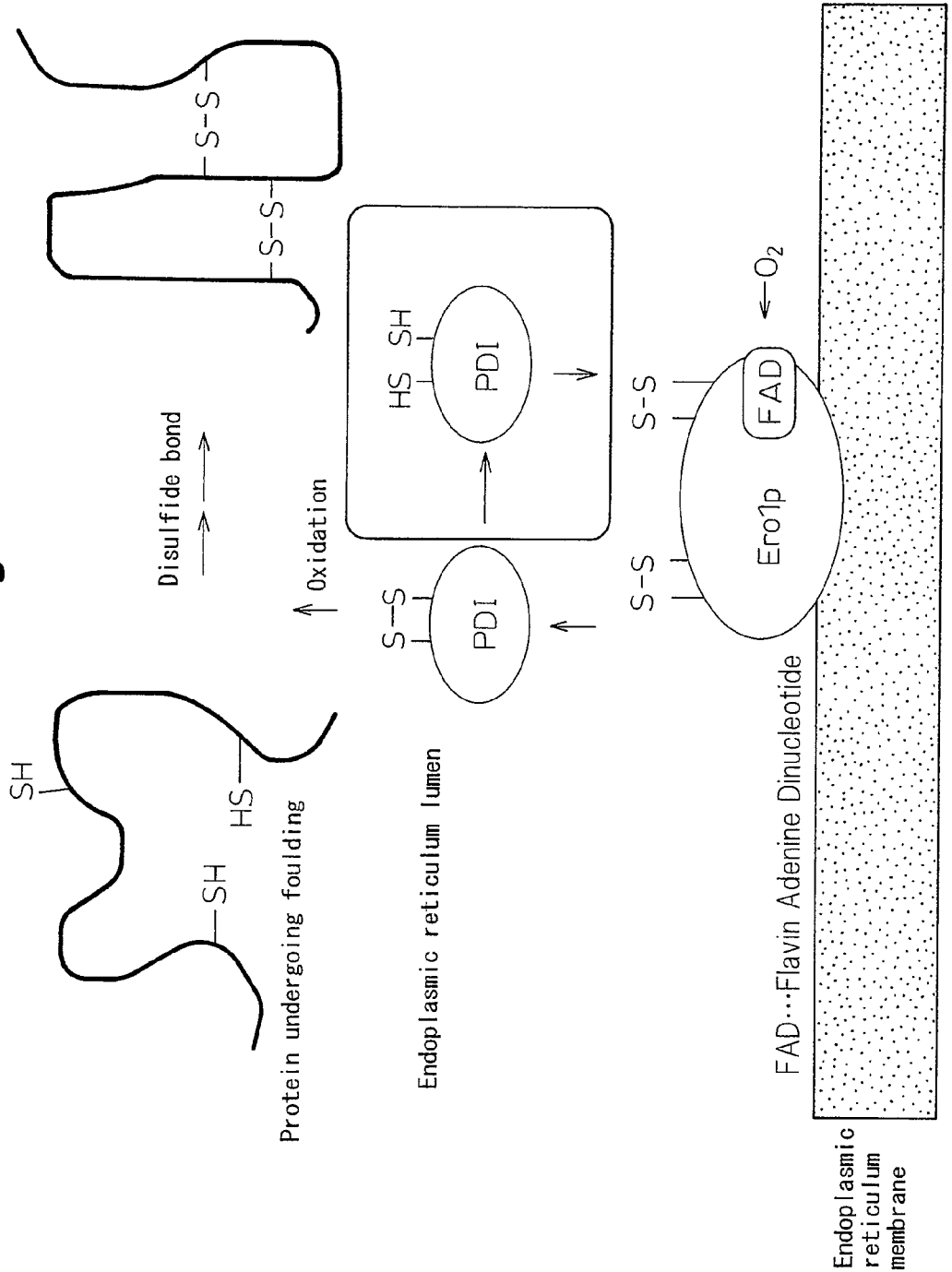

PROTEIN COMPLEX HAVING ACTIVITY CATALYZING ASYMMETRIC OXIDATION REACTION AND PROCESS FOR PRODUCING THE SAME

CROSS-REFERENCE TO RELATED APPLICATION

This application is a National Phase Patent Application and claims the priority of International Application Number PCT/JP2010/058945, filed on May 20, 2010, which claims priority of Japanese Patent Application Number 2009-124645, filed on May 22, 2009.

TECHNICAL FIELD

The present invention relates to a protein complex which at least comprises a protein and calcium, and also has an activity in catalyzing an asymmetric oxidation reaction, and a process for producing the same. The protein complex can be obtained, for example, by encapsulating (or including) a water-soluble crude protein which can easily be separated from an animal or plant tissue, in a gel (calcium alginate gel, etc.), so as to allow the protein to undergo air oxidation, and then separating the protein complex from the resultant oxidation product.

BACKGROUND ART

In various fields including the fields of pharmaceuticals and foods, there has been increasing necessity of a technique of separating an optical isomer to thereby collect the one useful optical isomer. For example, there has been studied a method wherein drugs and perfumes are produced by using an immobilized enzyme having a function of selectively oxidizing/reducing or deracemizing one of optical isomers.

A chemical change in vivo is usually catalyzed by an enzyme. A bioreactor is exemplified as one of the systems of utilizing such an action or mechanism of these enzymes in the production or synthesis of useful substances.

An immobilized enzyme, which has been bonded to an insoluble carrier, takes a leading part of the bioreactor. By use of the immobilized enzyme, a product can easily be separated from the enzyme serving as a catalyst. The immobilized enzyme has widely been used in the fields of research, medical care, analysis and industry. The central part of the bioreactor causing a chemical reaction is a reaction element (or a reaction device), and a purified enzyme, organelle or cell per se is used for the purpose of converting a raw material into a product, or of analyzing by utilizing a chemical change. Since the reaction element must remain in a rector and can be repeatedly used, the reaction element is immobilized by various methods (with respect to details of utilization of these enzymes, for example, it is possible to refer to "Kagaku Zokan (i.e., Chemistry, Special Issue) No. 119, Production of Useful Substances by Hybrid Process", Kagaku Dojin; "Bioreactor" edited by Saburo Fukui, Biotechnology Series, Kodansha Ltd., "Immobilized Enzyme", edited by Ichiro Chibata, Kodansha Scientific Ltd.).

However, since the enzyme requires much cost for purification and the purified enzyme is often unstable, it leaves room for improving the cost burden for stabilization thereof. For this reason, there is an example wherein microorganism containing the objective enzyme was immobilized as it is, in place of the purified enzyme. Examples thereof may include an example wherein microorganisms including aspartase are immobilized, to thereby produce L-aspartic acid, and an example wherein L-alanine is continuously produced by using aspartic acid to be produced in this plant as a raw material (see "Kagaku Zokan No. 119, Production of Useful Substances by Hybrid Process", Kagaku Dojin; "Bioreactor" edited by Saburo Fukui, Biotechnologies Series, Kodansha, Ltd.; "Immobilized Enzyme", edited by Ichirou Chibata, Kodansha Scientific Ltd. and the like).

With respect to a redox catalyst seen from an industrial point of view, e.g., in "Chemical and Industry (i.e. Kagaku To Kogyo)", Vol. 62-1, January 2009, pp. 44-45 (through the development of a biocatalyst), it is considered that a method of utilizing functions of dehydrogenase and coenzyme, which are present in cells, such as microorganisms, yeasts and cultured plant cells, as they are, is dominant in view of cost, and that extra cost burden required to isolate and purify oxidoreductase and coenzyme from biont is not worth the costs of an operation of stabilizing an enzyme, and conjugating a reaction (ketone→alcohol) with a reaction (coenzyme NADH→NAD$^+$) or a reverse reaction thereof.

In recent study of catalyst design to be replaced by the enzyme, there is proposed an example wherein an enzyme-like active domain was produced by introducing a metal complex into a "crude protein".

For example, as known in "Protein, Nucleic Acid, Enzyme", 2004, November, Vol. 49, No. 14—Molecular Design of Metalloenzyme, Mainly Heme Enzyme—(Graduate School of Science, Nagoya University; Yoshihito Watanabe), it is disclosed that oxidation activity occurs even if hem (iron) in an active domain of chloroperoxidase (CPO) is replaced by another metal complex, and it is disclosed that design of appropriate arrangement of a functional amino acid residue in the vicinity of the metal to be arranged is important for the construction of an active domain.

According to the document "Tetrahedron Letters" No. 44, pp. 4281-4284 (1978) (Asymmetric Reduction of aryl trifluoromethyl ketones with an model compound in a chiral hydrophobic binding site of sodium cholate micelle, β-cyclodextrin and bovine serum albumin) "Naomichi Baba et al.; Institute for Chemical Research, Kyoto University", asymmetric reduction is carried out by reacting substrate trifluoromethyl-acetophenone in the presence of 1-propyl-1,4-dihydronicotinamide (NAH) or sodium borohydride (NaBH$_4$) using, as the catalyst, components other than enzyme: surfactant-like bile acid (NAC), β-cyclodextrin (β-CD) and bovine serum albumin (BSA). The above results reveal that an active domain (steric configuration R, optical purity of 46.6% ee) is also present in bovine serum albumin (BSA).

Japanese Patent No. 3,294,860 (a process for producing an optically active alcohol) discloses an example wherein an optically active alcohol was resolved with an optical purity of about 100% ee from a crude protein derived from animals and plants, and an optically active alcohol (100% ee, yield of 50%) is synthesized by using the first step of extracting a water-soluble protein from grains or beans; second step of encapsulating the protein in a calcium alginate gel; and third step of carrying out an asymmetric oxidation conversion reaction of substrate using the encapsulated protein as a catalyst in combination. In Japanese Patent No. 3,683,129 (a process for producing an optically active alcohol), an optically active alcohol (100% ee) is synthesized by using the first step of extracting a water-soluble protein selected from egg white and ovalbumin separated from egg white; the second step of encapsulating the protein in calcium alginate; and the third step of carrying out an asymmetric oxidation conversion reaction of the substrate using the encapsulated protein as a catalyst in combination.

In general, the method of producing an immobilized enzyme is typically the follow methods:

(1) a carrier binding method wherein the extracted and purified enzyme is bound to a water-insoluble carrier, for example, derivatives of polysaccharides, such as cellulose, dextran and agarose; a polyacrylamide gel and the like;

(2) a cross-linking method wherein the extracted and purified enzyme is immobilized by forming a cross-link between he extracted and purified enzymes using a reagent having two or more functional groups; and (3) a (micropcasule type) encapsulating method wherein the extracted and purified enzyme is incorporated in a fine matrix of a gel, for example, a gel such as alginate, starch, konjak (devil's tongue jelly), polyacrylamide gel or polyvinyl alcohol (matrix type) or coated with a semitransparent membrane.

A cross-linked enzyme crystal (CLEC) method which appeared in the 1990s is a method wherein the extracted and purified enzyme is crystallized using ammonium sulfate, polyethylene glycol (PEG) and the like and then cross-linked using a polyhydric modification reagent such as glutaraldehyde (GA), and is used most practically as an industrial immobilized enzyme technique. With respect to the CLEC method, for example, ChiroCLEC (enzyme for the synthesis of chiral compounds) is made into a product as an enzyme for organic synthesis by Altus Co. With respect to ChiroCLEC-BL, subtilisin derived from *Bacillus licheniformis* is immobilized and then cross-linked and solid-phased. With respect to ChiroCLEC-CR, lipase derived from *Candida rugosa* is immobilized and then cross-linked and formed into a solid-phase.

These products exhibit stably activity even in an organic solvent and are also excellent in thermostability. They have a feature that hydrolysis or acylation of carboxylic acid, alcohol, amino acid, ester and the like can be carried out while maintaining optical activity. The cross-linked enzyme crystal (CLEC) (1) can optimize a function of an enzyme under operation conditions that the enzyme is cross-linked and immobilized, (2) can be developed in various commercially available enzymes such as hydrolase, oxidoreductase and lyase, and (3) can be developed by an enzyme capable of producing transgenic microorganism modified so as to meet specific needs.

Japanese Examined Patent Publication (JP-B; KOKOKU) No. 68914 (a process for immobilizing an enzyme) discloses an example wherein an enzyme is adsorbed to an aminated silica gel of a porous water-insoluble carrier, and then the enzyme is immobilized by a covalent binding reaction using a polyfunctional cross-linking agent (glutaraldehyde). In this case, drawbacks of the enzyme, which is likely to leave from a carrier because of a weak binding force between a carrier and an enzyme, is solved by cross-linking the enzyme to a polyfunctional cross-linking agent. A remarkable improvement in half life of activity of an immobilization carrier has been realized by using, in addition to enzyme adsorptivity of porous carriers such as a porous aminated silica gel and a porous aminated zeolite, a polyfunctional cross-linking agent (glutaraldehyde).

Known advantages of the cross-linked enzyme crystal (CLEC) are summarized as follows. Crystallization of the enzyme means that water molecules coated around enzyme molecules are removed by the addition of ammonium sulfate and polyethylene glycol and thus enzyme molecules begin to be polymerized with each other, and means that molecules finally becomes large, resulting in the precipitation thereof. The meaning of the crystallization is different from that in the case of an organic compound wherein a solution of the organic compound is cooled, to thereby solidify the compound.

(Advantages of Cross-Linked Enzyme Crystal)

High-purity enzyme is not required (applicable to a partially purified prepared product)

Simple operation and wide application

Stable at room temperature for a long period (one or more years)

Substantially 100% active protein (high-volume measurement (volumetric) and catalyst productivity)

Easy recovery and recycling

High-temperature stability and resistance to organic solvent as compared with enzyme alone High activity and selectivity (may be sometimes higher than those of enzyme alone)

There's no need to filtrate an enzyme in an aqueous medium

Quick optimization (using HTE) shortens a development time

Combi CLEA containing one or more enzymes for catalytic cascade process

Examples of market and possibility of application of the cross-linked enzyme crystal (CLEC) include CLEC synthesis (drugs, perfumes and taste substances, pesticides, functional foods, fine chemicals, bulky monomers), foods and beverages, pulps and papers, cosmetics, oils and lipids, woven fabrics, waste treatment, surfactants, biosensors, diagnostic drugs, protein transport and the like.

With respect to dehyrdrogenases, microorganisms-derived alcohol dehydrogenase (ADH) from *Rhodococcus erythropolis*, and formate dehydrogenase (FDH) from *Candida boidinii* are known as enzymes for preparation of CLEA, at present.

PRIOR ART DOCUMENTS

Patent Document
Patent Document 1: Japanese Patent No. 3,294,860
Patent Document 2: Japanese Patent No. 3,683,129
Patent Document 3: JP-B No. 4-68914
Non-Patent Document
Non-Patent Document 1: "Kagaku Zokan No. 119, Production of Useful Substances by Hybrid Process", Kagaku Dojin, "Bioreactor" edited by Saburo Fukui
Non-Patent Document 2: Biotechnologies Series, Kodansha Ltd., "Immobilized Enzyme", edited by Ichirou Chibata, Kodansha Scientific Ltd.
Non-Patent Document 3: "Chemistry and Industry (i.e., Kagaku To Kogyo), Vol. 62-1, January 2009, pp. 44-45
Non-Patent Document 4: "Protein, Nucleic acid, Enzyme" 2004, November, Vol. 49, No. 14, —Molecular Design of Metalloenzyme, Mainly Heme Enzyme—(Graduate School of Science, Nagoya University; Yoshihito Watanabe)
Non-Patent Document 5: "Tetrahedron Letters" No. 44, pp. 4281-4284 (1978) (AsymMetric Reduction of aryl trifluoromethyl ketones with an model compound in a chiral hydrophobic binding site of sodium cholate micelle, β-cyclodextrin and bovine serum albumin) "Naomichi Baba et al.; Institute for Chemical Research, Kyoto University"
Non-Patent Document 6: "Food and Technology (i.e., Shokuhin To Gijutshu)", October, pp. 1-9 (2008) (Role of Table or Common Salt in Network Formation of Gluten Protein), "Reiko Urade; Graduate School of Agriculture, Kyoto University"
Non-Patent Document 7: Crystal structure of the DsbB-DsbA complex reveals a disulfide bond severation mechanism-Cell 127, 789-801 (2006) (Kenji Inaba et al.; Medical Institute of Bioregulation, Kyushu University)

Non-Patent Document 8: —STRUCTURE-FUNCTION STUDIES OF GLUTAREDOXINS AND RELATED OXIDOREDUCTASRE—" (Tobias H. ElGAn; From THE DEPARTMENT OF BIOSCIENCES AND NUTRITION Karolinska Institutet, Stockholm, Sweden)

SUMMARY OF THE INVENTION

Problems to be Solved by the Invention

An object of the present invention is to overcome the above-mentioned drawback of the prior art, and to provide a useful material which enables an efficient enzyme-mimetic reaction under a mild condition.

Another object of the present invention is to provide a material having an "enzyme-mimetic" reaction activity, which is excellent in environmental aspects and safety.

Still another object of the present invention is to provide a suitable process for producing a material having such "enzyme-mimetic" reaction activity.

Means for Solving the Problems

As a result of an earnest study, the present inventors have found a protein complex having an activity in catalyzing an asymmetric oxidation reaction.

The protein complex of the present invention has been made based on the above discovery, and is more specifically a protein complex which comprises at least protein and calcium, and also has an activity in catalyzing an asymmetric oxidation reaction.

The present inventors have further made a progress of a study based on the above discovery and found a method capable of efficiently obtaining the above protein complex having useful properties. The production method of the present invention has been made based on the above discovery, and more specifically includes the first step of concentrating a crude protein from a water-soluble moiety derived from animal and plant; the second step of encapsulating the protein in a gel, to thereby allow the protein to undergo air oxidation, and then extracting a protein complex from the gel; the third step of allowing the extracted protein complex to undergo crystallization precipitation in an aqueous solution; and the fourth step of cross-linking the precipitated protein complex.

According to an aspect of the above production method, it is possible to include the first step of concentrating a crude protein from a water-soluble moiety of animal and plant; the second step of encapsulating the crude protein in a calcium alginate gel, exposing the gel to air for several times (air oxidation), shaking in warm water and then extracting a protein complex; the third step of subjecting the protein complex to saturated 30% ammonium sulfate precipitate; and the fourth step of cross-linking the precipitated crystallized protein complex.

According to another aspect of the present invention, an inexpensive crude protein derived from animal and plant is encapsulated in a calcium alginate gel and the gel beads (in the presence of oxygen and dissolved calcium) are subjected to air oxidation, to thereby induce (i) intermolecular disulfide bond, (ii) intermolecular aggregation (<6.4 Å) and (iii) change in water solubility (protein complex formation), and then the complex can be suitably extracted by shaking in warm water.

According to an aspect of the present invention, it is also possible to synthesize an optically active alcohol of about 100% e.e. by asymmetric oxidation of one enantiomer of a substrate racemic alcohol even in case of using a protein complex or a cross-linked crystallized protein complex, and also to provide a specific production method.

According to an aspect of the present invention, it is also provided that a protein complex of a crude protein derived from animal and plant has, in addition to a reaction of selective asymmetric oxidation to one enantiomer of a secondary alcohol substrate having a benzene skeleton (or structure) or a naphthalene skeleton (yield of 50%), deracemization reaction activity (yield>85%) of alkyl-chain secondary alcohols having no skeleton mentioned above, such as Matsutakeol.

The subject matter of present invention is not the production of the above-mentioned purified enzyme derived from microorganisms, transgenic enzyme derived from microorganisms, or microorganisms or transgenic microorganisms, and immobilized enzyme derived from animal tissue (liver, pancreas, etc.) and immobilized microorganism, and it is one of features of the present invention that the subject matter thereof is a more inexpensive crude protein derived from animal and plant resources which does not require the step of isolation and purification of an enzyme at high cost. Examples of the "plant resource" include grains such as buckwheat, amaranth, rice, wheat, barley, corn, oats, rye, foxtail millet, barnyard millet, millet, adlay and sorghum; beans such as adsuki beans, kidney beans, green peas, green beans and soy beans; and the respective plant tissue of seeds, leaves, stems, roots, flowers and fruits of general grasses and weeds further included therein.

Examples of the "animal resource" include those derived from chicken egg as egg white or ovalbumin, and egg albumin of chickens, amphibians and fishes can be similarly used. There is no limitation on those derived from chicken egg, and protein origin is not limited to egg.

In an aspect of the present invention, as mentioned below, it also becomes possible to produce a protein complex, which is environmentally friendly and is low-cost and also has high storability, wherein the first step of extracting a water-soluble protein from grains, beans, and the respective plant tissue of seeds, leaves, stems, roots, flowers and fruits of general grasses and weeds further included therein; the second step of encapsulating the protein in a calcium alginate gel, to thereby allow the protein to undergo air oxidation, shaking in warm water at 40° C. for 10 hours or more, and separating an aqueous protein complex solution fraction from the beads; the third step of adjusting the aqueous protein complex solution fraction to 30% saturated ammonium sulfate, to thereby form a precipitate; the fourth step of cross-linking the obtained crystallized protein complex using glutaraldehyde; and the fifth step of drying (FD) the obtained crosslinked crystallized protein complex, to thereby form a powder in combination.

Effects of the Invention

As described above, according to the present invention, there is/are provided a protein complex derived from plant and/or a protein complex derived from animal, imparted with a practical asymmetric oxidation activity. According to the present invention, there is further provided a process for producing a protein complex, which is suited for the cross-linked crystallized protein derived from animal and plant, and is environmentally friendly and realize low cost production.

BRIEF DESCRIPTION OF THE DRAWINGS

FIG. 2c is a graph wherein green pea-calcium alginate gel beads prepared by added dropwise in a different concentration of calcium chloride is blank-shaken for 10 hours and then reacted with a substrate R-1-(2-naphthyl)ethanol, and a protein complex activity is examined in the second step of the production method of the present invention.

Herein, an eluted solution is a solution fraction after shaking in warm water for 10 hours or more. An ammonium sulfate precipitate is a precipitate when the eluted solution is adjusted to a 30% ammonium sulfate solution. The supernatant is a supernatant fraction obtained by centrifugal separation of a solution prepared by redissolving the ammonium sulfate precipitate in water.

Figure 4:
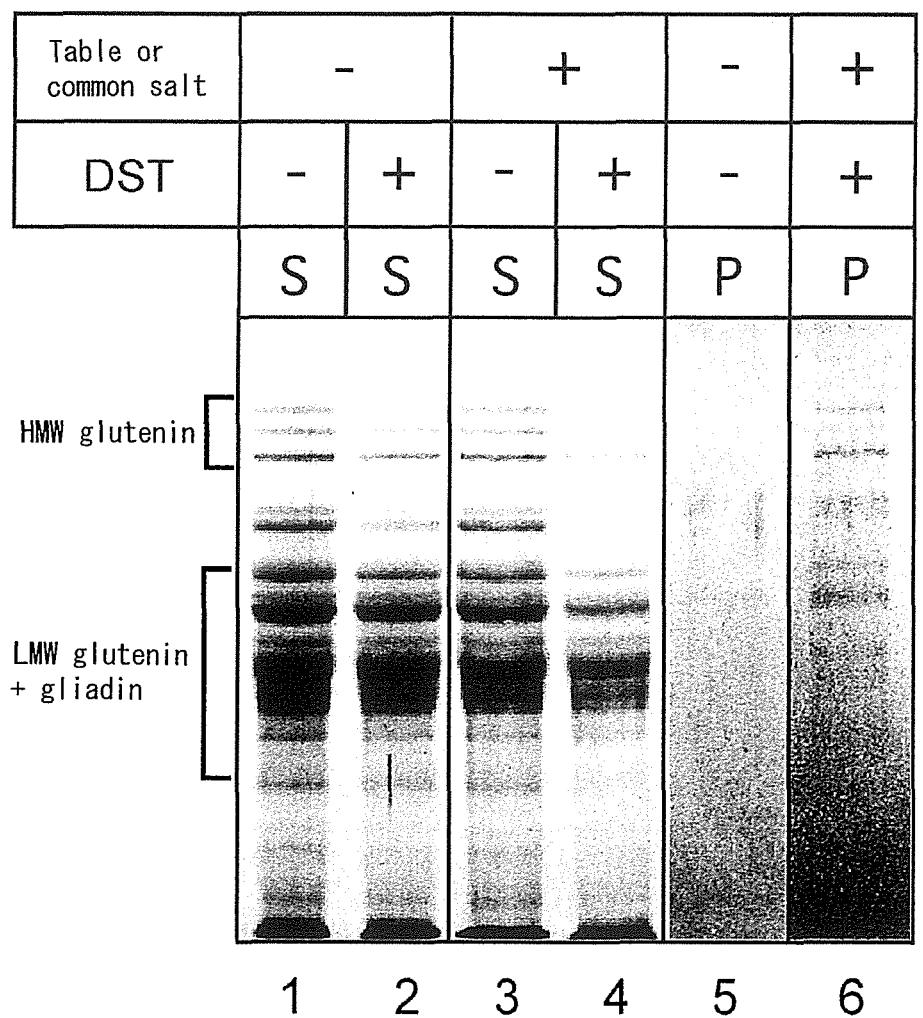

FIG. 4 is SDS-page of a component soluble in an SDS solution containing β-mercaptoethanol of a wheat gluten dough with or without addition of a common or table salt found in the description (Role of a Table or Common Salt in Network Formation of Gluten Protein) of Reiko Urade, in "Food and Technology", 2008 December, General remarks.

Figure 5:
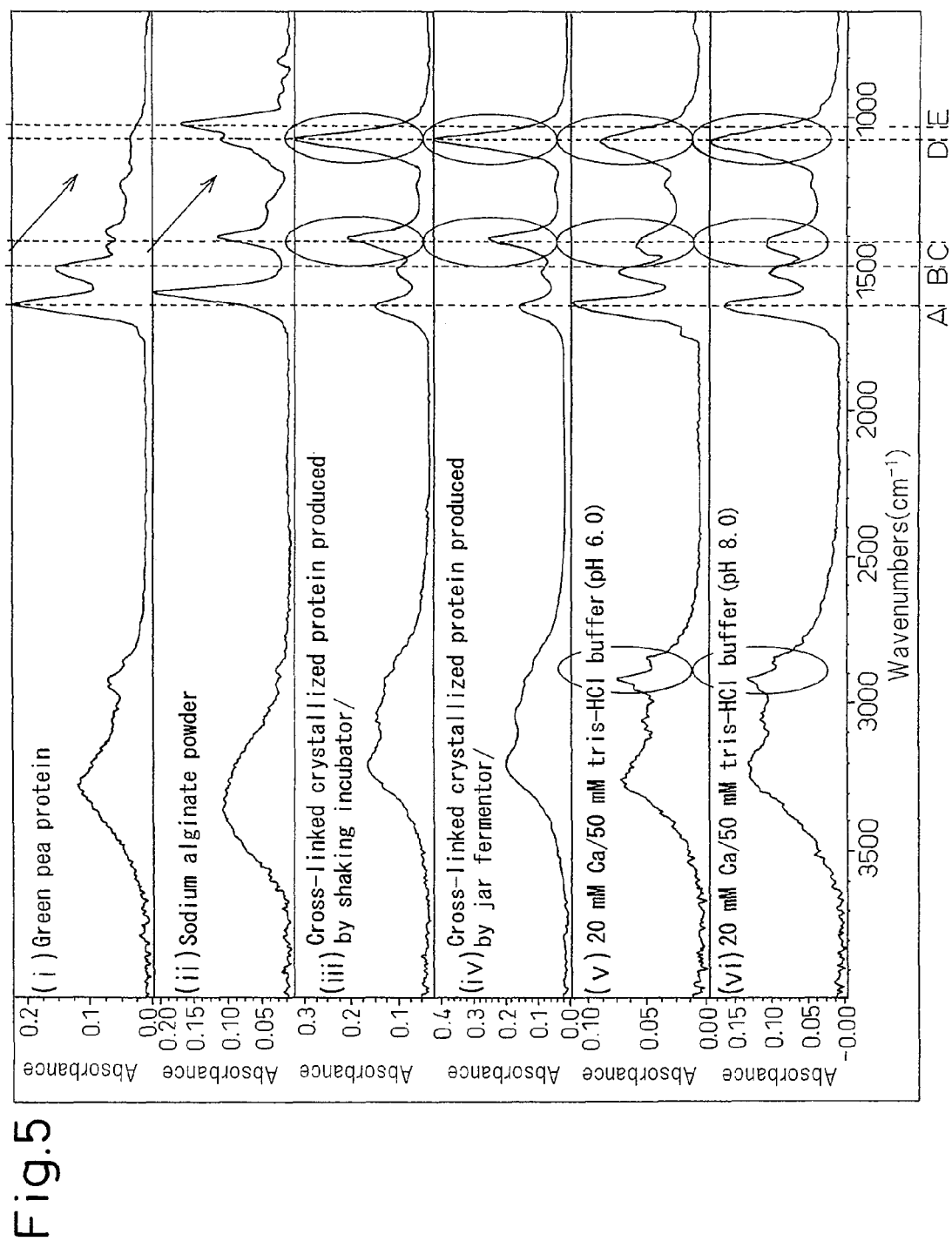

FIG. 5 shows qualitative analytical results of samples (i) to (vi) using Fourier transform infrared spectrophotometry (FT-IR).

FIG. 6a shows qualitative analytical results of samples (i) to (iv) using an X-ray microanalyzer EPMA-1600.

Figure 6B:
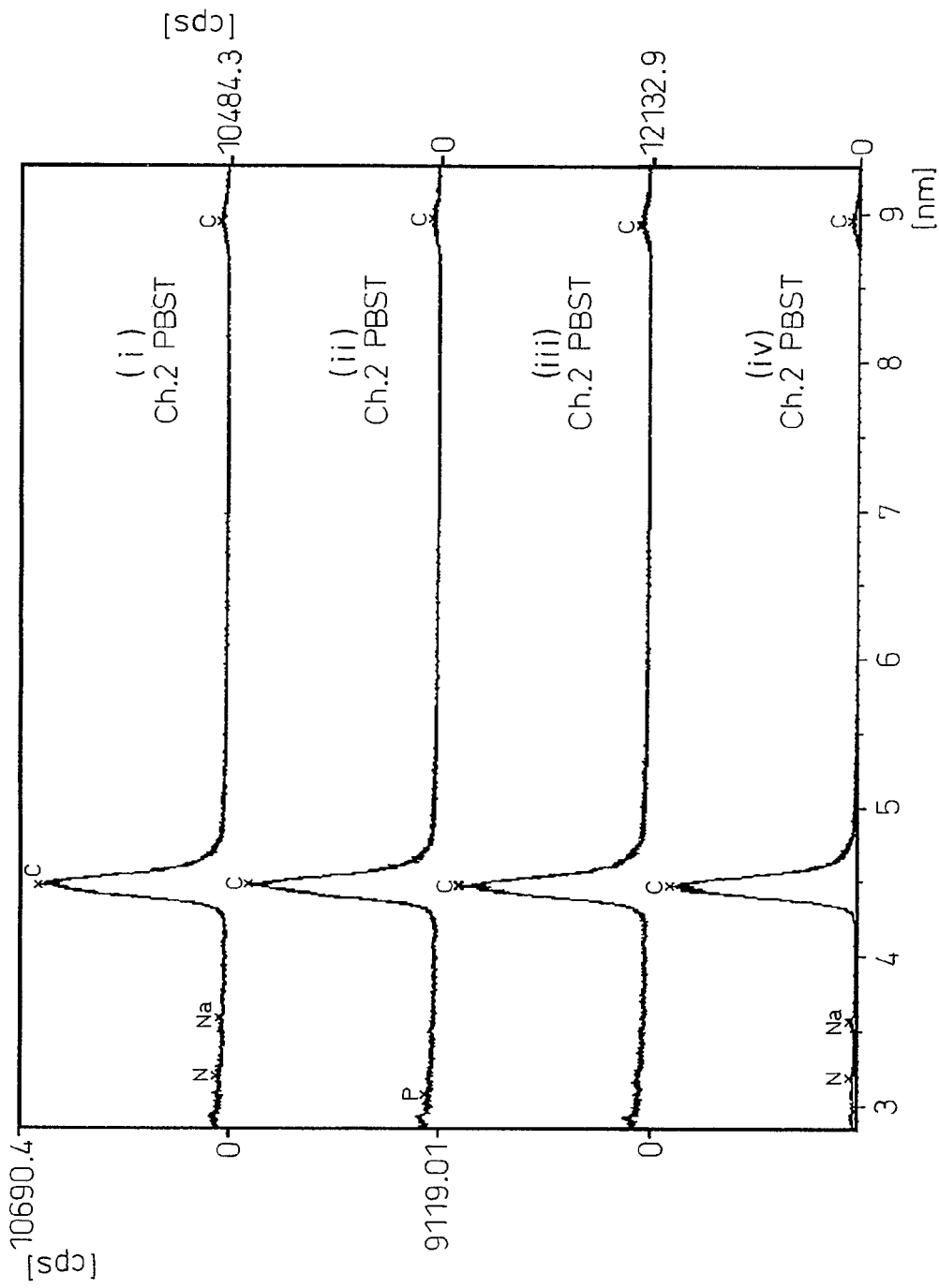

FIG. 6b shows qualitative analytical results of samples (i) to (iv) using an X-ray microanalyzer EPMA-1600.

FIG. 6c shows qualitative analytical results of samples (i) to (iv) using an X-ray microanalyzer EPMA-1600.

FIG. 6d shows qualitative analytical results of samples (i) to (iv) using an X-ray microanalyzer EPMA-1600.

Figure 7:
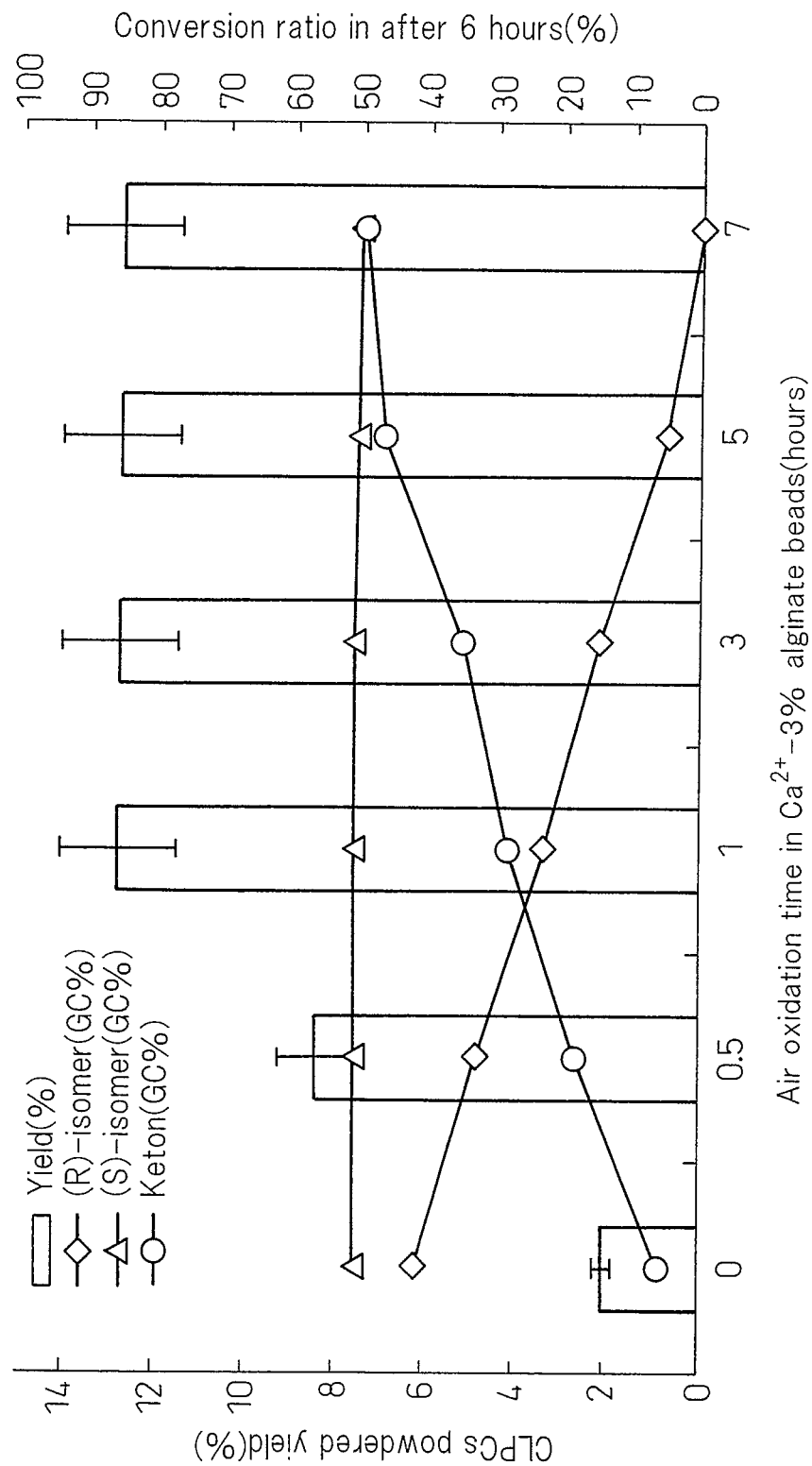

FIG. 7 is a graph wherein a yield of a protein complex obtained by leaving a green pea-calcium alginate gel to stand in air for a predetermined time, extracting a protein complex, followed by cross-linking crystallization and further freeze-drying, and an asymmetric oxidation activity (right axis) after 6 hours is monitored in the second step of the production method of the present invention.

FIG. 8 is a GC chromatogram of a perfume R-1-octen-3-ol (Matsutakeol; 98.2% ee) synthesized by reacting a protein complex with a substrate racemic 1-octen-3-ol in the second step.

Figure 9A:
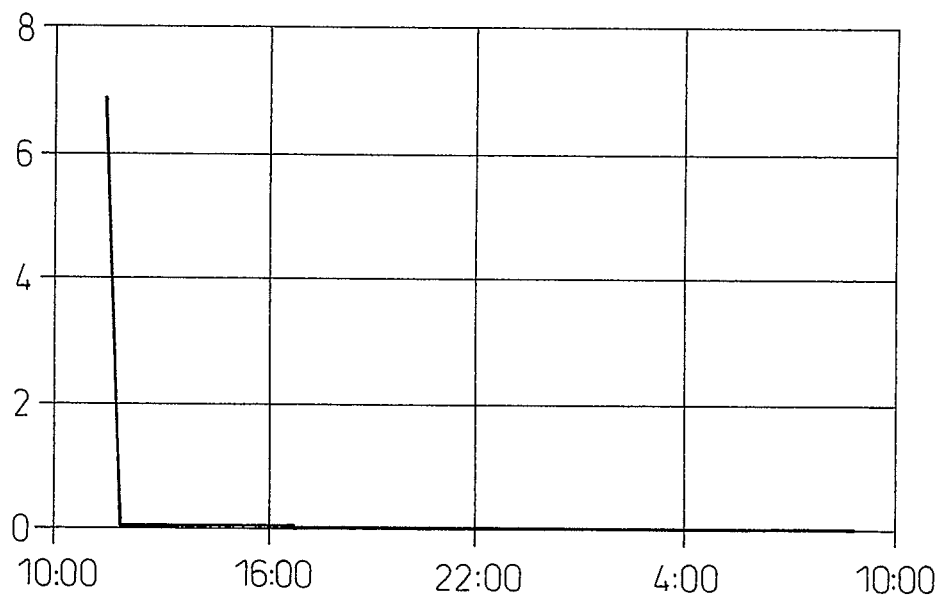

FIG. 9a shows a transition of DO (dissolved oxygen) in 100 L jar production of a protein complex in the second step of the production method of the present invention.

Figure 9B:
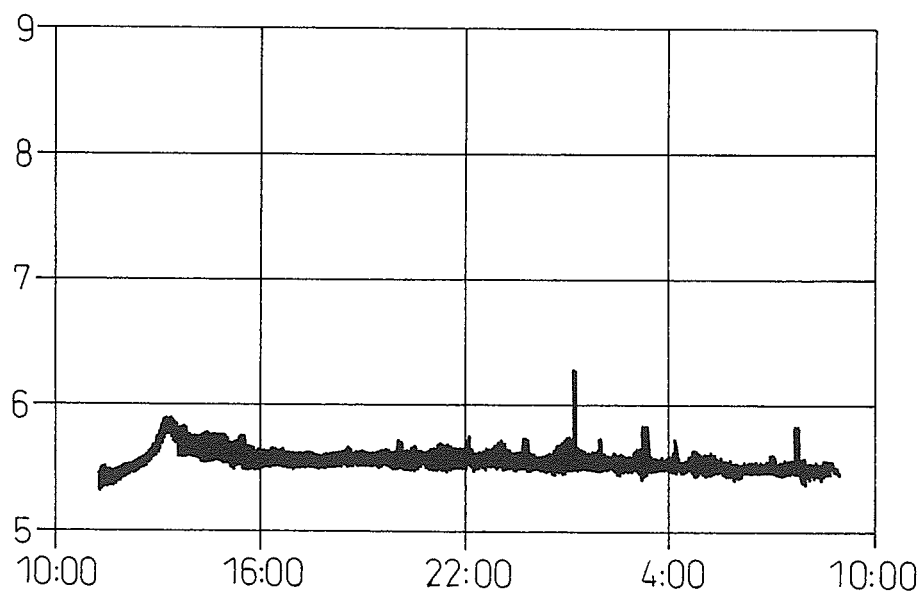

FIG. 9b shows a transition of pH in 100 L jar production of a protein complex in the second step of the production method of the present invention.

Figure 9C:
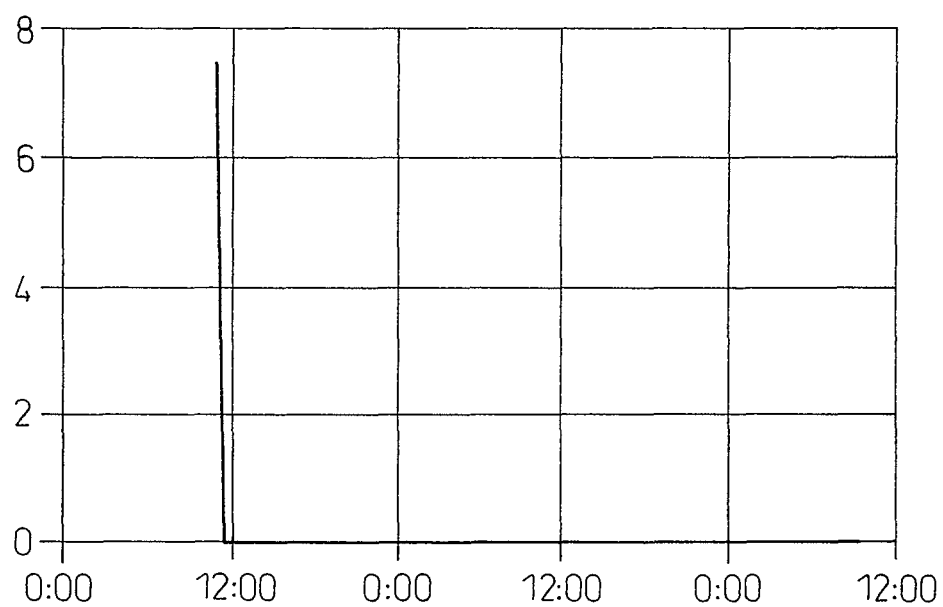

FIG. 9c shows a transition of DO (dissolved oxygen) in 100 L jar production of a protein complex in the second step of the production method of the present invention.

Figure 9D:
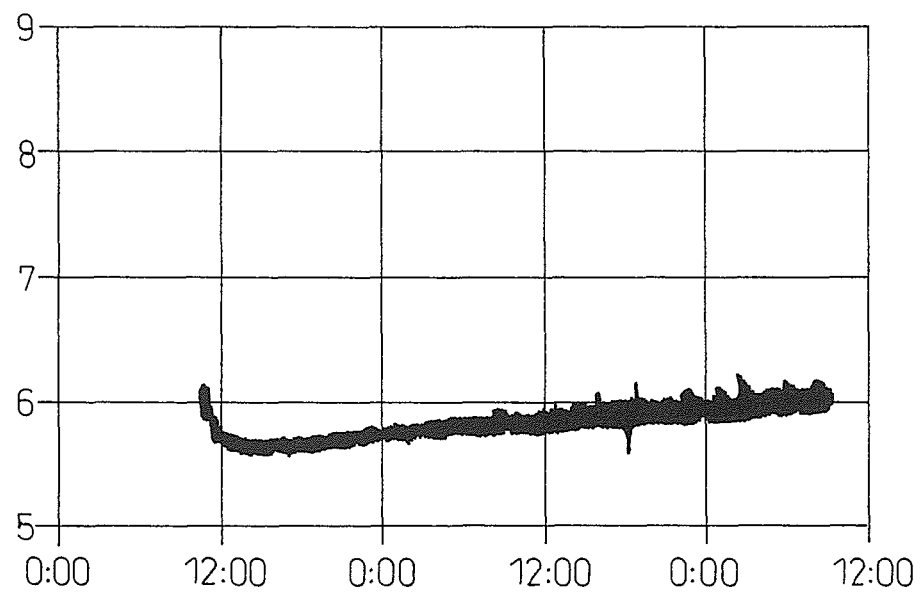

FIG. 9d shows a transition of pH in 100 L jar production of a protein complex in the second step of the production method of the present invention.

Figure 9E:
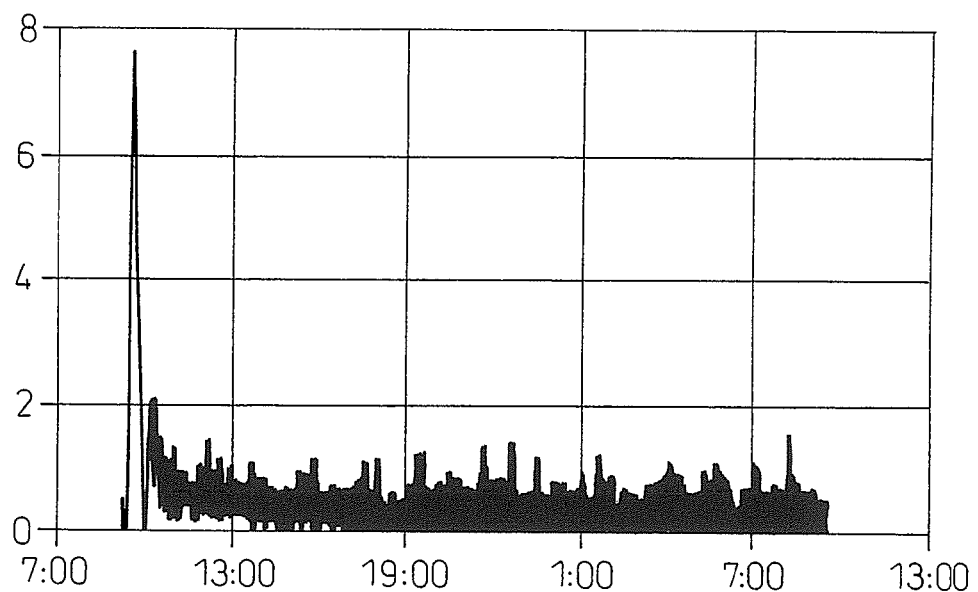

FIG. 9e shows a transition of DO (dissolved oxygen) in 100 L jar production of a protein complex in the second step of the production method of the present invention.

Figure 9F:
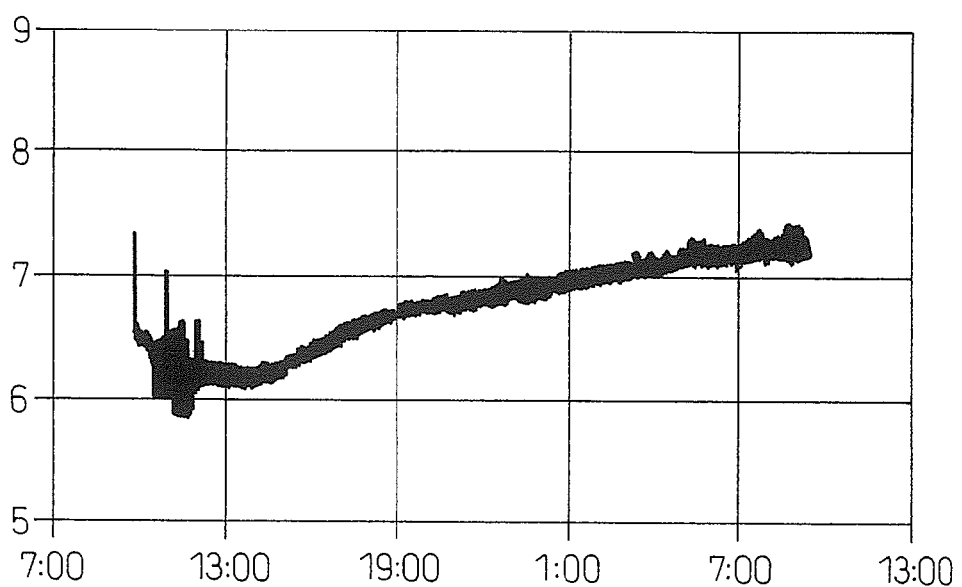
Figure 9G:
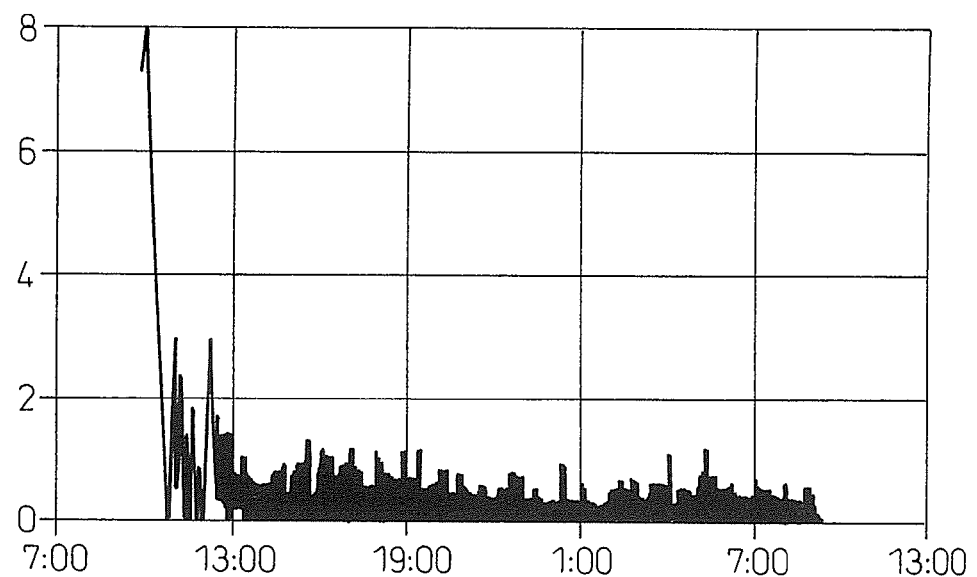

FIG. 9f shows a transition of pH in 100 L jar production of a protein complex in the second step of the production method of the present invention, FIG. 9g shows a transition of DO (dissolved oxygen) in 100 L jar production of a protein complex in the second step of the production method of the present invention.

Figure 9H:
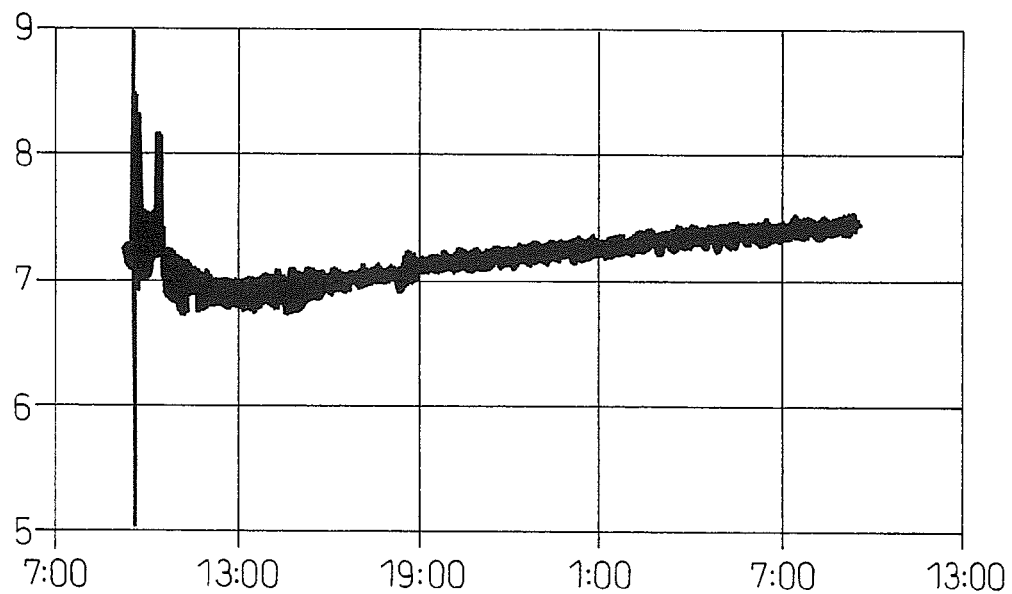

FIG. 9h shows a transition of pH in 100 L jar production of a protein complex in the second step of the production method of the present invention.

Figure 10:
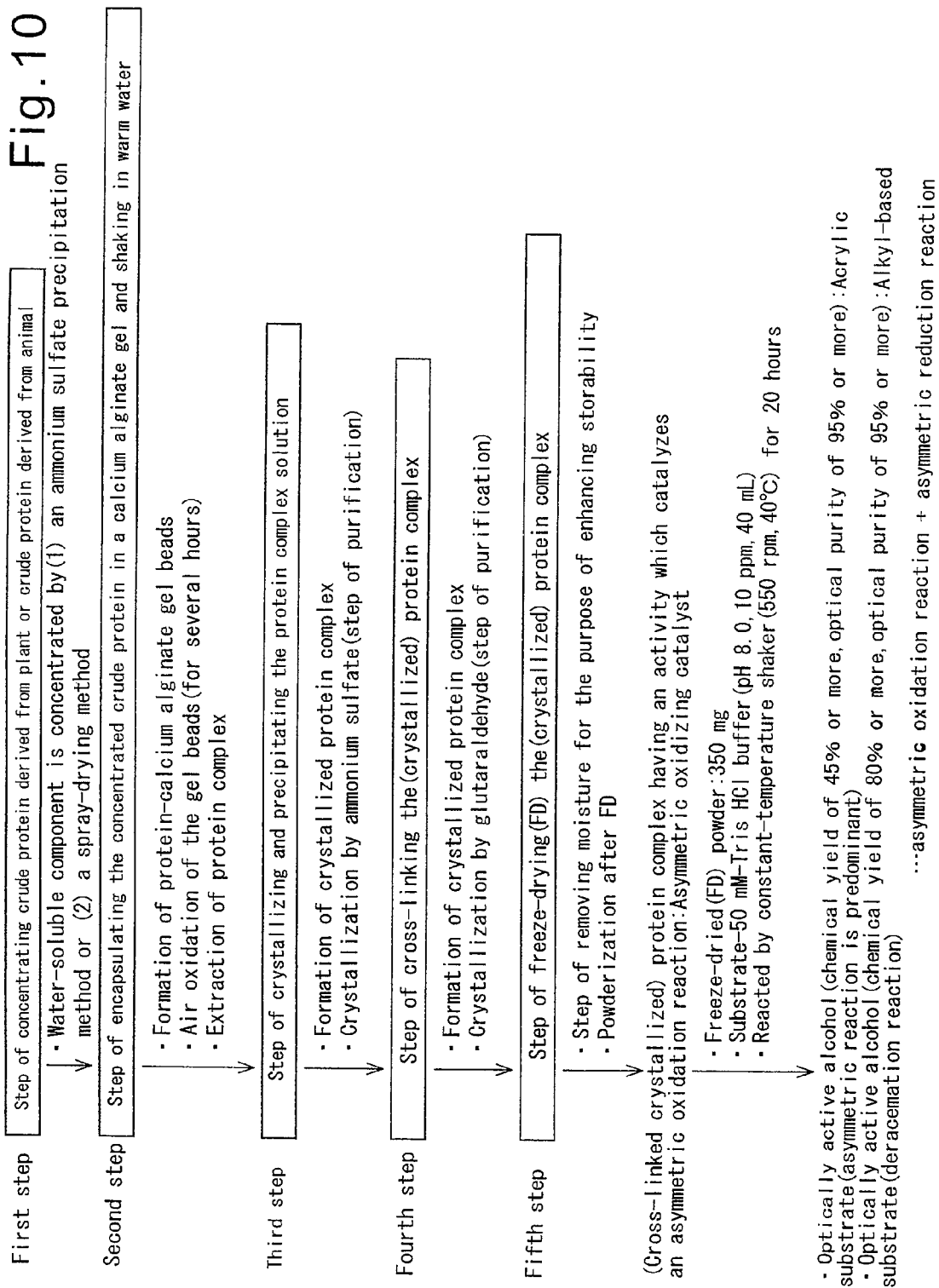

FIG. 10 shows a production flow of all production steps of a protein complex, and brief description of each step.

FIG. 11a shows a cell system (Journal of the American Chemical Society, "Crystal structure of the DsbB-DsbA complex reveals a disulfide bond severation mechanism", Cell, Vol. 127, Issue 4, 789-801, Nov. 17, 2006: Kenji Inaba et al. (citing the drawing of Medical Institute of Bioregulation, Kyushu University)) for formation of a protein disulfide bond in procaryote (*Escherichia coli*).

FIG. 11b shows a cell system (Journal of the American Chemical Society, "Crystal structure of the DsbB-DsbA complex reveals a disulfide bond severation mechanism", Cell, Vol. 127, Issue 4, 789-801, Nov. 17, 2006: Kenji Inaba et al. (citing the drawing of Medical Institute of Bioregulation, Kyushu University)) for formation of a protein disulfide bond in eucaryote (yeast endoplasmic reticulum).

Figure 12:
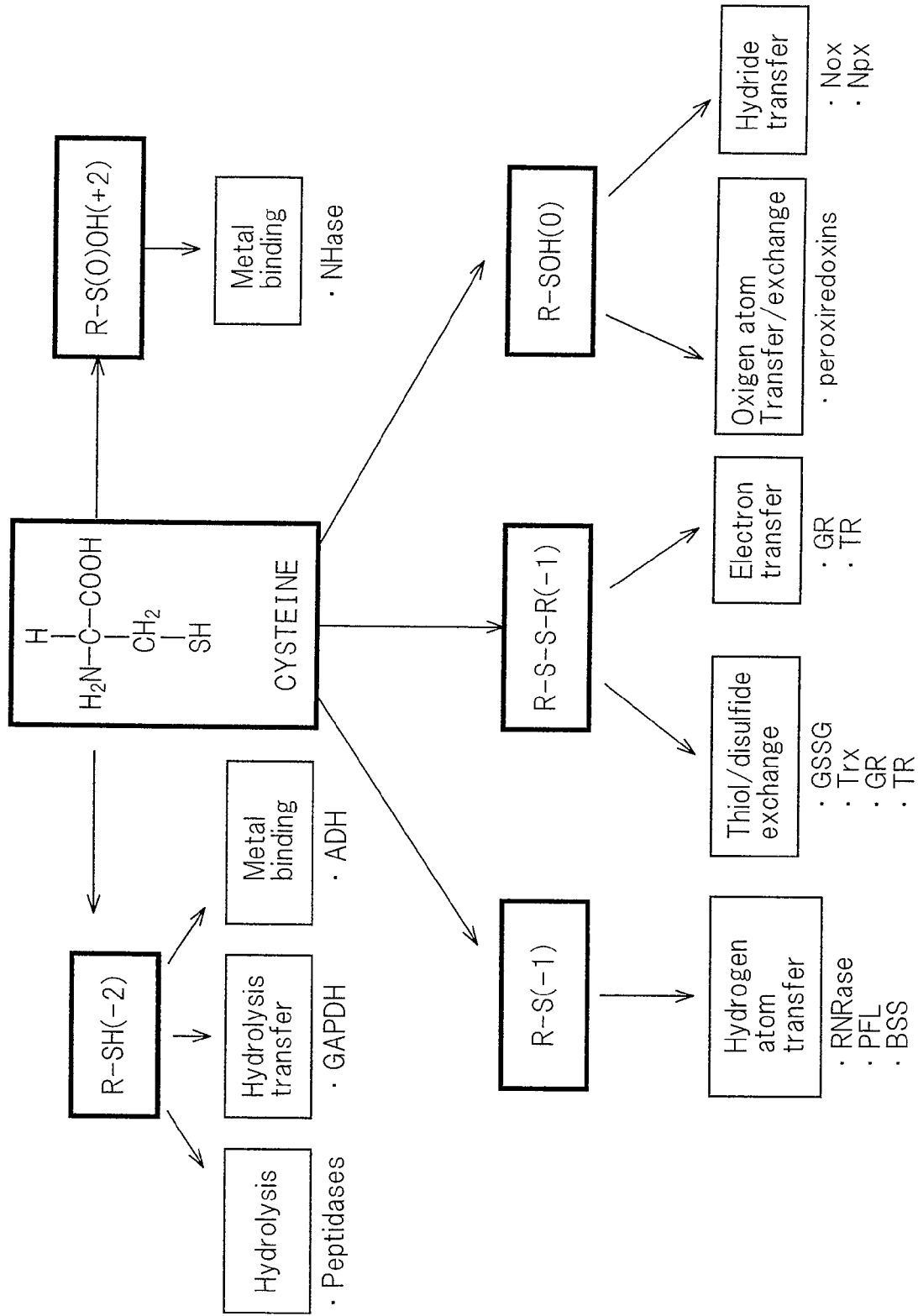

FIG. 12 is a block diagram showing kinds and the enzymatic function (reactivity) of a sulfide-based enzyme obtained by cysteine oxidation in cells.

Figure 13:
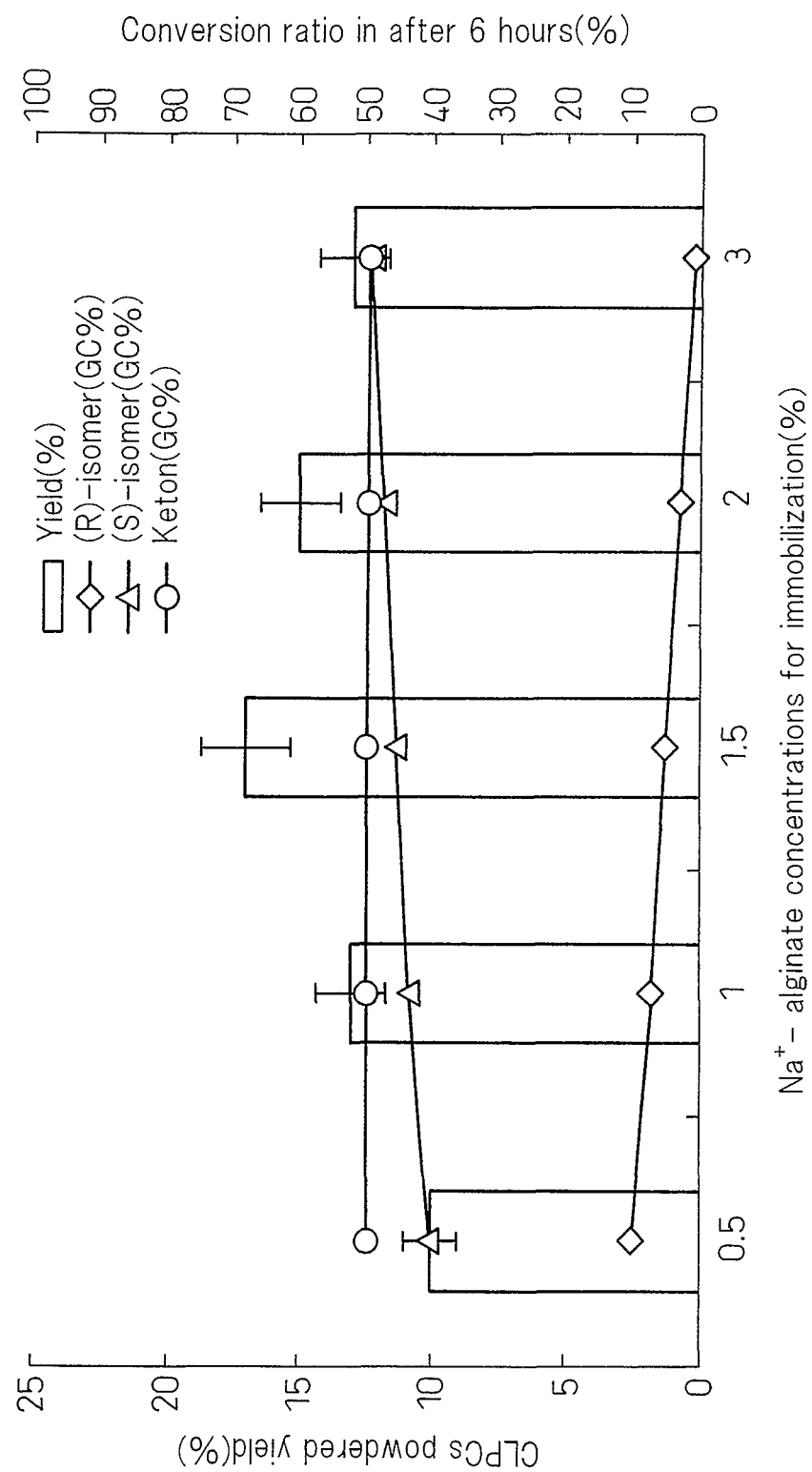

FIG. 13 is a graph wherein a yield and an oxidation activity of those obtained by freeze-drying cross-linked crystallized protein complexes (CLPCs) obtained in Example 20, followed by ball mill crushing are summarized.

Figure 14:
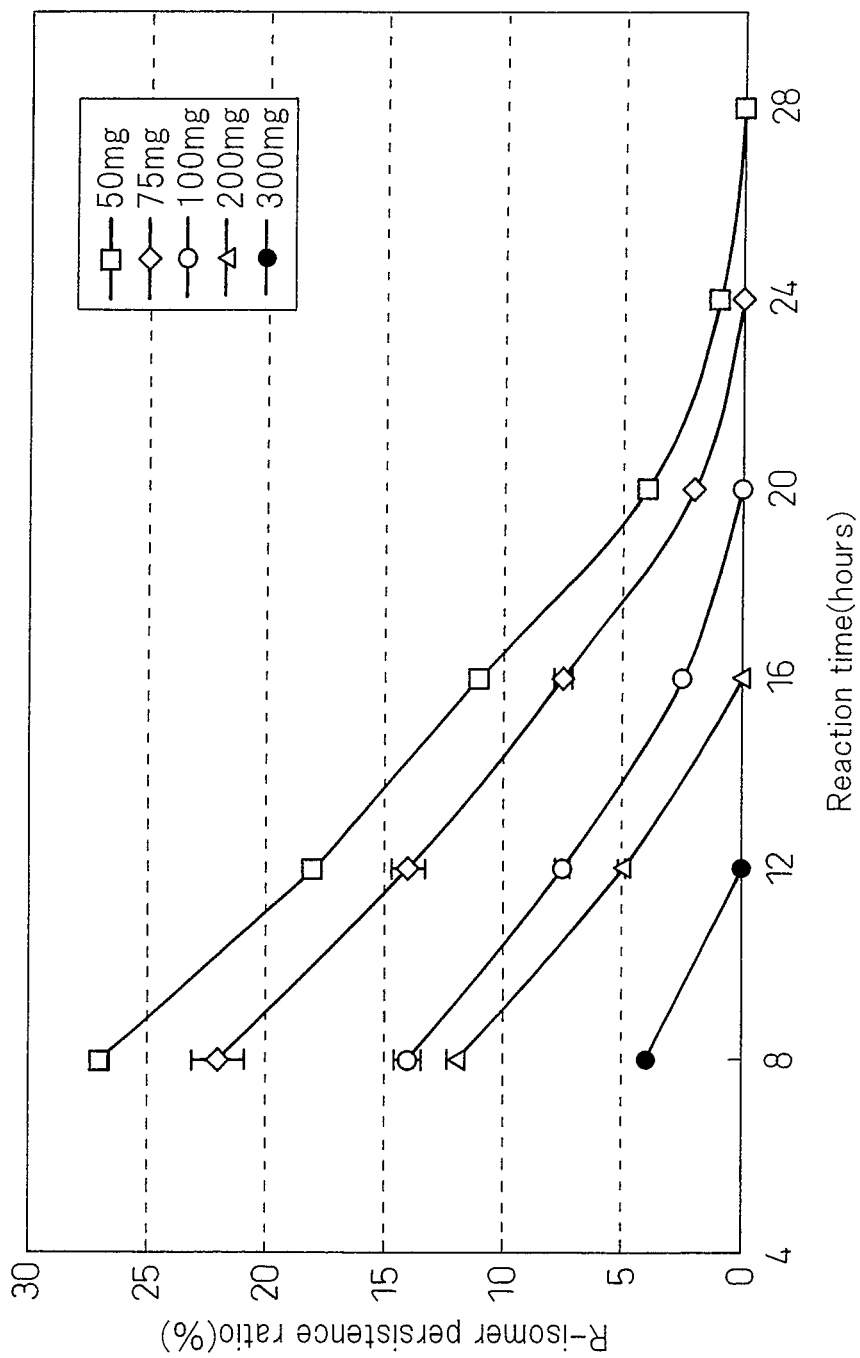

FIG. 14 is a graph showing the results of tracing of a persistence ratio of R-1-(2-naphthyl)ethanol which is obtained by adding 40 ml of 50 mM Tris HCl (pH 8.0) buffer of a racemic 1-(2-naphthyl)ethanol concentration having a concentration of 10 ppm to a freeze-dried (FD) powder (50 mg, 75 mg, 100 mg, 200 mg, 300 mg) of the protein complex obtained in Example 20 in a 200 ml Erlenmeyer flask, and reacting them through warm water shaking in a constant-temperature shaking incubator (40° C., 55 rpm), followed by asymmetric oxidation (every 4 hours) using GC.

Figure 15:
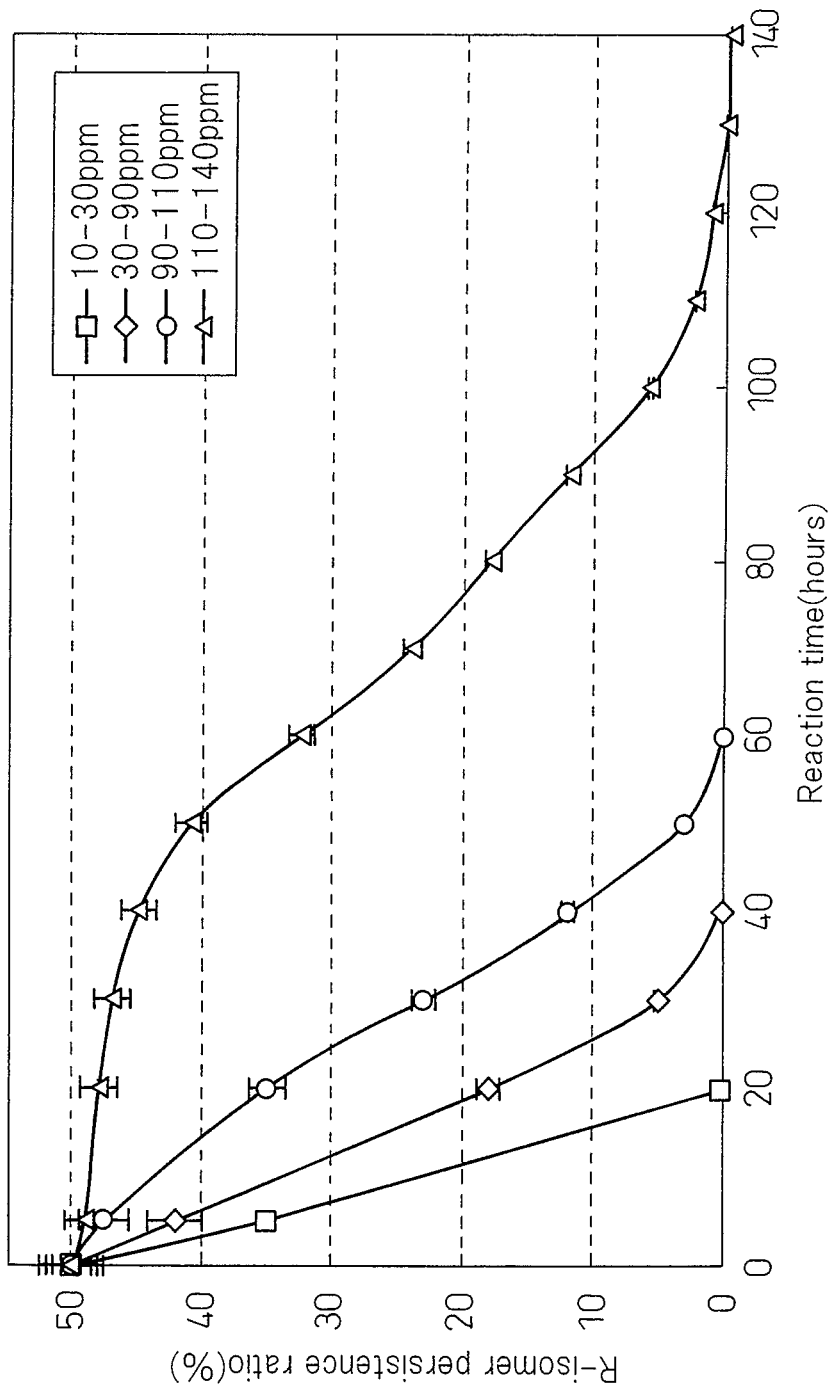

FIG. 15 is a graph showing the results of GC tracing (every 4 hours) of a persistence ratio of R-1-(2-naphthyl)ethanol which is obtained by adding 40 ml of 50 mM Tris HCl (pH 8.0) buffer containing a racemic 1-(2-naphthyl)ethanol having a concentration (10-140 ppm) to a freeze-dried (FD) powder (300 mg) obtained in Example 20 in a 200 ml Erlenmeyer flask, and reacting them through warm water shaking in a constant-temperature shaking incubator (40° C., 55 rpm), followed by asymmetric oxidation.

MODE FOR CARRYING OUT THE INVENTION

The present invention will be described more specifically while optionally referring to the accompanying drawings. In the following description, "parts" and "percentages" representing a quantitative ratio are by mass unless otherwise specified.
(Protein Complex)
The protein complex of the present invention is characterized in that it comprises at least a protein and also has at least one peak in a region of $(1,085\pm50\ cm^{-1})$ and a region of $(1,411\pm50\ cm^{-1})$ respectively in FT-IR. Herein, as mentioned below, FT-IR can be measured, for example, by a Micro-ATR method (Ge crystal), using a Fourier-transform infrared spectrometer Magna-750 manufactured by Thermo Fisher Scientific and an infrared microscope Nic-Plan, under the conditions of a frequency resolution of 8 $cm^{-1}$ and integration times of 32 times. (With respect to details of the FT-IR measurement, for example, the document "Carbohydrate Polymers" 66, 191-197, (2005) (Enzymatically Produced nano-ordered short elements containing cellulose $I_\beta$ crystalline domains) "Noriko Hayashi et al.; Bioconversion Laboratory, Forestry and Forest Products Research Institute (FFPRI)" discloses Examples. With respect to the evaluation of absorption wavelength, it is possible to refer to the book "ACADEMIC PRESS; New York and London 1971; A Subsidiory of Harcourt Brace Jovanovich, Publishers" INFRARED SPECTRA OF INORGANIC COMPOUNDS (3800-45 $cm^{-1}$)" [Richard A. Nyquist and Renald 0. Kagel; Chemistry Physics Research Laboratory, The Dow Chemical Company Midland MichiGAn].
(Intensity of IR Peak)
In the protein complex of the present invention, the peak intensity in the above FT-IR measurement is preferably as follows.
(1) The peak in a region of $(1,085\pm50\ cm^{-1})$ (hereinafter referred to as a "peak 1") is preferably a peak having the largest intensity among the measured IR spectrum, or has a peak intensity of $(1/10)\times I_0$ or more when the intensity of a peak having the largest intensity denotes $I_0$. This peak intensity is more preferably $(1/5)\times I_0$ or more (especially $(1/3)\times I_0$ or more).
(2) The peak in a region of $(1,411\pm50\ cm^{-1})$ (hereinafter referred to as a "peak 2") is preferably a peak having the largest intensity among the measured IR spectrum, or has a peak intensity of $(1/10)\times I_0$ or more when the intensity of a peak having the largest intensity denotes $I_0$. This peak intensity is more preferably $(1/5)\times I_0$ or more (especially $(1/3)\times I_0$ or more).
(Intensity of Other IR Peaks)
In the protein complex of the present invention, there is no particular limitation on IR peaks other than the above-mentioned "peak 1" and "peak 2". The protein complex of the present invention may have a peak, for example, in the below-mentioned region.
In the protein complex of the present invention, evaluation of the above FT-IR measurement peak intensity is more preferably as follows.
(1) The peak in a region of $(1,085\pm50\ cm^{-1})$ (hereinafter referred to as a "peak 1") is a peak having the largest intensity among the measured IR spectrum and the peak having the second largest intensity exists in a region of $(1,411\pm50\ cm^{-1})$ when the intensity of a peak having the largest intensity denotes $I_0$ and this peak intensity is more preferably $(1/5)\times I_0$ or more (especially $(1/3)\times I_0$ or more).
(2) The peak in a region of $(1,411\pm50\ cm^{-1})$ (hereinafter referred to as a "peak 2") is a peak having the second largest intensity among the measured IR spectrum and the peak having the third largest intensity exists in a region of $(1649\pm50\ cm^{-1})$ when the intensity of a peak having the second largest intensity denotes $I_0$ and this peak intensity is more preferably $(1/5)\times I_0$ or more (especially $(1/3)\times I_0$ or more).
(Intensity of Other IR Peak)
Also in the above case, in the protein complex of the present invention, there is no particular limitation on IR peak other than the above-mentioned "peak 1" and "peak 2". The protein complex of the present invention may have a peak, for example, in the following region.
(Preferred Protein Complex)
The protein complex of the present invention preferably comprises at least protein and calcium. The protein complex preferably has an activity in catalyzing an asymmetric oxidation reaction. "Containing at least protein and calcium" and "Having an activity in catalyzing an asymmetric oxidation reaction" can be suitably confirmed by the below-mentioned method.
(Preferred Catalyst of Asymmetric Oxidation Reaction)
A preferred aspect of the asymmetric oxidation reaction of the protein complex of the present invention can be suitably represented by an optical purity (% ee) of R-1-octen-3-ol obtained when a substrate racemic-1-octen-3-ol (Matsutakeol) is reacted under the conditions of the below-mentioned Example 12. The protein complex of the present invention preferably gives R-1-octen-3-ol with a chemical yield of 85% or more under the conditions of Example 12. Furthermore, this optical purity is preferably 95% ee or more (especially 98% ee or less).
(Suitable Characteristics)
The protein complex of the present invention preferably has one or more characteristics among the following suitable characteristics.
(1) The protein complex shall further comprise a saccharide.
(2) The protein shall be a cross-linked crystallized protein
(3) The asymmetric oxidation reaction shall be an oxidation reaction which selectively gives one enantiomer of a substrate racemic alcohol.
(4) The protein complex shall have an activity which gives a deracemization reaction that allows ketone obtained by the asymmetric oxidation to undergo asymmetric oxidation.
(Estimated Mechanism of the Present Invention)
According to the discovery of the present inventors, it is estimated that a suitable protein complex derived from animal and plant is provided in the present invention for the following reason.
The crude protein derived from animal and plant as the inexpensive material is provided with a property wherein (i) an intermolecular disulfide bond (—S—S—) between cysteine residues (—SH) with each other in a protein, (ii) intermolecular aggregation (shortening of an intermolecular distance: <6.4 Å) in a protein and (iii) change of property into water solubility occur, and thus not only an active domain (Thioredoxin fold: Cys-X-Y-Cys sequences) is formed, but also a protein complex can be suitably eluted by shaking in warm water, by encapsulating in a calcium alginate gel capable of realizing the presence of a calcium salt and oxygen and then leaving to suitably stand in air (air oxidation).
The presence of a dissolved Ca salt and oxygen to be eluted in warm water has the effect of making a disulfide-bonded protein polymer (protein complex) easily dissolve in an aqueous solution, and they can easily be extracted by shaking in warm water. A point of an improvement in catalyst activity and an improvement in yield of a protein polymer (protein complex) lies in that the gel beads are suitably left to stand in air (air oxidation) and are easily "exudated" in the presence of low Ca ion concentration which dissolves in warm water.

The feature of the production method of the present invention lines in that a protein complex capable of acting in an enzyme-like manner is effectively produced at low cost in an environmentally friendly by "reversible idea" such as induction to a suitable disulfide bond, not by immobilization using a calcium alginate gel, utilizing characteristics of "protein complex formation" and "exudation" associated with air oxidation of animal and plant proteins.

(Relevant Documents of Estimated Mechanism)

Examples of support of the above-mentioned "estimated mechanism" of the present invention include the following documents.

In the document "Food and Technology", December, pp. 1-9 (2008) (Role of Table or Common Salt in Network Formation of Gluten Protein), "Reiko Urade; Graduate School of Agriculture, Kyoto University", it is known that a common or table salt and calcium chloride have the effect of changing the interaction of a gluten protein, to thereby change the property of gliadin and glutenin to the property of soluble in water (water solubility effect) and the effect of enhancing the interaction between gluten-constituting proteins, to thereby shorten an intermolecular distance (aggregation effect).

In the effect of shortening the intermolecular distance (aggregation effect), it is disclosed that the gluten intermolecular distance is 7.7 Å in case of adding no salt, while the intermolecular distance is shortened within 6.4 Å in case of adding a salt. Since the intermolecular distance between histidine and iron in an active domain of myoglobin mutant is 5.7 Å, the effect of designing appropriate arrangement of a functional amino acid residue of the active domain can also be expected as the aggregation effect by addition of a common or table salt. "Protein, Nucleic acid, Enzyme" 2004, November, Vol. 49, No. 14—Molecular Design of Metalloenzyme, Mainly Heme Enzyme—(Graduate School of Science, Nagoya University; Yoshihito Watanabe).

There is also reported that it causes a change in the interaction between protein molecules when the protein component (glutenin and gliadin) of a wheat flour dough is prepared in the presence of a common or table salt, and becomes soluble in pure water and exhibits insolubility in a saline solution.

Formation of a network structure of a glutenin polymer in wheat gluten is initiated by the addition of water to a wheat flour, and there is known a function of air oxidation wherein C-terminal and N-terminal cysteine residues of glutenin spontaneously form an intermolecular disulfide bond (R1-S-S—R2) using oxygen in air. However, latest reports (Non-Patent Document 7) "—Crystal structure of the DsbB-DsbA complex reveals a disulfide bond severation mechanism—Cell 127 789-801 (2006)" (Kenji Inaba et al.; Medical Institute of Bioregulation, Kyushu University) disclose that an enzyme for introducing a disulfide bond exists in *escherichia coli*, and an enzyme (DsbA) capable of oxidizing two cysteines of a substrate protein to form a disulfide bond and an enzyme (DsbB) capable of oxidizing the used DsbA to recover an oxidation capacity functions together with ubiquinone which is a substance involved in generation of activation energy in cells. It is known that electrons received by DsbB are donated to ubiquinone (UQ) which is a respiratory chain component and, finally, "oxygen becomes an electron acceptor" through cytochrome oxidase (see FIG. 11a and FIG. 11b).

Furthermore, a protein disulfide formation system of procaryote (*Escherichia coli*) is similar to that of eucaryotic cells (yeast endoplasmic reticulum, etc.) and Erolp exists as a functional homolog of DsbB in the vicinity of an endoplasmic reticulum membrane in endoplasmic reticulum. Oxidizability for creating a disulfide bond in an *Escherichia coli* system is "ubiquinone", whereas, it is flavin adenine dinucleotide (FAD) in an endoplasmic reticulum system. It is disclosed that a DsbA-DsbB-ubiquinone oxidation system in *Escherichia coli* and PDI-Erolp-FAD of eukaryote have a mutual relationship of a functional homolog (see FIG. 11a and FIG. 11b).

In addition, the disulfide bond is a chemical bond which is indispensable for a protein existing on a lot of cell cortex to exactly form and maintain conformation, and formation and dissociation of the disulfide bond exert an influence on activity of the prote wherein is important for a function of cells, and on existing position in cells, and cope with stress caused by a change in redox environment of cells.

STRUCTURE-FUNCTION STUDIES OF GLUTAREDOXINS AND RELATED OXIDOREDUCTASRE—] (Tobias H. ElGAn; From THE DEPARTMENT OF BIOSCIENCES AND NUTRITION Karolinska Institutet, Stockholm, Sweden) discloses that common sequence consisting of two cysteines "Thioredoxin fold (Cys-X-Y-Cys)" exist in an enzyme active domain and this site catalyzes formation of the disulfide bond and isomerization, and thus having a redox activity. A hydrophobic amino acid often exists on X and Y of Cys-X-Y-Cys. Cysteine residues become two free thiol groups in a reduction type, while they are linked through the disulfide bond in the oxidation type (see the below-mentioned FIG. 11a and FIG. 11b).

Components that account for about 70 to 80% of a wheat protein are classified into gliadin (band existing between 25 kda and 50 kda) such as albumin, globulin and wheat prolamin, and glutenin consisting of a high-molecular weight glutenin (three bands existing between HMW: 75 Kda and 150 kda) and a low-molecular weight glutenin (band existing between LMW: 25 Kda and 50 kda). SDS-page thereof is shown in FIG. 4.

(Targeted Catalyst Activity)

FIG. 12 shows various functions of enzymes formed by intracellular cysteine oxidation as known in the document "Biochemical and Biophysical Research Communications" 300, pp. 1-4 (2003) (Multiple roles of cysteine in biocatalysis) "Niroshini M, Giles et al; School of Chemistry, University of Exeyer". (1) Peptidase, (2) glyceraldehyde 3-phosphate dehydrogenase (GAPDH), (3) alcohol dehydrogenase (ADH), (4) bacterial nitrile hydratase (NHase), (5) ribonucleotide reductase (RNRase), (6) pyruvate formate lyase (PFL), (7) benzylsuccinate synthase (BSS), (8) reduction of glutathione disulfide (GSSG), (9) thioredoxin (Trx), (10) glutathion reductase (GR), (11) thioredoxin reductase (TR), (12) NADH oxidase (Nox), (13) NADH peroXidase (Npx).

As known in Japanese Patent No. 3,294,860 (a process for producing an optically active alcohol), the first step of extracting a water-soluble protein from grains or beans; the second step of encapsulating the protein in a calcium alginate gel; and third step of carrying out an asymmetric oxidation conversion reaction of a substrate using the encapsulated protein as a catalyst are disclosed. As known in Japanese Patent No. 3,683,129 (process for producing an optically active alcohol), the first step of extracting a water-soluble protein selected from egg white and ovalbumin separated from egg white; the second step of encapsulating the protein in calcium alginate; and third step of carrying out an asymmetric oxidation conversion reaction of a substrate using the encapsulated protein as a catalyst are disclosed.

These inventions differ from the present invention in (1) reference to an active domain formation mechanism in protein molecules to be constructed by air oxidation, and (2) development to a process for producing a powdered catalyst which can be stored at a normal temperature due to removal of moisture after cross-linking crystallization, in addition to the above discoveries.

The respective steps constituting the production method of the present invention will be described below.

(First Step)

In the extraction of the water-soluble protein in the first step of the present invention, grains or beans are crushed, large pieces and husks are removed and the grains and beans crushed powder obtained in this manner are extracted for 30 minutes or more in water equal to 7-15 times the weight of grains or beans at about 20 to 60° C., and preferably about 40° C., and a pH of about 6 to 8, and preferably pH of about 7.0. It is most effective to extract for about 45 minutes, and even if extracted for longer than this, the amount of extract does not change. When it is necessary to adjust pH, pH may be adjusted to the above-mentioned optimum range using a food-grade acid such as $H_2SO_4$, HCl, $H_3PO_4$ or a food-grade alkali such as NaOH. The above-mentioned water-soluble protein extract or protein curd obtained by separating food fiber components from this extract by decanting or centrifugal separation, is either transferred to the second step as it is, or transferred to the second step after forming into a powder by spray drying, freeze-drying or vacuum-drying and then redissolving as necessary. Seeds (husks (brans, rice brans) and germs (sprouts)) can be obtained by the step of the grains and beans crushed powder. Husks (brans, rice brans), germs (sprouts), leaves (young leaves, sprouts), stems, roots and flowers are dried by freeze-drying (FD), hot-air drying (AD), vacuum-drying and the like, to thereby remove moisture, followed by finely crushing up to 5 µm or less using a ball mill and the like.

The obtained crushed powder can be transferred to the second step as it is. The object of selecting the pH of isoelectric point precipitation is to select the fraction having the largest precipitated amount, and the pH is in the vicinity of 4.5 and 9.5 in case of soy bean, and green pea and buckwheat protein. 5 to 10 times by weight of water are added to this curd, followed by crushing using a mixer or a stirrer, to thereby prepare a protein slurry, followed by neutralization (pH 6 to 8), to thereby obtain a neutral slurry. After converting this slurry into a powder by spray-drying, freeze-drying (FD) or vacuum-drying in the same manner as descried above, the powder is redissolved and transferred to the second step.

However, when it is necessary to treat a large amount of protein, the protein curd is subjected to an isoelectric point treatment using a food-grade acid such as $H_2SO_4$, HCl or $H_3PO_4$, or a food-grade alkali such as NaOH, followed by separation of the whey by decanting or centrifugal separation, to thereby obtain a protein curd. This isoelectric precipitation is performed for the purpose of concentrating of a water-soluble protein, and the same effects as in case of forming into a powder by spray-drying of a water-soluble protein extract, as it is, are exerted even after the treatment.

(Second Step)

In the second step, the process for encapsulating the extracted protein includes, for example, an encapsulating method wherein the extracted protein is either incorporated in the fine matrix of a gel such as alginate, starch, konjak, a polyacrylamide gel or a gel of polyvinyl alcohol (matrix type) or coating with a semi-permeable coating (microcapsule type). However, in case of producing a protein complex, an encapsulating method using calcium of alginic acid extracted from kelp is most preferred since it is inexpensive and environmentally friendly, and it is easy to perform an encapsulating operation. The encapsulated beads require a warm water temperature of 30° C. to 45° C. so as to elute the protein complex in aqueous solution, and also require oxygen supply so that the dissolved oxygen concentration becomes zero. Also, it is desired to shake at a rotation speed which enables shaking of beads.

(Third Step)

In the third step, in order to allow the protein to undergo crystallization precipitation, ammonium sulfate, polyethylene glycol (PEG), polyethylene glycol/lithium chloride, 2-methyl-2,4-pentadiol, sodium chloride, sodium malonate and the like are exemplified, and any compound can be used as a crystallization precipitant in the present invention. However, it is most advantageous to use inexpensive ammonium sulfate from the viewpoint of total cost down. It is desired to crystallize the protein using a protein solution which has a concentration of 10 to 50 mg/mL, and also there is a method of concentration a sample using Centricon, Amicon Ultra and the like.

(Fourth Step)

In the fourth step, in order to cross-link the crystallized precipitated protein, glutaraldehyde (hereinafter may be sometimes abbreviated to "GA"), formaldehyde (hereinafter may be sometimes abbreviated to "FA") and the like are exemplified, and any compounds can be used as a cross-linking agent in the present invention. Glutaraldehyde is an organic compound represented by the rational formula $OHC(CH_2)_3CHO$, and reacts with an ε-amino group as a lysine residue of the protein, and also reacts with an α-amino group or an SH group, and thus an intermolecular cross-link can be formed. It is not considered that one glutaraldehyde molecule alone can causes cross-link formation. (Reference document; supervised by Yoshinobu Shigenaka, "Observation of Protozoan and Test Method (i.e, Genseidoubutu-no-Kansatus-to-Jikken Houhou)" (Kyoritsu Shuppan Co., Ltd., 1998) ISBN 4320053532). GA have two aldehyde groups and FA has one aldehyde group, and it becomes possible to be widely utilized as an industrial enzyme reagent in a practical level by cross-linking, for example, (1) it is stable at room temperature for a long period (one or more years), (2) it is substantially 100% active protein (high volume measurement (volumetric) and catalyst productivity), (3) it is easy to recover and recycle, (4) it has high temperature stability and high resistance to an organic solvent as compared with an enzyme alone, and (5) it has high activity and selectivity as compared with an enzyme alone.

Since GA may have two aldehyde groups, it has a very strong immobilizing force as compared with FA. While GA has a strong immobilizing force, it has a drawback such as a very low penetration rate. Since FA has a weak immobilizing force but shows a penetration rate which is several times higher than that of GA, it is possible to make up for mutual weak points by mixing a GA immobilization liquid with FA. A GA/FA mixed immobilizing liquid was devised by Karnovsky (1965) (5% GA+4% FA), and name of Karnovsky is known as "use of dilute Karnovsky" still now. In addition to CA and FA, various additives may be sometimes added in the immobilizing liquid. Most occasionally, sucrose, glucose, table or common salt and the like can be added so as to adjust (increase) an osmotic pressure. With respect to the immobilization time by means of cross-linking, in case of using a bulk (1 mM or more in thickness), about 2 hours is a minimum time. The temperature of the immobilizing liquid can vary, for example, immobilizing is carried out at room temperature or 4° C. (ice water). With respect to reproducibility as important, immobilization is preferably carried out at a normal temperature of from 20° C. to 40° C. When a given temperature is required, the temperature can be maintained at about 4° C. by immersing s sample bottle containing an immobilizing liquid and a sample in water with floating ice. Taking a total operation cost or the like into consideration, it is preferred to immobilize at a normal temperature of 20° C. to 40° C. After immobilization, residual TA and FA can be washed with 0.1 M phosphoric acid buffer (about 220 mOsm), or a solution prepared by adding a 0.1-0.2 M sucrose or glucose to the buffer thereof.

(Fifth Step)

In the fifth step, in order to form into a powder by drying, it is possible to use (1) hot-air drying (AD), (2) freeze-drying (FD), (3) press drying, (4) compression-drying, (5) air drying and the like in the present invention. However, freeze-drying (FD) enables complete removal of moisture, and is advantageous for the subsequent crushing step and also enhances storability.

(Description of Respective Data)

The respective data shown in the drawings will be described below.

Figure 1:
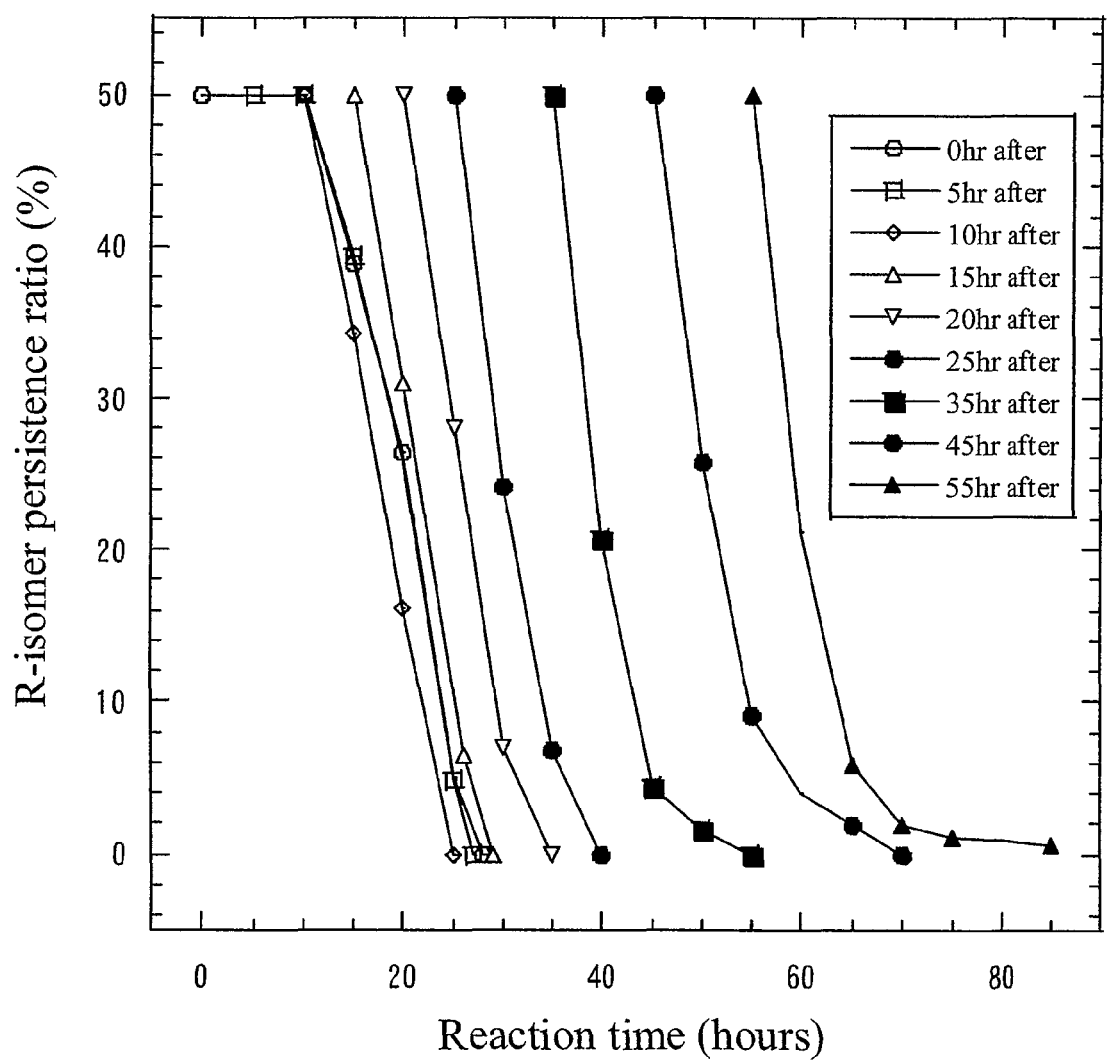
FIG. 1 is a graph showing a persistence ratio of a substrate when distilled water is added to a green pea protein-calcium alginate gel beads, and a substrate R-1-(2-naphthyl)ethanol is added at a predetermined time after initiation of shaking in the second step of the production method of the present invention.

FIG. 1 shows a persistence ratio of a substrate when distilled water is added to green pea protein-calcium alginate gel beads and a substrate (racemic)-1-(2-naphthyl)ethanol is added at 0 hours, 5 hours, 10 hours, 15 hours, 20 hours, 25 hours, 35 hours, 45 hours and 55 hours after initiation of blank shaking in the second step.

Figure 2A:
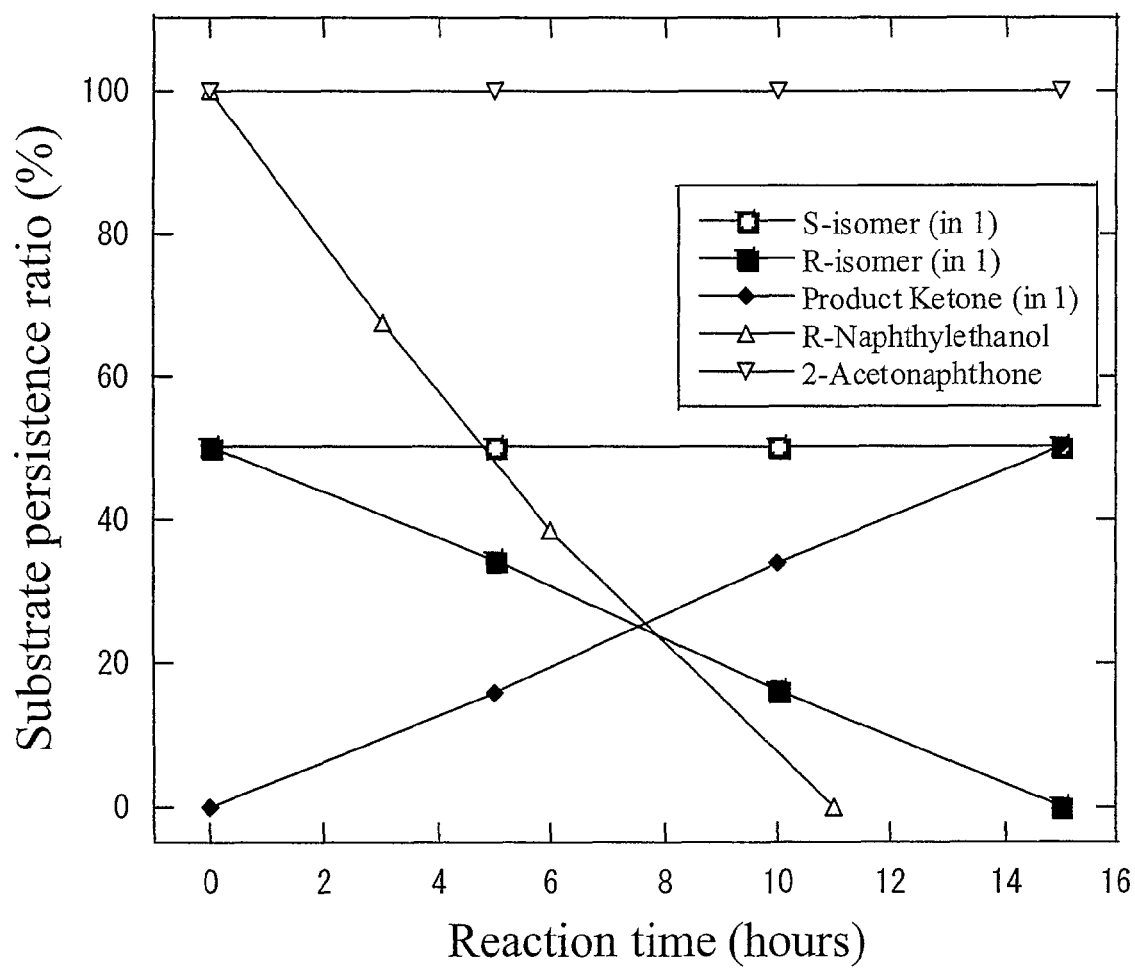
FIG. 2a is a graph wherein a ratio (%) of a substrate to a product with a reaction time is monitored when various substrates are added at 10 hours after blank shaking in the second step of the production method of the present invention.

FIG. 2a is a graph wherein a ratio (%) of a substrate to a product with a reaction time is monitored when (a) substrates racemic 1-(2-naphthyl)ethanol, R-1-(2-naphthyl)ethanol, 2-acetonaphthone are added in each amount of 50 mg at 10 hour after blank shaking in the second step.

Figure 2B:
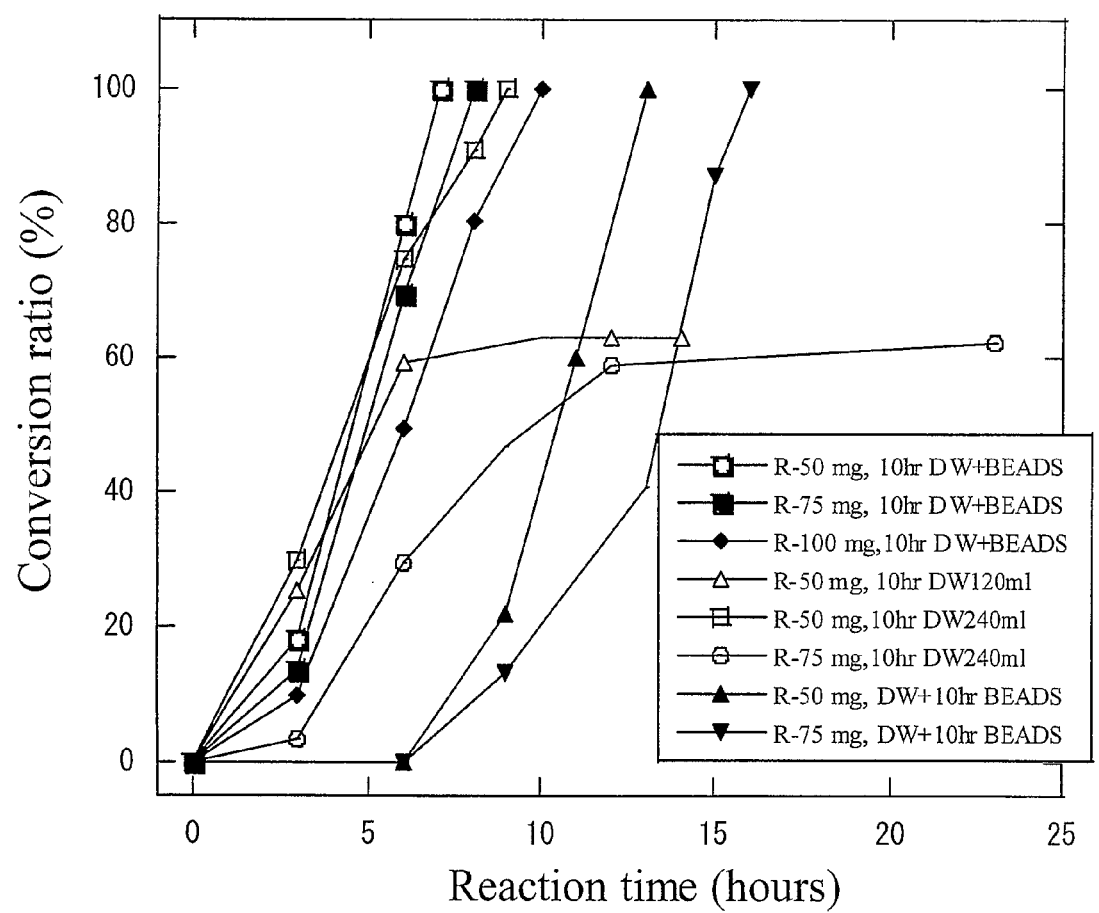
FIG. 2b is a graph wherein a substrate R-1-(2-naphthyl) ethanol is added to an aqueous solution or the like at 10 hours after blank shaking and then an amount (%) of the formed ketone is monitored in the second step of the production method of the present invention.

FIG. 2b is a graph wherein a substrate R-1-(2-naphthyl) ethanol (50 mg, 75 mg or 100 mg) is added to an aqueous solution (120 ml, 240 ml) at 10 hours after blank shaking, beads+distilled water (DW 120 ml) at 10 hours after blank shaking, and new beads+aqueous solution (120 ml) at 10 hours after blank shaking, respectively, and then an amount (%) of the formed ketone is monitored in the second step.

FIG. 2c is a graph wherein green pea-calcium alginate gel beads prepared by added dropwise in a different concentration (5 g/L, 7.5 g/L, 10 g/L, 15 g/L, 20 g/L, 30 g/L) of calcium chloride is blank-shaken for 10 hours and then reacted with a substrate R-1-(2-naphthyl)ethanol, and a protein complex activity is examined in the second step.

Figure 2D:
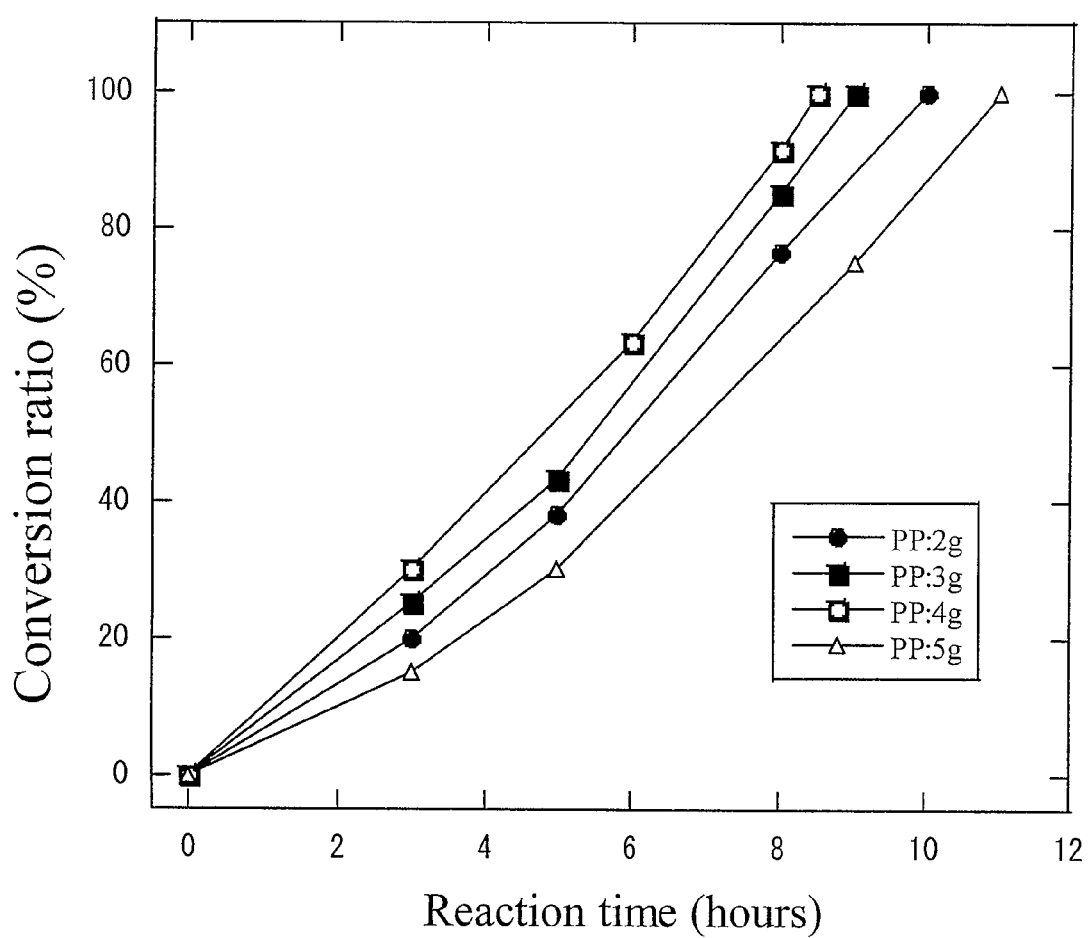
FIG. 2d is a graph wherein green pea-calcium alginate gel beads are prepared in a predetermined mass of a green pea protein and blank-shaken for 10 hours and then and a substrate R-1-(2-naphthyl)ethanol (50 mg) is respectively added and a protein complex activity is examined in the second step of the production method of the present invention.

FIG. 2d is a graph wherein green pea-calcium alginate gel beads are prepared by 2 g, 3 g, 4 g and 5 g of a green pea protein and blank-shaken for 10 hours and then and a substrate R-1-(2-naphthyl)ethanol (50 mg) is added and a protein complex activity is examined in the second step.

Figure 3:
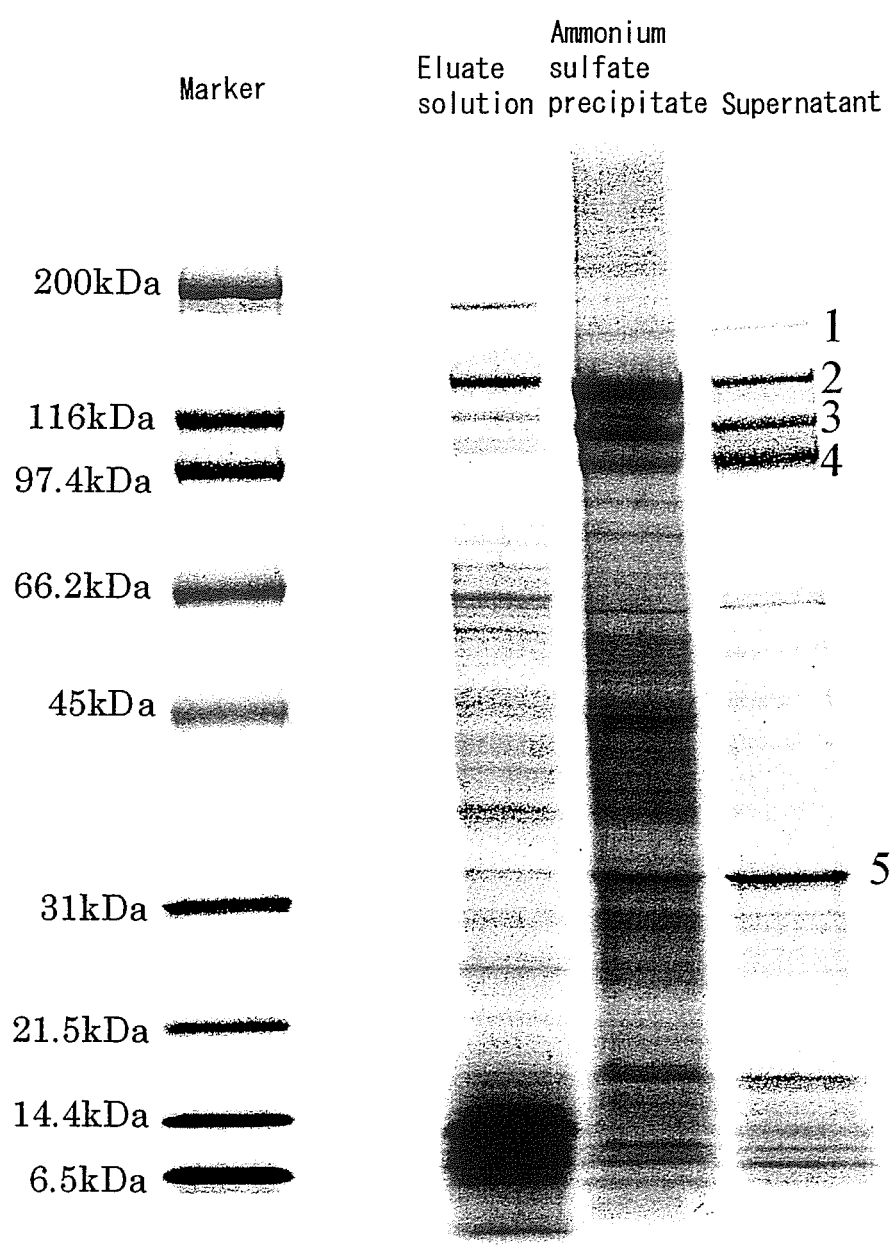
FIG. 3 shows determination of a molecule weight of water-soluble protein component (SDS-page) obtained by shaking a green pea-Ca alginic acid gel in warm water for 10 hours or more and then allowing the eluted protein complex to undergo crystallization precipitation with ammonium sulfate 30%.

FIG. 3 is a drawing wherein a protein complex obtained by shaking a green pea-Ca alginic acid gel in warm water for 10 hours or more is allowed to undergo crystallization precipitation at ammonium sulfate 30% and is further subjected to centrifugal separation (15 minutes, 10,000 rpm), to thereby obtain a precipitate, which is then subjected to SDS-page.

SDS-Page

A sample (10 μL) was mixed with 10 μL of 2× sample buffer (0.1 M tris/HCl pH 6.8, 3% SDS, 10% glycerin, 10% β-mercaptoethanol, 0.1% BPB), followed by heating at 100° C. for 5 minute. The obtained mixture was subjected to electrophoresis (constant current: 18 mA, electrophoresis buffer: 25 mM Tris/HCl, 0.19 M Glycine, 0.1% SDS, pH 8.3), together with a molecular weight marker (SDS-PAGE Standard Broad, Bio-Rad), using SDS-PAGE mini (4-20% Gradient gel, TEFCO Co., Ltd.), and then subjected to CBB staining (PHastGel Blue R, Amersham Biosciences Corp.).

FIG. 4 is extract of "FIG. 5; Influence of Addition of table or common salt on cross-linking efficiency by DST" described in the document "Food and Technology" December, pp. 1-9 (2008) (Role of Table or Common Salt in Network Formation of Gluten Protein)) "Reiko Urade; Graduate School of Agriculture, Kyoto University" (hereinafter, an explanatory text is mentioned). A dough with or without addition of a common or table salt was treated with DST, and then a protein was solubilized with an SDS solution containing β-mercaptoethanol. The solubilized liquid was ultracentrifuged, to thereby separate into a soluble fraction (S) and an insoluble fraction (P). The insoluble fraction was treated with sodium metaperiodate. Each sample was separated by SDS polyacrylamide gel electrophoresis and the protein was stained.

FIG. 5 shows the results analyzed by cross-linked crystallized powders ((V) and (vi)), which is obtained by preparing a green pea protein powder (i), a sodium alginate powder (ii) and a preparing green pea protein-calcium alginate gel in accordance with a usual method, omitting (iii) shaking by a constant-temperature shaking incubator, or (iv) protein complex powders ((iii) and (iv)) prepared by stirring in jar fermentor warm water, and the second encapsulating step in the second step, and allowing the green pea protein (i) to undergo constant-temperature shaking (55 rpm, 40° C., 24 hours) in 2% calcium chloride/50 mM Tris HCl buffer ((V) pH 6.0 or (vi) pH 8.0), by FT-IR.

Infrared spectroscopy (FT-IR) was measured at frequency resolution of 8 $cm^{-1}$ and integration times of 39 times by a Micro-ATR method (Ge crystal), using Fourier transform infrared spectrophotometry Magna-750 and an infrared microscope Nic-Plan manufactured by Thermo Fisher Scientific.

In FIG. 5, symbols A to E have the following meanings.
A: vicinity of 1,649 $cm^{-1}$; a peak peculiar to a peptide bond (—C(=O)—N—)
B: vicinity of vicinity of 1,528 $cm^{-1}$; a peak peculiar to a peptide bond (—C(=O)—N)
C: vicinity of 1,411 $cm^{-1}$; a peak peculiar to a ketone group of carboxylate (—C(=O)—O—Na)
D: vicinity of 1,122 $cm^{-1}$ (1,085 $cm^{-1}$, 1,032 $cm^{-1}$); a peak peculiar to a sugar ether (—C—O—C—)
E: vicinity of 1,085 $cm^{-1}$; a peak peculiar to a ammonium sulfate (($NH_4$)$_2SO_4$)

FIG. 6 show the results wherein a protein complex powder (i) prepared by constant-temperature shaking incubation, cross-linked crystallized powders ((ii) and (iii)) obtained from a green pea protein and a 9% calcium chloride/50 mM Tris HCl buffer solution ((ii) pH 6.0 or (iii) pH 8.0), and a green pea protein powder (iv) are subjected to X-ray microanalyzer qualitative analysis, using the same sample as in FIG. 5. X-ray microanalyzer analysis was carried out after coating a surface of a sample with gold, using EPMA-1600 manufactured by Shimadzu Corporation.

In FIG. 6, the respective samples have the following meanings.
Sample (i): cross-linked crystallized protein complex produced by shaking incubator
Sample (ii): 20 mM Ca chloride/50 mM Tris HCl buffer (pH 60)

Samples (iii): 20 mM Ca chloride/50 mM Tris HCl buffer (pH 8.0)

Sample (iv): green pea protein powder

FIG. 7 is a drawing showing an asymmetric oxidation activity intensity (right axis) after 6 hours of samples obtained by leaving beads encapsulated in a calcium alginate gel to stand in air for 0 hour, 0.5 hour, 1 hour, 3 hours, 5 hours, 7 hours, and then shaking in warm water, to thereby extract a protein complex in the second step, subjecting the protein complex to cross-linking crystallization, and then freeze-drying the protein complex, to thereby form into a powder, and a yield (left axis) of the obtained protein complex.

FIG. 8 is GC chromatogram of a perfume R-1-octen-3-ol having an optical purity of 98.2% ee, synthesized by encapsulating green pea-calcium alginate gel beads under the same conditions as in FIG. 1 and eluting an aqueous protein complex solution at 10 hours after shaking in the second step, and reacting the aqueous protein complex solution with a substrate racemic 1-octen-3-ol (Matsutakeol).

FIG. 9*a* to FIG. 9*h* (and Table (1)) are drawings and table wherein DO (concentration of dissolved oxygen) and pH monitoring drawing involved in whether or not oxygen is supplied in a green pea protein powder (1 kg)-calcium alginate gel (20 L in total) and addition of water (20 L) using a 100 L jar fermentor, and yield and activity of the obtained protein complex are summarized.

FIG. 9*a* and FIG. 9*b*: Results of first test
FIG. 9*c* and FIG. 9*d*: Results of second test
FIG. 9*e* and FIG. 9*f*: Results of third test
FIG. 9*g* and FIG. 9*h*: Results of fourth test

TABLE 1

| Number of extraction | Once | Twice | Three times | Four times |
|---|---|---|---|---|
| Reaction time (hour) | 72 | 48 | 24 | 24 |
| DO control (mg/L) | None | None | 0.25 mg/L | 0.25 mg/L |
| Turbidity (NTU) | 93.3 | 292 | 425 | 164 |
| Crude yield (g) | 16.2 | 34.2 | 46.9 | 26.2 |
| Yield amount after FD (g) | 5.24 | 10.05 | 13.06 | 6.15 |
| Concentration of Ca (mg/g) | 0.53 | 0.67 | 0.66 | 0.54 |
| Asymmetric oxidation activity | C | C | B | B |

(Explanation)
Concentration of Ca (FD): The results of the measurement of the concentration of Ca (mg/g) by an acid decomposition method of a sample after FD drying using an atomic absorption photometer.
C: Only an R-isomer of a racemic 1-(2-naphthyl)ethanol (10 ppm, 40 ml) solution is scarcely asymmetrically oxidized by a "protein complex" (350 mg) within 20 hours (the formed ketone is 10% or less).
B: Asymmetrically oxidation of only an R-isomer of a racemic 1-(2-naphthyl)ethanol (10 ppm, 40 ml) solution is stopped during asymmetric oxidation by a "protein complex" (350 mg) until 20 hours (the formed ketone is 30% or less).
A: Only an R-isomer of a racemic 1-(2-naphthyl)ethanol (10 ppm, 40 ml) solution is asymmetrically oxidized by a "protein complex" (350 mg) within 20 hours (the formed ketone is 40% or more).

FIG. 10 is a process chart of a production flow of a protein complex.

FIG. 11*a* shows an intracellular system for formation of a disulfide bond in procaryote (*Escherichia coli*).

FIG. 11*b* shows an intracellular system for formation of a disulfide bond in eucaryote (yeast endoplasmic reticulum).

FIG. 12 is a drawing showing kinds and enzymatic function (reactivity) of a sulfide-based enzyme obtained by cysteine oxidation in cells.

(Protein Complex Having Activity which Catalyzes Asymmetric Oxidation Reaction)

The protein complex of the present invention is characterized in that it is a product which is formed by air oxidation of a crude protein derived from animal and plant, and also has an enzyme-like activity which catalyzes an asymmetric oxidation reaction.

(Process for Measurement of Asymmetric Oxidation Activity)

The activity of the protein complex, which catalyzes an asymmetric oxidation reaction of the present invention can be suitably measured, for example, by the method described hereinafter (6. Asymmetric Oxidation Activity in Example 15 "Conditions of Extracting Operation").

(Process for Purification of Protein Complex)

In the present invention, there is no particular limitation on the process for purification of a protein complex. For the purpose of increasing a yield of the protein complex, filtration is not required. However, glass beads can be used so as to separate from calcium alginate gel beads. In this case, the diameter can be from 40 to 200 μm, and preferably 200 μm.

The present invention will be described specifically below by way of Examples, but it should be understood that these are exemplary of the invention and are not to be considered as limiting.

EXAMPLE 1

(General Process for Producing Cross-Linked Crystallized Protein Complex Derived from Green Pea)

First, in the first step, green peas are crushed, to thereby remove husks, and a green pea protein component dissolved for about 45 minutes in 9 times by weight of distilled water (about 40° C.) at the pH of about 7.0 is adjusted to pH 7.0 using an aqueous NaOH solution. The food fiber of the precipitated component is removed and the protein is subjected to isoelectric point precipitation by bringing the water-soluble protein portion to alkali conditions (about pH 9.5) or acidic conditions (about pH 4.5). After redissolving the protein precipitate moiety with distilled water at pH 7.0, a spray-drying treatment is performed on the resulting aqueous green pea protein solution (sample concentration: 5.0%) to prepare powdered green pea protein. In addition, an aqueous 3% sodium alginate solution is prepared by dissolving sodium alginate in aqueous solution under autoclave conditions and temperature of 121° C. for 20 minutes.

Next, in the second step, 200 ml of distilled water corresponding to 10 times the equivalent weight are added to 20 g of a green pea protein powder, followed by the addition of 200 ml of an aqueous 3% sodium alginate solution corresponding to 1.0 times the equivalent weight and stirring until uniform. The resulting green pea-sodium alginate mixed solution is added dropwise in an aqueous 4% calcium chloride solution, to thereby prepare green pea protein-containing calcium alginate gel beads in an immobilized state. The beads were left to stand in air for 5 hours. The green pea protein-containing calcium alginate gel beads was washed with distilled water, to thereby remove an aqueous calcium chloride solution, and distilled water (400 ml) corresponding to 20 times the equivalent weight of the used green pea protein powder was added as an extract solution. Constant-temperature shaking incubation (40° C., 55 rpm) was carried out for 2 days and the water-soluble fraction was separated and recovered, and then beads were further shaken for one day, to thereby recover the objective solution in the same manner. After shaking for additional one day, the objective solution can be separated and recovered. The protein complex comprised in the recovered reaction solution was subsequently allowed to undergo crystallization precipitation in the third step.

In the third step, the separated and recovered solution was adjusted to saturated 30% ammonium sulfate for the purpose of precipitation of a slightly water-soluble component, and then left to stand for 20 hours or more. The protein complex was not only eluted easily from beads in the presence of calcium chloride, but also it became water insoluble in the presence of a saturated 30% ammonium sulfate solution and then aggregated and precipitated.

In the fourth step, a commercially available 25% glutaraldehyde solution was further added to the precipitated and aggregated crystallized protein complex so that the concentration of the solution becomes 0.25%, and the solution was left to stand for 2 hours or more (preferably 10 hours or more). The obtained protein complex could be easily separated from the solution by decantation using a cold centrifuge (10,000 rpm, 15 min, 10° C.).

In the fifth step (freeze-drying (FD)), the protein complex of the precipitate was cooled to −50° C. and left to stand for 1 hour. After adjusting to a vacuum state of about 0.1 mbar or less, the temperature was raised from 50° C. to 50° C., to thereby cause sublimation and removal of moisture. A series of required FD time was about 20 hours.

In the sixth step, the protein complex wherein moisture could be removed by freeze-drying (FD) could be converted into a powdered catalyst capable of being stored at normal temperature by the subsequent ball mill crushing.

EXAMPLE 2

(Examination of Substrate Specificity of Protein Complex Derived from Green Pea Protein (PP), Soy Bean Protein (SP) and Wheat Protein (WP) in Second Step)

In the second step, with respect to a crude protein derived from green pea protein (PP), soy bean protein (SP) and wheat protein (WP), seeds are crushed and water is added. After 1 hour, a bean curd lee fraction of the precipitate is removed and an aqueous solution fraction is spray-dried, to thereby obtain 20 g of a powder. In accordance with a usual method, 200 ml of distilled water corresponding to 10 times the equivalent weight is added and 200 ml of an aqueous 3% sodium alginate solution is added corresponding to 1 time the equivalent weight, followed by stirring until uniform. The obtained green pea-sodium alginate mixed solution is added dropwise in an aqueous 4.0% calcium chloride solution, to thereby obtain green pea protein-containing calcium alginate gel beads. To the thus obtained beads, distilled water (400 ml) of a green pea protein powder corresponding to 20 times the equivalent weight is added as the reaction solution. After shaking for 10 hours or more using a constant-temperature shaking incubator under the conditions of a temperature setting of 40° C. and the number of shaking of 55 rpm, a substrate conversion reaction was carried out. As the substrate, 1-(2-naphthyl)ethanol (naphthyl/1) and phenylethanol wherein chlorine (Cl-/2a, 2b), bromine (Br-/3a, 3b), fluorine (F-/4a, 4b), methyl (Me-/5a, 5b), methoxy (MeO-/6a, 6b) and nitro (NO2-/7a, 7b) are substituted on the meta- and para-positions were used. As a result, the reaction time, product, optical purity and chemical yield are summarized in the table below.

(Substrate Specificity of Meta-Substituted Substrate of Protein Complex Derived from Green Pea Protein (PP), Soy Bean Protein (SP), Wheat Protein (WP) in Second Step)

TABLE 2

(Substrate Specificity of Meta-Substituted Substrate of Grains - Beans Proteins in Second Step)

| | Substrate (±)-ArCH(OH)R | | Reaction time | Plant origin | Products | | |
|---|---|---|---|---|---|---|---|
| | Ar | R | | | Comp | OP/% e.e. | CY/% |
| 1 | 2-Naphthyl | Me | 15 | PP | S-1 | ≥99 | 50 |
| 2a | 3-ClC6H4 | Me | 24 | PP | S-2a | ≥99 | 50 |
| 3a | 3-BrC6H4 | Me | 36 | PP | S-3a | ≥99 | 49 |
| 4a | 3-FCC6H4 | Me | — | PP | Not resolved! | | |
| 5a | 3-MeC6H4 | Me | 29 | PP | S-5a | ≥99 | 50 |
| 6a | 3-MeOC6H4 | Me | 36 | PP | S-6a | ≥99 | 50 |
| 1 | 2-Naphthyl | Me | 25 | SP | S-1 | ≥99 | 49 |
| 2a | 3-ClC6H4 | Me | 25 | SP | S-2a | ≥99 | 50 |
| 3a | 3-BrC6H4 | Me | 25 | SP | S-3a | ≥99 | 49 |
| 4a | 3-FCC6H4 | Me | — | SP | Not resolved! | | |
| 5a | 3-MeC6H4 | Me | 45 | SP | S-5a | ≥99 | 50 |
| 6a | 3-MeOC6H4 | Me | 30 | SP | S-6a | ≥99 | 50 |
| 1 | 2-Naphthyl | Me | — | WP | Not resolved! | | |
| 2a | 3-ClC6H4 | Me | 25 | WP | S-2a | ≥99 | 49 |
| 3a | 3-BrC6H4 | Me | 18 | WP | S-3a | ≥99 | 50 |
| 4a | 3-FCC6H4 | Me | 76 | WP | S-4a | ≥99 | 50 |
| 5a | 3-MeC6H4 | Me | 38 | WP | S-5a | ≥99 | 49 |
| 6a | 3-MeOC6H4 | Me | 53 | WP | S-6a | ≥99 | 50 |

Supplement: Comp: compound, OP/% e.e.: optical purity, CY/%: chemical yield

As is apparent from the above results, a protein complex derived from green pea protein (PP), soy bean protein (SP) and wheat protein (WP) was suitably eluted from a gel and, at the same time, an R-isomer of racemic phenyl ethanols of meta-substituted chlorine (Cl-/2a), bromine (Br-/3a), fluorine (F-/4a), methyl (Me-/5a), methoxy (MeO-/6a) and nitro (NO2-/7a) as the substrate was selectively oxidized, and an S-isomer alcohol was obtained with a chemical yield of about 50 and an optical purity of 99% e.e. or more.

(Examination of Substrate Specificity of Para-Substituted Substrate of Protein Complex Derived from Green Pea Protein (PP), Soy Bean Protein (SP) and Wheat Protein (WP) in Second Step)

TABLE 3

(Substrate Specificity of Para-Substituted Substrate of Grains - Beans Proteins in Second Step)

| | Substrate (±)-ArCH(OH)R | | Reaction time | Plant origin | Products | | |
|---|---|---|---|---|---|---|---|
| | Ar | R | | | Comp | OP/% e.e. | CY/% |
| 2b | 4-ClC6H4 | Me | 15 | PP | S-2b | ≥99 | 50 |
| 3b | 4-BrC6H4 | Me | 24 | PP | S-3b | ≥99 | 50 |
| 4b | 4-FC6H4 | Me | 20 | PP | S-4b | ≥99 | 50 |
| 5b | 4-MeC6H4 | Me | 19 | PP | S-5b | ≥99 | 49 |
| 6b | 4-MeOC6H4 | Me | 19 | PP | S-6b | ≥99 | 50 |
| 7b | 4-NO2C6H4 | Me | 45 | PP | S-7b | ≥99 | 50 |
| 2b | 4-ClC6H4 | Me | 19 | SP | S-2b | ≥99 | 50 |
| 3b | 4-BrC6H4 | Me | 19 | SP | S-3b | ≥99 | 49 |
| 4b | 4-FC6H4 | Me | 34 | SP | S-4b | ≥99 | 50 |
| 5b | 4-MeC6H4 | Me | 25 | SP | S-5b | ≥99 | 50 |
| 6b | 4-MeO6H4 | Me | 18 | SP | S-6b | ≥99 | 50 |
| 7b | 4-NO2C6H4 | Me | 30 | SP | S-7b | ≥99 | 50 |
| 2b | 4-ClC6H4 | Me | 23 | WP | S-2b | ≥99 | 50 |
| 3b | 4-BrC6H4 | Me | 29 | WP | S-3b | ≥99 | 50 |
| 4b | 4-FC6H4 | Me | 18 | WP | S-4b | ≥99 | 50 |
| 5b | 4-MeC6H4 | Me | 29 | WP | S-5b | ≥99 | 50 |
| 6b | 4-MeO6H4 | Me | 15 | WP | S-6b | ≥99 | 50 |
| 7b | 4-NO2C6H4 | Me | | WP | Not resolved! | | |

Supplement: Comp: compound, OP/% e.e.: optical purity, CY/%: chemical yield

As is apparent from the above results, a protein complex derived from green pea protein (PP), soy bean protein (SP) and wheat protein (WP) was suitably eluted from a gel and, at the same time, an R-isomer of racemic phenyl ethanols of a para-substituted chlorine (Cl-/2b), bromine (Br-/3b), fluorine (F-/4b), methyl (Me-/5b), methoxy (MeO-/6b) and nitro (NO2-/7b) as the substrate was selectively oxidized, and an S-isomer alcohol was obtained with a chemical yield of 50 and an optical purity of 99% e.e. or more.

EXAMPLE 3

(Examination of Substrate Specificity of Protein Complex Derived from Tissue Material Derived from Other Plants in Second Step)

In the second step, for the purpose of confirming elution of an activity of a protein complex, which catalyzes an asymmetric oxidation reaction from seeds, leaves, stems, roots, flowers and fruits of grasses and weeds such as young wheat leaves (YWL), young barley leaves (YBL), *Artemisia vulgaris* indica (AVI) leaves, wheat brans (WB), wakame (Undaria) (WS), carrot (C) and pumpkin (P) further included therein, these grasses and weeds were washed by immersing in warm water at 60° C. or more for 10 minutes, optionally sliced thinly, freeze-dried (FD) and then finely crushed using a ball mill. In accordance with a usual method, 200 ml of distilled water corresponding to 10 times the equivalent weight was added to 20 g of these plant material powders, and 200 ml of an aqueous 3% sodium alginate solution corresponding to 1 time the equivalent weight was added, followed stirring until uniform. The obtained plant tissue-containing sodium alginate mixed solution was added dropwise in an aqueous 4.0% calcium chloride solution, to thereby obtain plant tissue-containing calcium alginate gel beads. To the beads, distilled water (400 ml) corresponding to 20 times the equivalent weight of the plant tissue-containing powder was added as the reaction solution. After shaking for 10 hours or more under the conditions of constant-temperature shaking temperature setting of 40° C. and the number of shaking of 55 rpm, a substrate conversion reaction was carried out. As the substrate, phenylethanols wherein bromine (Br-/1m, 1p), chlorine (Cl-/2m, 2p), fluorine (F-/3m, 3p), methyl (Me-/4m, 4p), methoxy (MeO-/5m, 5p) and 1-(2-naphthyl)ethanol (naphthyl/6) have been substituted on the meta- and para-positions were reacted. With respect to the obtained results, the reaction time, product, optical purity and chemical yield are summarized in the table below.

(Examination of Substrate Specificity of Meta-Substituted Substrate of Protein Complex Derived from Young Wheat Leaves, Young Barley Leaves and Wheat Brans in Second Step)

TABLE 4

(Substrate Specificity of Meta-Substituted Substrate of Protein Complex derived from Young Wheat Leaves, Young Barley Leaves and Wheat Brans in Second Step)

| Substrate | | Reaction time | Plant origin | Products | | |
|---|---|---|---|---|---|---|
| | Ar | | | Comp | OP/% e.e. | CY/% |
| 1m | 3-BrC6H4 | 14 | YWL | S-1m | ≥99 | 50 |
| | 3-BrC6H4 | 12 | YBL | S-1m | ≥99 | 50 |
| 2m | 3-ClC6H4 | 26 | YWL | S-2m | ≥99 | 50 |
| | 3-ClC6H4 | 31 | YBL | S-2m | ≥99 | 50 |

TABLE 4-continued (Substrate Specificity of Meta-Substituted Substrate of Protein Complex derived from Young Wheat Leaves, Young Barley Leaves and Wheat Brans in Second Step)

| Substrate | | Reaction time | Plant origin | Products | | |
|---|---|---|---|---|---|---|
| | Ar | | | Comp | OP/% e.e. | CY/% |
| 3m | 3-FC6H4 | 85 | WB | S-3m | ≥99 | 50 |
| | 3-FC6H4 | 34 | YBL | S-3m | ≥99 | 50 |
| 4m | 3-MeC6H4 | 39 | WB | S-4m | ≥99 | 50 |
| | 3-MeC6H4 | 26 | YWL | S-4m | ≥99 | 50 |
| | 3-MeC6H4 | 49 | YBL | S-4m | ≥99 | 50 |
| 5m | 3-MeOC6H4 | 63 | WB | S-5m | ≥99 | 50 |
| | 3-MeOC6H4 | 26 | YWL | S-5m | ≥99 | 50 |
| | 3-MeOC6H4 | 29 | YBL | S-5m | ≥99 | 25 |
| 6 | 2-naphthyl | 12 | YWL | S-6 | ≥99 | 50 |
| | 2-naphthyl | 10 | YBL | S-6 | ≥99 | 50 |

Supplement: Comp: compound, OP/% e.e.: optical purity, CY/%: chemical yield

As is apparent from the above results, a protein complex derived from young wheat leaves (YWL), young barley leaves (YBL) and wheat brans (WB) was suitably eluted from the gel and, at the same time, an R-isomer of racemic phenyl ethanols of meta-substituted bromine (Br-/1m), chlorine (Cl-/2m), fluorine (F-/3m), methyl (Me-/4m), methoxy (MeO-/5m) and 1-(2-naphthyl)ethanol (naphthyl/6) as the substrate was selectively oxidized, and an S-isomer alcohol was obtained with a chemical yield of 50 and an optical purity of 99% e.e. or more.

(Examination of Substrate Specificity Para-Substituted Substrate of Protein Complex Derived from Young Wheat Leaves, Young Barley Leaves and Wheat Brans in Second Step)

TABLE 5

(Substrate Specificity of Para-Substituted Substrate of Protein Complex derived from Young Wheat Leaves, Young Barley Leaves and Wheat Brans in Second Step)

| Substrate | | Reaction time | Plant origin | Products | | |
|---|---|---|---|---|---|---|
| | Ar | | | Comp | OP/% e.e. | CY/% |
| 1p | 4-BrC6H4 | 35 | WB | S-1p | ≥99 | 50 |
| | 4-BrC6H4 | 16 | YWL | S-1p | ≥99 | 50 |
| | 4-BrC6H4 | 23 | YBL | S-1p | ≥99 | 50 |
| 2p | 4-ClC6H4 | 23 | YWL | S-2p | ≥99 | 50 |
| | 4-ClC6H4 | 21 | YBL | S-2p | ≥99 | 50 |
| 3p | 4-FC6H4 | 36 | YWL | S-3p | ≥99 | 50 |
| | 4-FC6H4 | 29 | YBL | S-3p | ≥99 | 50 |
| 4p | 4-MeC6H4 | 62 | WB | S-4p | ≥99 | 50 |
| | 4-MeC6H4 | 20 | YWL | S-4p | ≥99 | 50 |
| | 4-MeC6H4 | 21 | YBL | S-4p | ≥99 | 50 |
| 5p | 4-MeOC6H4 | 21 | WB | S-5p | ≥99 | 28 |
| | 4-MeOC6H4 | 16 | YWL | S-5p | ≥99 | 50 |
| | 4-MeOC6H4 | 17 | YBL | S-5p | ≥99 | 50 |

Supplement: Comp: compound, OP/% e.e.: optical purity, CY/%: chemical yield

As is apparent from the above results, a protein complex derived from young wheat leaves (YWL), young barley leaves (YBL) and wheat brans (WB) was suitably eluted from the gel and, at the same time, an R-isomer of racemic phenyl ethanols of para-substituted bromine (Br-/1p), chlorine (Cl-/2p), fluorine (F-/3p), methyl (Me-/4p), methoxy (MeO-/5p) and 1-(2-naphthyl)ethanol (naphthyl/6) as the substrate was selectively oxidized, and an S-isomer alcohol was obtained with a chemical yield of about 50 and an optical purity of 99% e.e. or more.

(Examination of Substrate Specificity of Protein Complex Derived from *Artemisia vulgaris* Indica Leaves, Wakame (Undaria), Carrot and Pumpkin in Second Step)

TABLE 6

(Substrate Specificity of Para-Substituted Substrate of Protein Complex derived from Artemisia Vulgaris Indica Leaves, Wakame (Undaria), Carrot and Pumpkin)

| | Substrate | Reaction | Plant | Products | |
|---|---|---|---|---|---|
| | Ar | time | origin | Comp | OP/% e.e. | CY/% |
| 1p | 4-BrC6H4 | 30 | P | S-1P | ≥99 | 50 |
| 2p | 4-ClC6H4 | 38 | C | S-2P | ≥99 | 41 |
| | 4-ClC6H4 | 30 | P | S-2P | ≥99 | 50 |
| 3p | 4-FC6H4 | | | 3P | Not resolved! | |
| 4p | 4-MeC6H4 | 47 | WS | S-4P | ≥99 | 21 |
| | 4-MeC6H4 | 50 | P | S-4P | ≥99 | 50 |
| 5p | 4-MeOC6H4 | 47 | WS | S-5P | ≥99 | 32 |
| | 4-MeOC6H4 | 21 | P | S-5P | ≥99 | 25 |
| 6 | 2-naphthyl | 31 | AVI | R-6 | ≥99 | 50 |

Supplement: Comp: compound, OP/% e.e.: optical purity, CY/%: chemical yield

As is apparent from the above results, a protein complex derived from *Artemisia vulgaris* indica (AVI) leaves, wakame (Undaria) (WS), carrot (C) and pumpkin (P) was suitably eluted from the gel and, at the same time, an R-isomer of racemic phenyl ethanols of para-substituted bromine (Br-/1p), chlorine (Cl-/2p), fluorine (F-/3p), methyl (Me-/4p), methoxy (MeO-/5p) and 1-(2-naphthyl)ethanol (naphthyl/6) as the substrate was selectively oxidized, and an S-isomer alcohol was obtained with a chemical yield of 20 to 50 and an optical purity of 99% e.e. or more.

EXAMPLE 4

(Examination of Substrate Specificity of Para-Substituted Substrate of Protein Complex Derived from Egg White Albumin in Second Step)

In the second step, for the purpose of measuring an activity of a protein complex produced from ovalbumin separated from egg white, egg white was separated from chicken egg and ovalbumin was separated by ammonium sulfate precipitation. After dissolving in water so that the concentration of ovalbumin becomes 0.1 to 0.5%, a spray-drying treatment was carried out, to thereby prepare an egg white albumin powder. In accordance with a usual method, 200 ml of distilled water corresponding to 10 times the equivalent weight was added to 20 g of an egg white albumin powder and 200 ml of an aqueous 3% sodium alginate solution corresponding to 1 time the equivalent weight was added, followed by stirring until uniform. The obtained egg white albumin-sodium alginate mixed solution was added dropwise in an aqueous 4.0% calcium chloride solution, to thereby obtain egg white albumin-calcium alginate gel beads. To the obtained beads, distilled water (400 ml) corresponding to 20 times the equivalent weight of the egg white albumin powder was added as the reaction solution. After shaking for 10 hours or more at a constant-temperature shaking incubation setting of 40° C. and the number of shaking of 55 rpm, a substrate conversion reaction was carried out. As the substrate, racemic phenyl ethanols wherein bromine (Br-/1), chlorine "Cl-/2), methoxy (MeO-/5) and 1-(2-naphthyl)ethanol (naphthyl/6) were substituted on the para-position was reacted. The results of the obtained reaction time, product, optical purity and chemical yield are summarized in Table 7 below.

(Examination of Position Specificity of Para-Substituted Substrate of Protein Complex Derived from Egg White Albumin in Second Step)

TABLE 7

(Substrate Specificity of Para-Substituted Substrate by Egg White Albumin in Second Step)

| | Substrate | Reaction | Plant | Products | | |
|---|---|---|---|---|---|---|
| | Ar | time | origin | Comp | OP/% e.e. | CY/% |
| 1p | 4-BrC6H4 | 24 | IOA | R-1P | 86.6 | 27 |
| 2p | 4-ClC6H4 | 24 | IOA | R-2P | 96.4 | 26 |
| 5p | 4-MeOC6H4 | 24 | IOA | R-5P | 99.8 | 26 |
| 6 | 2-naphthyl | 24 | IOA | R-6 | 85.8 | 24 |

Supplement: Comp: compound, OP/% e.e.: optical purity, CY/%: chemical yield

As is apparent from the above results, a protein complex derived from egg white albumin was suitably eluted from the gel and, at the same time, an S-isomer of racemic phenyl ethanols of substrate para-substituted bromine (Br-/1), chlorine (Cl-/2), methoxy (MeO-/5) and 1-(2-naphthyl)ethanol (naphthyl/6) was selectively oxidized, to thereby obtain an R-isomer alcohol with a chemical yield of 26% and an optical purity of 85 to 95% e.e. As is apparent from the results, an S-isomer alcohol (99% e.e.) is obtained in case of a protein complex derived from a crude protein derived from plant resource, while a reverse R-isomer alcohol (85 to 95% e.e.) is obtained in case of a protein complex derived from egg white albumin. Thus, it becomes possible to properly use both enantiomers by properly using animals and plants.

EXAMPLE 5

(Reason why Blank Shaking is Carried Out in Constant-Temperature Shaker for 10 Hours in Second Step)

FIG. 1 shows a graph showing a persistence ratio (%) of a substrate with an asymmetric oxidation activity of a protein complex derived from a green pea protein thereof when 120 ml of distilled water is added to a green pea protein-calcium alginate gel beads prepared by dissolving 4 g of a green pea protein in 40 ml of distilled water, further adding 3% sodium alginate (40 ml), followed by stirring until uniform, and adding dropwise the obtained solution in an aqueous 4.0% calcium chloride solution, and then a substrate R-1-(2-naphthyl) ethanol is added at 0 hour, 5 hours, 10 hours, 15 hours, 20 hours, 25 hours, 35 hours, 45 hours and 55 hours after initiation of blank shaking at a constant-temperature shaker temperature setting of 40° C. and the number of shaking of 55 rpm in the second step.

As is apparent from the above results, with respect to the asymmetric oxidation reaction of the protein complex derived from the green pea protein, the protein complex is eluted from the gel at 10 hours after blank shaking and, at the same time, it is suitably reacted with the substrate R-1-(2-naphthyl)ethanol.

EXAMPLE 6a (Second Step, Examination of Substrate Specificity)

FIG. 2a is a graph wherein a ratio (%) of a substrate to a product with a reaction time is monitored for the purpose of examining substrate specificity when substrates such as racemic 1-(2-naphthyl)ethanol, R-1-(2-naphthyl)ethanol and 2-acetonaphthone are added in each amount of 50 mg at 10 hours after initiation of shaking under the same conditions as in FIG. 1. As is apparent from the above results, the activity which appear at 10 hours after blank shaking does not causes oxidation of the S-isomer alcohol and allows only an R-isomer of the substrate racemic 1-(2-naphthyl)ethanol to undergo stereoselective asymmetric oxidation.

EAMPLE 6b (Second Step, Examination of Reaction Position)

FIG. 2b is a graph wherein a substrate R-1-(2-naphthyl)ethanol (50 mg, 75 mg or 100 mg) is added to an aqueous solution (120 ml) at 10 hours after blank shaking, an aqueous solution (240 ml) at 10 hours after blank shaking, an aqueous solution at 10 hours after blank shaking+distilled water (DW: 120 ml), and new beads+an aqueous solution at 10 hours (120 ml) after blank shaking, respectively, after preparing a green pea-sodium alginate under the same conditions as in FIG. 1, and then an asymmetric oxidation catalyst is monitored in the second step.

As is apparent from the above results, the protein complex, which appears at 10 hours after blank shaking, has the area where the reaction occurs, which does not exist in beads but in an aqueous solution, and suitably reacts only with an R-isomer of 1-(2-naphthyl)ethanol.

EAMPLE 6c (Second Step, Effect of Concentration of Encapsulated Gelled Calcium Chloride Exerted on Activity)

FIG. 2c is a graph wherein a green pea-sodium alginate mixed liquid is prepared under the same conditions as in FIG. 1 and added dropwise in a solution each having a different concentration of calcium chloride (5 g/L, 7.5 g/L, 10 g/L, 15 g/L, 20 g/L, 30 g/L) and, after gelling and blank shaking for 10 hours under the same conditions, a substrate R-1-(2-naphthyl)ethanol is added in the second step, and then a difference in activity intensity of the protein complex, which exerts an influence on the concentration of calcium chloride, is summarized.

As is apparent from the above results, as the concentration of calcium chloride becomes lower, formation and elution of a protein complex are efficient and asymmetric oxidation activity increases. In contrast, as the concentration of calcium chloride becomes higher, the protein complex may be hardly eluted. On the other hand, a difference in activity was scarcely recognized when the concentration of calcium chloride is 10 g/L, 15 g/L or 20 g/L.

EAMPLE 6d (Second Step, Optimization of Amount of Green Pea Protein)

FIG. 2d is a graph showing an influence of the amount (2 g, 3 g, 4 g, 5 g) of a green pea protein at the time of preparation of a green pea alginic acid gel in the second step on activity. In this case, a green pea-calcium alginate gel was prepared in the concentration of calcium chloride of 10 g/L, and an influence of a protein complex obtained at 10 hours after blank shaking exerted on a substrate R-1-(2-naphthyl)ethanol (50 mg) was shown in the drawing.

With respect to the conditions of formation and extraction of a suitable protein complex, the amount of a green pea protein is 4 g. As a result, when the amount of the green pea protein is from 2 g to 5 g, a difference in protein complex involved in activity was scarcely recognized.

EXAMPLE 7

(Second Step, Examination of Synthesis of R-1-Octen-3-Ol as Perfume)

FIG. 8 is a diagram wherein encapsulating in a green pea-calcium alginate gel was carried out under the same conditions as in FIG. 1 in the second step and the effect involved in resolution of a protein complex at 10 hours after blank shaking of a substrate racemic 1-octen-3-ol is examined.

As is apparent from the above results, with respect to the catalyst action of the protein complex, a chromatographic peak of the formed ketone is 2% or less and the chemical yield is 85% or more, and thus GC chromatogram of R-1-octen-3-ol (98.2% e.e.) shown in FIG. 8 is obtained by deracemization (continuous recycling is examined in the below-mentioned Example 12 and Table 11).

EXAMPLE 8

(Examination of Extract of Protein Complex and Suitable Concentration of Ammonium Sulfate in Third Step)

A protein complex solution (40 ml) obtained under the conditions of Example 1 was transferred in a 50 mL plastic centrifuge tube, and (1) 8.8 g of each ammonium sulfate was added, to thereby adjust to saturated 30% and, after being left to stand for 20 hours or more, (2) centrifugal separation (10,000 rpm, 15 min) was carried out and, after removing the ammonium sulfate solution through decantation, or (3) 10 ml racemic-1-(2-naphthyl)ethanol (3 ppm) dissolved in 50 mM-Tris HCl buffer (pH 8.0) was added, asymmetric oxidation activity was measured. (4) The solution fraction after decantation was further adjusted to saturated 40% by adding 3.1 g of ammonium sulfate and, after being left to stand for 20 hours or more, asymmetric oxidation activity of the precipitate obtained by centrifugal separation was determined in the same manner. The solution fraction after decantation was further adjusted to saturated 50% by adding 3.15 g of ammonium sulfate and, after still standing and further centrifugal separation, oxidation activity of the precipitate was determined in the same manner. The solution fraction after decantation was adjusted to saturated 60% by adding 3.3 g of ammonium sulfate and, after centrifugal separation and further still standing, oxidation activity was determined in the same manner. The solution fraction after decantation was adjusted to saturated 70% by adding 3.45 g of ammonium sulfate and, after centrifugal separation and further still standing, oxidation activity was determined in the same manner. The results are shown below.

TABLE 8

| (Results at 30 Hours after Reaction) (Results at 30 Hours after Reaction) | | | |
|---|---|---|---|
| | Ketone oxide | R-Alcohol | S-Alcohol |
| Saturated 30% (8.8 g) | 3.23 | 43.35 | 53.42 |
| Saturated 40% (3.1 g) | 0.36 | 47.26 | 52.38 |
| Saturated 50% (3.15 g) | 0.96 | 45.27 | 53.77 |
| Saturated 60% (3.3 g) | 0.48 | 46.90 | 52.61 |
| Saturated 70% (3.45 g) | — | 47.50 | 52.50 |

Numerical value = GC % ratio
Numerical value = GC % ratio

As is apparent from the above results, an optimum concentration of ammonium sulfate for crystallization of the protein complex of the third step is saturated 30%. It was possible to estimate that the obtained protein complex is a water-insoluble gluten-like protein and has a property changed to water solubility in the presence of calcium, and thus making it possible to precipitate under weak water solubility condition of saturated 30%.

EXAMPLE 9

(Concentration of Substrate to be Treated by Crystallized Protein Complex in Third Step)

The aqueous crystallized protein complex solution obtained under the conditions of Example 1 was transferred in a 50 mL plastic centrifuge tube, and (1) 8.8 g of each ammonium sulfate was added, to thereby adjust to saturated 30% and, after being left to stand, (2) centrifugal separation (10,000 rpm, 15 min) was carried out and, after decantation, to the crystallized protein complex obtained as a precipitate, (3) 10 mL of a racemic-1-(2-naphthyl)ethanol solution (having a concentration of 1 ppm, 2 ppm, 3 ppm, 4 ppm, 5 ppm) dissolved in 50 mM-Tris HCl buffer (pH 8.0) was added, followed by examination.

TABLE 9

(Results at 30 Hours after Reaction)
(Results at 30 Hours after Reaction)

| After 30 hours | Ketone oxide | R-Alcohol | S-Alcohol |
|---|---|---|---|
| Saturated 30%, Substrate 1 ppm | 15.16 | 14.91 | 69.93 |
| Saturated 30%, Substrate 2 ppm | 8.28 | 19.30 | 72.42 |
| Saturated 30%, Substrate 3 ppm | 14.90 | 15.58 | 69.51 |
| Saturated 30%, Substrate 4 ppm | 9.77 | 22.06 | 68.17 |
| Saturated 30%, Substrate 5 ppm | 12.53 | 21.05 | 66.42 |

Numerical value = GC % ratio
Numerical value = GC % ratio

As is apparent from the above results, the concentration of the substrate racemic 1-(2-naphthyl)ethanol, which enables oxidation of about 50 mg/50 ml centrifuge tube of the crystallized protein complex containing moisture obtained by the third step is from 1 ppm to 5 ppm/10 ml and there is no remarkable difference, and asymmetric oxidation can be carried out.

EXAMPLE 10

(Examination of Extract of Crystallized Protein Complex, Glutaraldehyde Cross-Linking Concentration of 0.1% and 1.0% in Fourth Step)

The protein complex solution (40 ml) obtained under the conditions of Example 1 was transferred in a 50 mL plastic centrifuge tube, and (1) 8.8 g of ammonium sulfate was added, to thereby adjust to saturated 30% and, after being left to stand for 20 hours or more, (2) a 25% glutaraldehyde solution was added so that the concentration becomes 0.1% (0.32 ml/40 ml) and 1.0% (1.6 ml/40 ml), respectively and, after being left to stand for 10 hours or more, (3) centrifugal separation (10.000 rpm, 15 min) was carried out, to thereby remove an ammonium sulfate-glutaraldehyde solution through decantation as the supernatant. With respect to the protein complex of the precipitate, 10 ml of racemic 1-(2-naphthyl)ethanol (in terms of the concentration of 3 ppm) dissolved in 50 mM Tris-HCl buffer (pH 8.0) was added and activity of asymmetric oxidation was confirmed.

TABLE 10

(Results at 30 Hours and 60 Hours after Reaction)

| | Ketone oxide | R-Alcohol | S-Alcohol |
|---|---|---|---|
| After 30 hours | | | |
| Saturated 30%, Substrate 3 ppm, GA concentration 0.1% | 21.75 | 8.67 | 69.55 |
| Saturated 30%, Substrate 3 ppm, GA concentration 1.0% | 4.76 | 27.02 | 68.23 |
| After 60 hours | | | |
| Saturated 30%, Substrate 3 ppm, GA concentration 0.1% | 8.95 | 0.0 | 91.05 |
| Saturated 30%, Substrate 3 ppm, GA concentration 1.0% | 4.20 | 22.36 | 78.58 |

Numerical value = GC % ratio
Numerical value = GC % ratio

As is apparent from the above results, the concentration of cross-liked GA of the crystallized protein complex of the fourth step is 0.1% or 1.0% and exhibits oxidation activity in both cases. However, R-alcohol asymmetric oxidation activity progressed more suitably when the concentration is 0.1% as compared with the case of 1.0%. It could be confirmed that the deracemization reaction is likely to occur as the concentration becomes closer to 0.1%.

EXAMPLE 11

(Examination of Continuous Recycling Involved in Protein Complex Powder in Fourth Step)

The protein complex solution (40 ml) obtained under the conditions of Example 1 was transferred to each of four 50 mL plastic centrifuge tubes, respectively, and (1) 8.8 g of each ammonium sulfate was added, to thereby adjust to saturated 30% and, after being left to stand for a whole day and night, (2) 0.32 ml/40 ml of a 25% glutaraldehyde solution was added so that the concentration becomes 0.1%, respectively, followed by being left to stand for 2 to 4 hours. The ammonium sulfate-glutaraldehyde solution as the supernatant was (3) subjected to centrifugal separation (10.000 rpm, 15 min) and removed through decantation, and the objective precipitate protein complex was further crushed after freeze-drying (FD). The protein complex powder (4) (358 mg) was dissolved in 3 ppm racemic 1-(2-naphthyl)ethanol-50 mM Tris-HCl buffer (pH 8.0. 40 mL) and then activity was measured. Continuous recycling was carried out after 9 hours and 15 hours. After centrifugal separation, the precipitate was recovered and 3 ppm racemic 1-(2-naphthyl)ethanol-50 mM Tris-HCl buffer (pH 8.0. 40 mL) was newly added and examination was carried out by this repeating operation. The results are as follows.

TABLE 11

(Results of Continuous Recycling of Protein Complex)
(Results of Continuous Recycling of Protein Complex)

| Continuous recycling | Ketone oxide | R-Alcohol | S-Alcohol |
|---|---|---|---|
| First time: 25 hours after | 42.65 | 0 | 57.35 |
| Second time: 9 hours after | 32.13 | 7.39 | 60.48 |
| Third time: 15 hours after | 38.98 | 4.97 | 56.05 |
| Fourth time: 9 hours after | 35.66 | 10.28 | 54.06 |
| Fifth time: 15 hours after | 35.04 | 9.85 | 55.11 |
| Sixth time: 9 hours after | 37.92 | 6.58 | 55.50 |
| Seventh time: 15 hours after | 46.64 | 0 | 53.36 |
| Eighth time: 9 hours after | 45.98 | 0 | 54.02 |
| Ninth time: 15 hours after | 43.10 | 3.90 | 53.00 |
| Tenth time: 9 hours after | 47.19 | 1.84 | 50.97 |
| Eleventh time: 15 hours after | 48.75 | 0 | 51.25 |
| Twelfth time: 9 hours after | 41.06 | 5.48 | 53.45 |
| Thirteenth time: 15 hours after | 44.47 | 0 | 55.53 |
| Fourteenth time: 9 hours after | 35.81 | 10.88 | 53.31 |
| Fifteenth time: 15 hours after | 36.57 | 6.18 | 57.26 |
| Nineteenth time: 9 hours after | 36.51 | 9.59 | 53.90 |

Numerical value = GC % ratio
Numerical value = GC % ratio

As is apparent from the results of confirmation of possibility of continuous recycling involved in the protein complex powder of the fourth step, asymmetric oxidation activity can be maintained at least 16 times (8 days) and recycling can be carried out.

EXAMPLE 12

(Synthesis of Perfume (R-1-Octen-3-01) Involved in Continuous Recycling of Protein Complex Powder in Fourth Step)

A trial of an asymmetric oxidation reaction was made in a 500 ml Erlenmeyer flask by adding 150 ml of 50 mM Tris-HCl (pH 8.0) buffer containing racemic 1-octen-3-ol having a concentration of 10 ppm to 5 g of a freeze-dried (FD) powder of the protein complex obtained in Example 11. After 30 hours or 60 hours, only the supernatant was recovered by centrifugal separation (10,000 rpm, 15 min) of 5 ml of the reaction solution. After extracting the substrate with diethyl-ether, GC measurement was carried out. The operation of continuous recycling leaded to an optical purity and a yield in the same manner as in Example 11. The reaction was terminated after 60 hours and the supernatant moiety obtained after centrifugal separation was extracted with diethyl ether, washed with saturated saline solution and then isolated and purified by silica gel chromatography, to thereby to obtain a chemical yield and an optical purity.

TABLE 12

(Synthesis by Continuous Recycling of Perfume (R-1-Octen-3-Ol))
(Synthesis by Continuous Recycling of Perfume (R-1-Octen-3-Ol))

| Continuous recycling | Ketone oxide | R-Alcohol | S-Alcohol | Chemical yield | Optical purity |
|---|---|---|---|---|---|
| First time: after 30 hours | 1.43 | 72.11 | 26.35 | | |
| After 60 hours | 3.79 | 96.21 | 0 | 88.3% | ≥98.13% ee |
| Second time: after 30 hours | 1.79 | 74.88 | 23.38 | | |
| After 60 hours | 3.77 | 96.23 | 0 | 86.5% | ≥98.10% ee |
| Third time: after 30 hours | 1.38 | 77.33 | 21.29 | | |
| After 60 hours | 3.67 | 96.33 | 0 | 85.8% | ≥98.22% ee |
| Fourth time: after 30 hours | 1.92 | 77.1 | 20.98 | | |
| After 60 hours | 3.76 | 96.24 | 0 | 86.7% | ≥98.28% ee |

Numerical value = GC % ratio
Numerical value = GC % ratio

As is apparent from the above results, with respect to continuous synthesis of substrate racemic 1-octen-3-ol, recycling can be carried out at least 4 times and, since the yield of the formed ketone is less than 4% in any case and also the chemical yield is 85% or more, the deracemization reaction occurs. The optical purity was obtained with a high optical purity of 98% ee or more four times, and FIG. 5 shows the results of GC/FID spectrum of R-1-octen-3-ol.

As is apparent from the above results, as shown in the following reaction scheme, with respect to an aryl-based substrate including a benzene or naphthalene skeleton, 50% of the formed ketone is scarcely reduced. With respect to an alkyl-chain substrate such as 1-octen-3-ol, there occurs deracemization wherein the formed ketone is further asymmetrically reduced.

[Chemical Formula 1]

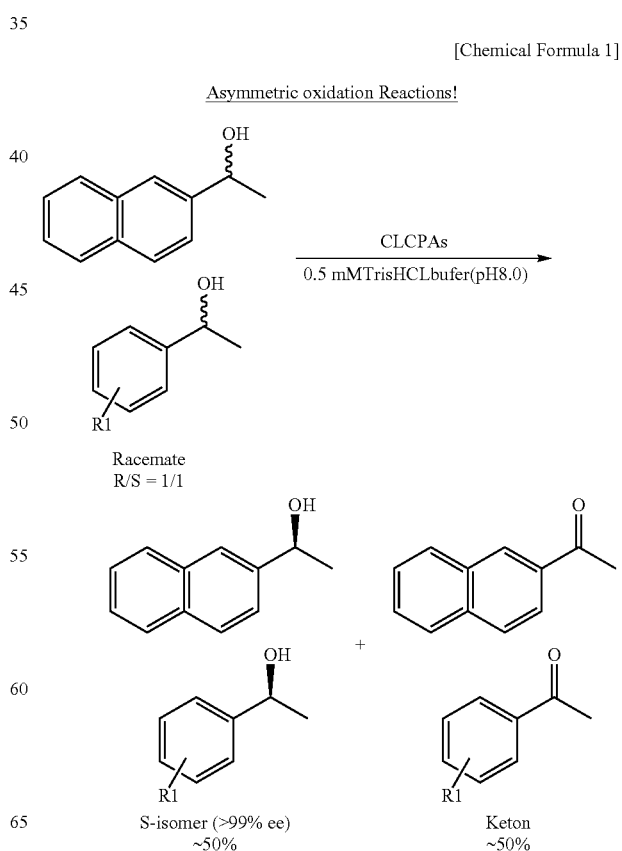

-continued
Deracemizations!

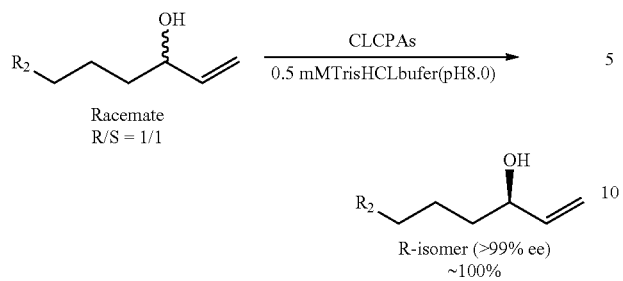

CLCPAs = Closs Linked Crude Protein Aggligats
R1 = 3-Cl, 4Cl, 3-Br, 4-Br, 3-F, 4-F, 3-Me, 4-Me, 3-MeO, 4-MeO, and 4-NO2
R2 = Alkyl chanes

EXAMPLE 13

(Determination of Molecular Weight of Protein Complex (SDS-Page))

FIG. 3 is SDS-page of a precipitate obtained by shaking a green pea-Ca alginic acid gel for 10 hours or more in warm water and then allowing the eluted protein complex to undergo crystallization precipitation at ammonium sulfate 30%. An "enzyme solution" lane shown in the drawing is an aqueous warm solution itself eluted after shaking in warm water for 10 hours or more, an "ammonium sulfate precipitate" lane is that wherein a warm water solution is allowed to undergo crystallization precipitation so as to adjust to ammonium sulfate 30% saturated, and the precipitate is redissolved by adding water, and a "supernatant" lane shows the results of SDS-page of the supernatant obtained by centrifugal separation of the ammonium sulfate precipitate.

FIG. 4 shows an extract of "FIG. 5 (Influence of the addition of table or common a salt on cross-linking efficiency by DST)" which has already been published in the description by Reiko Urade (Role of Table or Common Salt in Network Formation of Gluten Protein) of "Food and Technology", 2008 December, General remarks. The drawing shows the results obtained by ultrafugation of a solution, which is prepared by solubilizing a dough made by adding a common or table salt to a wheat flour or not using an SDS solution containing β-mercaptoethanol, and carrying out SDS-page with respect to a soluble fraction (S) and an insoluble fraction (P). The insoluble fraction is treated with sodium metaperiodate, separated by SDS polyacrylamide gel electrophoresis and thus stained with a protein.

With respect to Fig. A, since the molecular weight of a band arrangement of a fragment of an S—S bonded protein component cut by SDS of FIG. 3 agrees with SDS-page shown in FIG. 3, it could be determined that the protein complex is not composed of an enzyme, but is composed of a polymer, a low molecular glutenin, and a component similar to gliadin. Glutenin forms a disulfide bond between high-molecular and low-molecular gluten molecules by a function of air oxidation (and/or an exogenous enzyme) and thus undergoes polymerization. It is estimated that this thiol-dithiol site becomes an active domain of a redox reaction and thus causes asymmetric oxidation of a substrate racemic alcohol. It is considered that dissolved calcium not only induces formation of an intermolecular disulfide bond, but also is involved in aggregation between high-molecular and low molecular glutenin molecules (6.4 Å or less), and a property change to water solubility.

EXAMPLE 14

FIG. 5 shows qualitative analytical results of samples (i) to (vi) using Fourier transform infrared spectrophotometry (FT-IR). Analysis was carried out for the purpose of comparing a difference in molecular structure between the respective samples. Sample information of samples (i) to (vi) is as follows.

(1) Green pea protein powder: obtained by the method described in the above-mentioned Example 1
(2) Sodium alginate powder: obtained from a commercially available product
(3) Cross-linked crystallized protein complex powder produced by shaking incubator: obtained by the method described in the below-mentioned Example 15
(4) Cross-linked crystallized protein complex powder (iv) produced by jar fermentor: obtained by the method described in the below-mentioned Example 16
(5) 20 mM Ca chloride/50 mM Tris HCl buffer (pH 6.0) and (pH 8.0): obtained by the method described in Example 17

As is apparent from the results shown in FIG. 5, a difference in Fourier transform infrared spectrophotometry (FT-IR) between "samples (iii) (iv)" having an activity which catalyzes an asymmetric oxidation reaction and "samples (v) (vi)" which do not cause asymmetric oxidation reaction lie in two points, i.e. (1) absorption of a hydroxyl group (—O—Ca) of carboxylate (R—C(=O)—O—Ca) existing at 1,411 $cm^{-1}$, and (2) absorption of sugar ether (—C—O—C—) or ammonium sulfate (—O—S(=O)$_2$—O—) at 1082 $cm^{-1}$. Since strong absorption is observed in these two points for "samples (iii) (iv)" having an activity which catalyze an asymmetric oxidation reaction, it is possible to explain assumed that (1) carboxylate derived from Ca alginate (R—C(=O)—O—Ca) and sugar ether (—C—O—C—) are incorporated into samples by encapsulating, or (2) sulfur oxide was formed in case of intermolecular disulfide bonding (—S—S—). It is also considered that these two points become an important point whether or not "they have an activity which catalyzes the asymmetric oxidation reaction" and significance of encapsulating a crude protein in Ca alginate exists.

Furthermore, FIG. 6 shows qualitative analytical results of samples (i) to (iv) using an X-ray microanalyzer EPMA-1600. Sample information of samples (i) to (iv) has already been explained.

As is apparent from the results of an X-ray microanalyzer of FIG. 6, sodium (Na) is detected in "sample (i)" having an activity which catalyzes an asymmetric oxidation reaction, but sodium (Na) is not detected in "samples (ii) (iii)" having no activity which catalyzes an asymmetric oxidation reaction. Therefore, it is also estimated to be wreckage/footprint of Na alginate molecules of carboxylate (R—C(=O)—O—Na) wherein sodium (Na) derived from a green pea protein powder (iv) remains without being influenced by an action, or a sodium (Na) atom was not substituted with calcium (Ca) in the second step of adding dropwise sodium alginate in a 4% calcium chloride solution, to thereby encapsulate in calcium alginate. Since the amount of sulfur (S) of the samples (i) to (iv) is remarkably large in case of (i), there is disclosed a possibility that sulfur oxide (—O—S(=O)—O—) obtained through formation of an intermolecular disulfide bond relatively causes an asymmetric oxidation reaction.

Therefore, it was possible to estimate that absorption of oxygen ($O_2$) described in the below-mentioned Example 19 was involved in formation of an intermolecular disulfide bond (R1-S—S—R2) between cysteines (R1-S—H H—S—R2) in a green pea protein. When a sodium (Na) atom of sample (iv) is wreckage/footprint of the Na alginate molecule, there was suggested a possibility that (1) carboxylate derived from Ca alginate (R—C(=O)—O—Ca) and sugar ether (—C—O—C—) are incorporated in samples by encapsulating.

EXAMPLE 15

(Process for Producing Protein Complex Produced by Shaking Incubator Described in FIG. 5(iii) and FIG. 6(i))

In the second step, seeds were crushed and water was added and, after 1 hour, a bean curd lee fraction of a precipitate was removed and a water-soluble fraction was spray-dried to obtain a protein powder derived from green pea (PP). To 30 g of the obtained protein powder, 300 ml of distilled water corresponding to 10 times the equivalent weight was added. After sufficiently dissolving under stirring, 300 ml of an aqueous 3% sodium alginate solution corresponding to 1 time the equivalent weight was added, followed by stirring until uniform. The obtained green pea-sodium alginate mixed solution was added dropwise in an aqueous 4.0% calcium chloride solution (pH 9.16), to thereby obtain gel beads. Distilled water (500 ml) corresponding to 20 times the equivalent weight of the green pea protein powder as reaction solution was added to the obtained beads, followed by shaking at temperature setting of 40° C. and the number of shaking of 55 rpm of a constant-temperature shaking incubator for 10 hours or more.

Apparatus Used
(1) Reaction tank: A 5,000 ml Erlenmeyer flask was respectively arranged in a constant-temperature shaking incubator 3.
  Number of shaking: 55 rpm
  Temperature setting: 40° C.
Conditions of Stirring (Culturing) Operation
1. Green pea protein (30 g)-calcium alginate gel (about 600 mL)
2. Distilled water: 500 mL×3 (compriseers)×3 (days)
3. Number of extraction: 3 times/3 days (recovered once a day)

Conditions of Extracting Operation
1. An aqueous culture solution for one day 500 mL×3 (compriseers) was separated and recovered from beads.
2. Ammonium sulfate precipitate: An industrial ammonium sulfate is added so as to adjust to 30% saturated ammonium sulfate, and then left to stand for crystallization precipitation for 1 day.
3. Cross-linking: A 25% glutaraldehyde (GA) solution is added to a crystallized and precipitated solution so that the concentration becomes 0.25%, and then left to stand for 2 hours or more.
4. Centrifugal separation (washing): The precipitate is recovered at 10,000 rpm over 15 minutes and the supernatant is removed, and then distilled water is added, followed by washing impurities by repeating twice.
5. Freeze-drying (powderization): carried out by a freeze dryer (FD).
6. Asymmetric oxidation activity: A solution of racemic 1-(2-naphthyl)ethanol (40 mL) having a concentration of 10 ppm prepared by dissolving 350 mg of a freeze-dried (FD) powder in 50 mM Tris-HCl buffer (pH 8.0) was added and oxidation activity was examined.
7. Concentration of Ca (mg/g): After subjecting a powder sample after FD to an acid decomposition treatment, the amount of Ca was measured by an atomic absorption photometer (Contr. AA-300).

An example of a process for producing cross-linked crystallized protein complex using a constant-temperature shaking incubator is summarized in Table 12. Since a constant-temperature shaking incubator is equipped with a 5,000 ml Erlenmeyer flask sealed simply with an aluminum foil, respectively, a culture solution is sufficiently shaken at the number of shaking of 55 rpm and oxygen is sufficiently supplied. Polymerization was induced by a disulfide bond ((—S—S—)) through a glutenin-glutenin-cysteine residue (R1-S—H O H—S—R2) dehydration condensation reaction (→$H_2O$) and then carboxylate (R—C(=O)—O—Ca) derived from Ca alginate and sugar ether (—C—O—C—) were incorporated by encapsulating. It is considered that an active domain formed in this protein complex allows R alcohol to undergo selective asymmetric oxidation in an enzyme-like manner, and thus making it possible to obtain S-alcohol having an optical purity of 100% e.e.

TABLE 13

(Activity Intensity of Protein Complex produced by Shaking Incubator described in FIG. 5(iii) and FIG. 6(i))
(Activity Intensity of Protein Complex produced by Shaking Incubator described in FIG. 5(iii) and FIG. 6(i))

| Number of extraction | Once | Twice | Three times | Total (once + twice + three times): A |
|---|---|---|---|---|
| Shaking time (hour) | 24 | 24 | 24 | 72: A |
| Concentration of Ca in extract solution (mg/mL) | 2.59 | 0.756 | 0.346 | 3.695: A |
| Different test of three times in total (A, B, C) | | | | A / B / C |
| Yield amount after FD (%) | — | — | — | 6.4 / 20.3 / 20.6 |
| Concentration of Ca (mg/g) | — | — | — | 1.67 / 6.80 / 10.3 |

TABLE 13-continued (Activity Intensity of Protein Complex produced by Shaking Incubator described in FIG. 5(iii) and FIG. 6(i))
(Activity Intensity of Protein Complex produced by Shaking Incubator described in FIG. 5(iii) and FIG. 6(i))

| Number of extraction | Once | Twice | Three times | Total (once + twice + three times): A | | | | | |
|---|---|---|---|---|---|---|---|---|---|
| Asymmetric oxidation activity depending on reaction time | | | | 7 hr | 20 hr | 7 hr | 20 hr | 7 hr | 20 hr |
| Oxidation of R-isomer (%) | — | — | — | 3.38 | 57.16 | 16.86 | 48.50 | 6.11 | 49.8 |
| Optical purity (% e.e.) | | | | 99.8 | | 99.7 | | 99.6 | |

Note)
Concentration of Ca in extract solution (mg/mL): The concentration of Ca of a shaken solution was measured by an atomic absorption photometer.
Concentration of Ca (mg/g): The amount of Ca in a powdered sample after FD was measured by an atomic absorption photometer after an acid decomposition treatment.
Oxidation of R-isomer (%): 7 hours and 20 hours after reacting to a scale described in FIG. 9, the formed ketone (%) was determined by GC measurement and described. (Since 50% of an R-isomer of a substrate racemic alcohol is selectively oxidized into ketone, when ketone % is close to or more than 50%, an optical purity of the other S-alcohol is close to 100%)
Optical purity (% e.e.): determined from "S-alcohol (area %) – R-alcohol (area %)" of GC.

EXAMPLE 16

(Process for Producing Cross-Linked Crystallized Protein Complex Produced by 5 L Jar Fermentor described in FIG. 5(iv))

In the second step, seeds were crushed and water was added and, after 1 hour, a bean curd lee fraction of the precipitate was removed and a water-soluble fraction was spray-dried to obtain a protein powder derived from green pea protein (PP). To 50 g of the obtained protein powder, 500 ml of distilled water corresponding to 10 times the equivalent weight was added. After sufficiently dissolving under stirring, 500 ml of an aqueous 3% sodium alginate solution corresponding to 1 times the equivalent weight was added, followed by stirring until uniform. The obtained green pea-sodium alginate mixed solution (1,000 mL) was added dropwise in an aqueous 4.0% calcium chloride solution (pH 9.16), to thereby obtain gel beads. To the obtained beads, distilled water (1,000 mL) corresponding to 20 times the equivalent weight of the green pea protein powder was added as the reaction solution, followed by shaking at a temperature setting of 40° C. and number of shaking of 800 rpm of a 5 L jar fermentor manufactured by Takasaki Kagaku Co., Ltd.

Apparatus Used
(1) Reaction tank: 5 L jar fermentor manufactured by Takasaki Kagaku Co., Ltd.
Blade: two simple type bar-shaped paddler 800 rpm
Temperature: 40° C.
Oxygen supply: 0.5 mg/L
Conditions of Stirring (Culturing) Operation
4. Green pea protein (30 g)-calcium alginate gel (about 1,000 mL)
5. Distilled water: 1, 000 mL×3 (days)
6. Number of extraction: 3 times/3 days (recovered once a day)
Conditions of Extracting Operation: An aqueous culture solution for one day (1,000 mL) was separated and recovered from beads.
1. Ammonium sulfate precipitate: An industrial ammonium sulfate is added so as to adjust to 30% saturated ammonium sulfate, and then left to stand for crystallization precipitation for 1 day.
2. Cross-linking: A 25% glutaraldehyde (GA) solution is added to a crystallized and precipitated solution so that the concentration becomes 0.25%, and then left to stand for 2 hours or more.
3. Centrifugal separation (washing): The precipitate is recovered at 10,000 rpm over 15 minutes and the supernatant is removed, and then distilled water is added, followed by washing impurities by repeating twice.
4. Freeze-drying (powderization): carried out by a freeze dryer (FD).
5. Asymmetric oxidation activity: A solution of racemic-1-(2-naphthyl)ethanol (40 mL) having a concentration of 10 ppm prepared by dissolving 350 mg of a freeze-dried (FD) powder in 50 mM Tris-HCl buffer (pH 8.0) was added and oxidation activity was examined.
6. Concentration of Ca (mg/g): After subjecting a powder sample after FD to an acid decomposition treatment, the amount of Ca was measured by an atomic absorption photometer (Contr. AA-300).

As a result, as shown in Table 13, also in case of a 5 L jar fermentor, similar to the case of using a constant-temperature shaking incubator, it was considered that carboxylate (R—C(=O)—O—Ca) derived from the objective Ca alginate and sugar ether (—C—O—C—) were incorporated by encapsulating, to thereby form an active domain in a green pea protein, and a protein complex allows R alcohol to undergo selective asymmetric oxidation in an enzyme-like manner, and thus making it possible to obtain S-alcohol having an optical purity of 100% e.e.

TABLE 14

(Activity Intensity of Protein Complex by 5L Jar Fermentor described in FIG. 5(iv))
(Activity Intensity of Protein Complex by 5L Jar Fermentor described in FIG. 5(iv))

| Number of extraction | Once | Twice | Three times | Total |
|---|---|---|---|---|
| Shaking time (hour) | 24 | 24 | 24 | 72 |
| Concentration of Ca in extract solution (mg/mL) | 2.61 | 0.735 | 0.480 | 3.825 |
| Test | | | | A |
| Crude yield | 6.25 | 6.81 | 12.9 | 25.96 |
| Yield amount after FD (%) | — | — | — | 10.4% (5.174 g) |
| Concentration of Ca (mg/g) | — | — | — | 5.59 |
| Asymmetric oxidation activity depending on reaction time | | | | 7 hr   20 hr |

TABLE 14-continued (Activity Intensity of Protein Complex by 5L Jar Fermentor described in FIG. 5(iv))
(Activity Intensity of Protein Complex by 5L Jar Fermentor described in FIG. 5(iv))

| Number of extraction | Once | Twice | Three times | Total | |
|---|---|---|---|---|---|
| Oxidation of R-isomer (%) | — | — | — | 17.57 | 47.99 |
| Optical purity (% e.e.) | | | | | 99.8 |

Note)
Concentration of Ca in extract solution (mg/mL): The concentration of Ca of a shaken solution was measured by an atomic absorption photometer.
Concentration of Ca (mg/g): The amount of Ca in a powdered sample after FD was measured by an atomic absorption photometer after an acid decomposition treatment.
Oxidation of R-isomer (%): 7 hours and 20 hours after reacting to a scale described in FIG. 9, the formed ketone (%) was determined by GC measurement and described. (Since 50% of an R-isomer of a substrate racemic alcohol is selectively oxidized into ketone, when ketone % is close to or more than 50%, an optical purity of the other S-alcohol is close to 100%)
Optical purity (% e.e.): determined from "S-alcohol (area %) - R-alcohol (area %)" of GC.

EXAMPLE 17

(Process for Producing "Cross-Linked Crystallized Protein (pH 6.0 or pH 8.0)" Described in FIGS. 5(v) and 5(vi) and FIGS. 6(ii) and 6(iii))

For the purpose of confirming necessity of the second step of encapsulating in a calcium alginate gel, the second step (of encapsulating in a calcium alginate gel) was omitted and a green pea crude protein (4 g) was allowed to undergo constant-temperature shaking (55 rpm, 40° C., 24 hours) using a 2% calcium chloride/50 mM Tris HCl buffer solution/120 ml ((v) pH 6.0 or (vi) pH 8.0). After shaking, ammonium sulfate was added to a green pea protein calcium solution so as to adjust to 0% saturated and, after being left to stand for 24 hours or more (third step), the crystallized precipitate was cross-linked with 0.25% glutaraldehyde (fourth step) and the obtained cross-linked crystallized green pea crude protein was freeze-dried (FD) to form a powder.

(12) Reaction tank: A 300 ml Erlenmeyer flask was respectively arranged in a constant-temperature shaking incubator.
Number of shaking: 55 rpm
Temperature setting: 40° C.
Conditions of Stirring (Culturing) Operation
7. Green pea protein (4 g)
8. 2% calcium chloride/50 mM Tris HCl buffer (120 m)
9. Number of extraction: once/day
Conditions of Extracting Operation
1. Ammonium sulfate precipitate: Ammonium sulfate is added so as to adjust to 30% saturated ammonium sulfate after constant-temperature shaking (55 rpm, 40° C., 24 hours).
2. Cross-linking: A 25% glutaraldehyde (GA) solution is added to a crystallized and precipitated solution so that the concentration becomes 0.25%, and then left to stand for 2 hours or more.
3. Centrifugal separation (washing): The precipitate is recovered at 10,000 rpm over 15 minutes and the supernatant is removed, and then distilled water is added, followed by washing impurities by repeating twice.
4. Freeze-drying (powderization): carried out by a freeze dryer (FD).
5. Asymmetric oxidation activity: A solution of racemic-(2-naphthyl)ethanol (40 mL) having a concentration of 10 ppm prepared by dissolving 350 mg of a freeze-dried (FD) powder in 50 mM Tris-HCl buffer (pH 8.0) was added and oxidation activity was examined.
6. Concentration of Ca (mg/g): After subjecting a powder sample after FD to an acid decomposition treatment, the amount of Ca was measured by an atomic absorption photometer (Contr. AA-300).

As shown in Table 15, it could be confirmed that the second step of "encapsulating in a calcium alginate gel" is indispensable for formation of a protein complex, in addition to the concentration of dissolved Ca and dissolved oxygen which induce a glutenin-glutenin disulfide bond ((—S—S—)).

TABLE 15

(Activity Intensity of "Protein Complex (pH 6.0 or pH 8.0)" described in FIGS. 5(v) and 5(vi) and FIGS. 6(ii) and 6(iii))
(Activity Intensity of "Protein Complex (pH 6.0 or pH 8.0)" described in FIGS. 5(v) and 5(vi) and FIGS. 6(ii) and 6(iii))

| | Sample at pH 6.0 | | Sample at pH 8.0 | |
|---|---|---|---|---|
| Shaking time (hour) | 24 | | 24 | |
| Crude yield | 12.3 | | 11.8 | |
| Yield amount after FD (%) | 3.1 | | 2.9 | |
| Concentration of Ca (mg/g) | 15.1 | | 20.6 | |
| | 7 hr | 20 hr | 7 hr | 20 hr |
| Oxidation of R-isomer (%) | 3.38 | 7.79 | 7.68 | 7.44 |
| Optical purity (% e.e.) | C | | C | |

Note)
Concentration of Ca (mg/mL): The amount of Ca in a powdered sample after FD was measured by an atomic absorption photometer.
Oxidation of R-isomer (%): After 7 hours and 20 hours, the formed ketone (%) was determined by GC measurement and described.
Asymmetric oxidation Activity
C: Only an R-isomer of a racemic 1-(2-naphthyl)ethanol (10 ppm, 40 ml) solution is scarcely asymmetrically oxidized by a "protein complex" (350 mg) within 20 hours (the formed ketone is 10% or less).
B: Asymmetrically oxidation of only an R-isomer of a racemic 1-(2-naphthyl)ethanol (10 ppm, 40 ml) solution is stopped by a "protein complex" (350 mg) during asymmetric oxidation until 20 hours (the formed ketone is 30% or less).
A: Only an R-isomer of a racemic 1-(2-naphthyl)ethanol (10 ppm, 40 ml) solution is scarcely asymmetrically oxidized by a "protein complex" (350 mg) within 20 hours (the formed ketone is 40% or more).

EXAMPLE 18

(Influence of Asymmetric Oxidation Activity (Right Axis) after 6 Hours on Air Oxidation Time of Calcium Alginate Encapsulated Beads and on Protein Complex Yield in Second Step)

FIG. 7 is a graph wherein the yield and oxidation activity of a protein complex are summarized; the protein complex being obtained by producing spherical green pea protein-calcium alginate beads are in accordance with a usual method; leaving the beads left to stand in air for 0 hour, 0.5 hour, 1 hour, 3 hours, 5 hours and 7 hours; carrying out shaking extraction in warm water through constant-temperature shaking incubation (40° C., 55 rpm) using a usual process for 2 days (first time) and 1 day (second time)) in the second step; leaving a warm water extract solution to stand at saturated 30% ammonium sulfate for a whole day and night in accordance with a usual method; cross-linking at the concentration of 0.25% glutaraldehyde; freeze-drying the obtained cross-linked crystallized protein complex (CLDPs); and subjected cross-linked crystallized protein complex to ball mill crushing. With respect to the asymmetric oxidation activity, 10 ppm racemic 1-(2-naphthyl)ethanol solution/50 mM Tris-HCl buffer (pH 8.0, 40 mL) was added to 350 mg of the cross-linked crystallized protein complex and oxidation activity is exhibited at 6 hours after constant-temperature shaking incubation (40° C., 55 rpm).

As is apparent from the above results, asymmetric oxidation activity of the cross-linked crystallized protein complex became strong as the air oxidation time becomes longer. In contrast, the yield of the obtained protein complex was high after 1 hour and 3 hours. Therefore, it could be confirmed that the protein complex induces (i) an intermolecular disulfide bond (—S—S—) in a protein, (ii) intermolecular aggregation in protein (shortening of an intermolecular distance: <6.4 Å), (iii) a change of property into water solubility and the like, to thereby form an active domain (Thioredoxin fold: Cys-X-Y-Cys sequences) together with a calcium salt in gel beads in a crude protein derived from animal and plant as an inexpensive material under an oxygen atmosphere by an influence of air oxidation (and/or an exogenous enzyme), and thus a protein complex having an activity which suitably catalyzes an asymmetric oxidation reaction.

EXAMPLE 19

(Transition of pH and DO (Dissolved Oxygen Concentration) of Protein Complex in 100 L Jar Production in Second Step)

FIG. 9 is a drawing wherein the pH of distilled water (20 L) to be added when a cross-linked crystallized protein complex is produced in the second step, and DO (dissolved oxygen) are monitored; the cross-linked crystallized protein complex being obtained by crushing seeds; adding water; removing a bean curd lee fraction of the precipitate after 1 hour; spray-drying a water-soluble fraction, to thereby obtain a green pea protein powder; adding 10 L of distilled water corresponding to 10 times the equivalent weight to 1 kg of the obtained protein powder in accordance with a usual method; mixing them with stirring; adding 10 L of an aqueous 3% sodium alginate solution corresponding to 10 times the equivalent weight; stirring the solution until uniform; and adding dropwise the obtained green pea-sodium alginate mixed solution (about 20 L) in an aqueous 4.0% calcium chloride solution using a gel preparation device, to thereby form spherical beads having a diameter of about 1 to 2 mm.

Apparatus Used
(2) Reaction tank: 400φ×700H (TL-TL), vertical cylindrical tank
  Blade: 4 inclined puddles 200φ 35 rpm
  Temperature: 40° C.
(3) Crystallization tank
  420φ×460H, vertical cylindrical tank
  Blade: 6 blades turbine 120φ

A. Conditions of Stirring (Culturing) Operation
1. Green pea protein (1 kg)-calcium alginate gel (about 20 L)
2. Distilled water:
First time—stirring (20 L) for 3 days (no oxygen supply), followed by third and fourth steps
Second time—stirring (20 L) for 2 days (no oxygen supply), followed by third and fourth steps
Third time—stirring (20 L) for 1 day (oxygen supply), followed by third and fourth steps
Fourth time—stirring (20 L) for 1 day (oxygen supply), followed by third and fourth steps B. Conditions of Operation of Extracting Protein Complex
1. An aqueous culture solution (20 L) after stirring was separated and recovered from beads.
2. Ammonium sulfate precipitate: An industrial ammonium sulfate is added so as to adjust to 30% saturated ammonium sulfate, and then left to stand for 1 day for crystallization precipitation.
3. Cross-linking: A 25% glutaraldehyde (GA) solution is added to a crystallized and precipitated solution so that the concentration becomes 0.25%, and then left to stand for 2 hours or more.
4. Centrifugal separation (washing): The precipitate is recovered at 10,000 rpm over 15 minutes and the supernatant is removed, and then distilled water is added, followed by washing impurities by repeating twice.
5. Freeze-drying (powderization): carried out by a freeze dryer (FD).
6. Asymmetric oxidation activity: which represents ketone (%) obtained by oxidizing an R-isomer by adding a solution of racemic 1-(2-naphthyl)ethanol (40 mL) having a concentration of 10 ppm prepared by dissolving 350 mg of a freeze-dried (FD) powder in 50 mM Tris-HCl buffer (pH 8.0).
7. Concentration of Ca (mg/g): After subjecting a powder sample after FD to an acid decomposition treatment, the amount of Ca was measured by an atomic absorption photometer (Contr. AA-300).

As shown in FIG. 9, with respect to beads produced by adding dropwise in an aqueous 4.0% calcium chloride solution (pH 9.16), in case of stirring in distilled water without supplying oxygen, the pH transited within a weak acid range, e.g., 5.72 (first time) and 6.20 (second time) and dissolved oxygen (DO) became zero after 0.7 hour (first time) and 1 hour (second time). In case of stirring while supplying oxygen (controlled to 0.5 mg/L), the pH turned from weak acid to the weak alkali side, e.g. 7.20 (third time). The pH always transited to weak alkali at about pH 7.45 (fourth time) and DO transits within a range from about 0 to 1 mg/L in both third and fourth times.

As is apparent from the above results, high dissolved Ca ion concentration exists in the first and second times with no oxygen supply. It was examined whether or not formation of an active domain in a state where the dissolved oxygen concentration is zero (oxygen deficiency), i.e. formation of an active domain by a disulfide bond between glutenin molecules and the effect of shortening an intermolecular distance. However, activity was not recognized. Subsequently, 20 L of water was replaced in the third to fourth times and, when a given dissolved oxygen concentration was maintained by supplying airs in the presence of a low dissolved Ca ion concentration, it was examined whether or not formation of an active domain in a state where the dissolved oxygen concentration is zero (oxygen deficiency), i.e. formation of an active domain by a disulfide bond between glutenin molecules and the effect of shortening an intermolecular distance. However, while weak oxidation activity is also recognized in this case, the optical purity of the formed alcohol did not exceed 50% ee. Therefore, it could be confirmed that it becomes an important point to maintain the dissolved Ca ion concentration and given dissolved oxygen concentration in formation of an active domain formed by a disulfide bond between glutenin molecules and the effect of shortening an intermolecular distance.

(Influence of Asymmetric Oxidation Activity (Right Axis) after 6 Hours on Air Oxidation Time of 3% Calcium Alginate Encapsulated Beads and on Protein Complex Yield (Left Axis) in Second Step)

FIG. 7 is a graph wherein the yield and oxidation activity of a protein complex are summarized, the protein complex being obtained by producing spherical green pea protein-calcium alginate beads in accordance with a usual method; leaving the beads to stand in air for 0 hour, 0.5 hour, 1 hour, 3 hours, 5 hours and 7 hours; carrying out shaking extraction in warm water through constant-temperature shaking incubation (40° C., 55 rpm) using a usual process for 2 days (first time) and 1 day (ninth time); leaving a warm water extract solution to stand at saturated 30% ammonium sulfate for a whole day and night in accordance with a usual method; cross-linking at the concentration of 0.25% glutaraldehyde; freeze-drying the obtained cross-linked crystallized protein complex (CLDPs); and subjected the freeze-dried cross-linked crystallized protein complex to ball mill crushing. With respect to the asymmetric oxidation activity, 10 ppm racemic 1-(2-naphthyl)ethanol solution/50 mM Tris-HCl buffer (pH 8.0, 40 mL) was added to 350 mg of the cross-linked crystallized protein complex and oxidation activity is exhibited at 6 hours after constant-temperature shaking incubation (40° C., 55 rpm).

EXAMPLE 18a (Influence of Asymmetric Oxidation Activity (Right Axis) after 6 Hours on Air Oxidation Time of 3% Calcium Alginate Encapsulated Beads and on Protein Complex Yield (Left Axis) in Second Step)

FIG. 7 is a graph wherein the yield and oxidation activity of a protein complex are summarized; the protein complex being obtained by producing spherical green pea protein-calcium alginate beads are produced in accordance with a usual method; leaving the beads to stand in air for 0 hour, 0.5 hour, 1 hour, 3 hours, 5 hours and 7 hours; carrying out shaking extraction in warm water through constant-temperature shaking incubation (40° C., 55 rpm) using a usual process for 2 days (first time) and 1 day (ninth time); leaving a warm water extract solution to stand at saturated 30% ammonium sulfate for a whole day and night in accordance with a usual method; cross-linking at the concentration of 0.25% glutaraldehyde; freeze-drying the obtained cross-linked crystallized protein complex (CLDPs); and subjecting the freeze-dried cross-linked crystallized protein complex to ball mill crushing. With respect to the asymmetric oxidation activity, 10 ppm racemic 1-(2-naphthyl)ethanol solution/50 mM Tris-HCl buffer (pH 8.0, 40 mL) was added to 350 mg of the cross-linked crystallized protein complex and oxidation activity is exhibited at 6 hours after constant-temperature shaking incubation (40° C., 55 rpm).

As is apparent from the above results, asymmetric oxidation activity of the cross-linked crystallized protein complex became strong as the air oxidation time becomes longer. In contrast, the yield of the obtained protein complex constantly transited between about 11% to 15% when more than 1 hour has passed, and the yield focused to 12% to 13%. Therefore, it could be confirmed that that the protein complex induces (i) an intermolecular disulfide bond (—S—S—) in a protein, (ii) intermolecular aggregation in protein (shortening of an intermolecular distance: <6.4 Å), (iii) a change of property into water solubility and the like, to thereby form an active domain (Thioredoxin fold: Cys-X-Y-Cys sequences) together with a calcium salt in gel beads in a crude protein derived from animal and plant as an inexpensive material under an oxygen atmosphere by an influence of air oxidation (and/or an exogenous enzyme), and thus a protein complex having an activity which suitably catalyzes an asymmetric oxidation reaction.

EXAMPLE 20

(Influence of Asymmetric Oxidation Activity (Right Axis) after 7 Hours on Na Alginate Concentration (0.5%, 1%, 1.5%, 2%, 3%) of Calcium Alginate Encapsulated Beads and on Protein Complex Yield in Second Step)

FIG. 13 is a graph wherein the yield and oxidation activity of a protein complex are summarized; the protein complex being obtained by producing spherical green pea protein-calcium alginate beads (Na alginate concentration (0.5%, 1%, 1.5%, 2%, 3%) in accordance with a usual method; leaving the beads to stand in air for 7 hours; carrying out shaking extraction in warm water through constant-temperature shaking incubation (40° C., 55 rpm) using a usual process for 2 days (first time) and 1 day (second time); leaving a warm water extract solution to stand at saturated 30% ammonium sulfate for a whole day and night in accordance with a usual method; cross-linked at the concentration of 0.25% glutaraldehyde; freeze-drying the obtained cross-linked crystallized protein complex (CLDPs); freeze-drying the cross-linked crystallized protein complex; and subjecting the freeze-dried cross-linked crystallized protein complex to ball mill crushing. With respect to the asymmetric oxidation activity, 10 ppm racemic 1-(2-naphthyl)ethanol solution/50 mM Tris-HCl buffer (pH 8.0, 40 mL) was added to 350 mg of the cross-linked crystallized protein complex and oxidation activity is exhibited at 6 hours after constant-temperature shaking incubation (40° C., 55 rpm).

As is apparent from the above results, the yield of the obtained protein complex is the highest when the Na alginate concentration is 1.5%. Even if the concentration increases or decreases from the above value, the yield gradually decreased (0.5%<1%<1.5%>2%>3%). In contrast, oxidation activity of the protein complex slightly increased (0.5%<1%<1.5%<2%<3%) as the Na alginate concentration increased. Therefore, it became apparent that an improvement in yield can be expected by allowing a protein-calcium alginate gel produced by setting the Na alginate concentration at about 1.5% to undergo air oxidation for 5 to 7 hours or more, to thereby obtain cross-linked crystallized protein complexes (CLPCs) in accordance with a usual method.

Example 21

(Difference in Asymmetric Oxidation Rate of Protein Complex (50 mg, 75 mg, 100 mg, 200 mg, 300 mg) to Substrate Concentration (10 ppm))

FIG. 14 shows the results wherein 40 ml of 50 mM Tris-HCl (pH 8.0) buffer of racemic 1-(2-naphthyl)ethanol having a concentration of 10 ppm is added to a freeze-dried (FD) powder (50 mg, 75 mg, 100 mg, 200 mg, 300 mg) of the protein complex obtained in Example 20 in a 200 ml Erlenmeyer flask and the reaction is carried out by shaking in warm water using a constant-temperature shaking incubator (40° C., 55 rpm), and then a persistence ratio (%) of R-isomer-1-(2-naphthyl)ethanol to be asymmetrically oxidized is traced every 4 hours by GC.

As is apparent from the above results, the reaction rate increased relative to the asymmetric oxidation reaction as the addition amount of the protein complex as the catalyst increased more and more relative to the substrate concentration (10 ppm) (50 mg>75 mg>100 mg>200 mg>300 mg). Since the protein complex reaction is a dehydrogenation reaction which does not depend on a coenzyme NAD (P), unlike a conventional dehydrogenation reaction which depends on baker's yeast, cultured plant cells, and coenzyme NAD (F) of microorganism cells. Therefore, it is considered that the catalyst is a catalyst wherein not only reduction in material cost, but also reduction in reaction cost can be expected EXAMPLE 21a (Difference in Asymmetric Oxidation Rate of Substrate Concentration (10-30 ppm, 30-90 ppm, 90-110 ppm, 110-140 ppm) to Protein Complex (300 mg))

FIG. 15 shows the results wherein 40 ml of 50 mM Tris-HCl (pH 8.0) buffer of racemic 1-(2-naphthyl)ethanol having a concentration (10-140 ppm) is added to a freeze-dried (FD) powder (300 mg) of the protein complex obtained in Example 20 in a 200 ml Erlenmeyer flask and the reaction is carried out by shaking in warm water using a constant-temperature shaking incubator (40° C., 55 rpm), and then a persistence ratio (%) of R-isomer-1-(2-naphthyl)ethanol to be asymmetrically oxidized is traced every 4 hours by GC.

As is apparent from the above results, the asymmetric oxidation reaction of the substrate concentration (10 to 140 ppm) to the protein complex (300 mg) of the catalyst was classified into four patters 10-30 ppm, 30-90 ppm, 90-110 ppm and 110-140 ppm, as shown in FIG. 15. That is, it was found that the reaction time of 20 hours is required in case of the substrate concentration of 10-30 ppm, 40 hours is required in case of 30-90 ppm, 60 hours in case of 90-110 ppm, and 140 hours in case of 110-140 ppm. Therefore, it was found that the reaction time is fast as the concentration of the substrate becomes lower, and the reaction time becomes drastically low at the concentration of 110 ppm or more.

Industrial Applicability

It is possible to produce an optical isomer such as a optically active alcohol to be synthesized used in the fine chemical fields such as pharmaceuticals, perfumes and foods, at low cost in an environmentally friendly and easy manner, by using the first step of freeze-drying (FD) animal and plant resources, for example, grains such as buckwheat, amaranth, rice, wheat, barley, corn, oats, rye, foxtail millet, barnyard millet, millet, adlay and sorghum; beans such as adsuki beans, kidney beans, green peas, green beans and soy beans, and the respective plant tissue of (husks (brans, rice brans), germs (sprouts), leaves (young leaves, sprouts), stems, roots and flowers of grasses and weeds further included therein, and also the respective animal tissue of egg white derived from animal, and muscle, to thereby finely crush, and optionally dissolving in warm water, removing husks, and spray-drying a water-soluble moiety, to thereby concentrate a water-soluble protein; the second step of encapsulating the crude protein in a calcium alginate gel, to thereby allow the protein to undergo air oxidation, blank-shaking in warm water, and extracting the objective protein complex from the gel; the third step of crystallizing the protein complex using 30% saturated ammonium sulfate, to thereby form a precipitate; the fourth step of cross-linking the precipitated protein complex; and the fifth step of freeze-drying (FD) the obtained protein complex, to thereby form a powder in combination.

The invention claimed is:

1. A process for producing a cross-linked crystallized protein complex, comprising:
    a first step of concentrating a crude protein from a water-soluble moiety, the crude protein obtained from animal or plant resources;
    a second step comprising:
        encapsulating the protein in a gel;
        oxidizing the gel encapsulated protein by leaving the gel to stand in the air,
    wherein the oxidation forms a protein complex; and
        extracting the protein complex from the gel;
    a third step of allowing the extracted protein complex to undergo crystallization and precipitation in an aqueous solution; and
    a fourth step of cross-linking the precipitated protein complex to form a cross-linked crystallized protein complex.

2. The process according to claim 1, wherein the protein complex is a protein complex containing at least protein and calcium.

3. The process according to claim 1, wherein the protein complex further comprises a saccharide.

4. The process according to claim 1, wherein the protein complex is a protein complex capable of catalyzing an asymmetric oxidation reaction.

5. The process according to claim 1, wherein the first step comprises:
    freeze-drying the animal or plant resources;
    crushing the freeze-dried animal or plant resources;
    eluting the crushed animal or plant resources with water to form an elution; and
    precipitating the elution to obtain the crude protein.

6. The process according to claim 1, wherein the first step comprises:
    freeze-drying the animal or plant resources;
    crushing the freeze-dried animal or plant resources finely;
    eluting the crushed animal or plant resources with water to form an elution; and
    spray-drying the elution to isolate the crude protein.

7. The process for producing a protein complex according to claim 1, wherein the gel in the second step is a calcium alginate gel.

8. The process according to claim 7, wherein the concentration of an aqueous calcium chloride solution for preparing the calcium alginate gel is 50 mM or more.

9. The process according to claim 7, wherein the protein complex is extracted from the gel in the second step using warm water, and wherein the amount of warm water when the calcium alginate gel is shaken in warm water in the second step is 1.5 times or less the amount of the calcium alginate gel.

10. The process according to claim 9, wherein the step of shaking in warm water is carried out using a constant-temperature shaking incubator in the second step.

11. The process according to claim 9, wherein the step of shaking in warm water is carried out using a jar fermenter.

12. The process according to claim 1, wherein the protein complex is extracted from the gel in the second step using warm water.

13. The process according to claim 1, wherein the air oxidation in the second step increases oxidation activity intensity.

14. The process according to claim 1, wherein the oxidizing comprises exposing the gel to air for 30 minutes or more.

15. The process according to claim 1, wherein the oxidizing enhances formation of the protein complex and water solubility of the complex.

16. The process according to claim 1, wherein the protein complex is not composed of an enzyme.

17. The process according to claim 1, wherein the protein complex has a property of aggregating in the presence of a trace amount of a salt, to thereby shorten an intermolecular distance in the second step.

18. The process according to claim 17, wherein the trace amount of a salt, is a salt which gives calcium ions.

19. The process according to claim 1, wherein the third step comprises providing ammonium sulfate.

20. The process according to claim 19, wherein the concentration of the ammonium sulfate is saturated 30% or less.

21. The process according to claim 1, wherein the cross-linking comprises providing glutaraldehyde (GA) and/or formaldehyde (FA).

22. The process according to claim 1, wherein the animal resource in the first step is selected from egg albumin or muscle of chickens, amphibians or fishes.

23. The process according to claim 1, wherein the protein complex contains at least one protein, the at least one protein having at least one peak in a region at about $1,085 \pm 50 \text{cm}^{-1}$ and a region of at about $1,411 \pm 50 \text{ cm}^{31\ 1}$, respectively, in FT-IR.

24. The process according to claim 1, wherein the protein complex is capable of catalyzing an asymmetric oxidation reaction.

25. The process according to claim 1, wherein the plant resource in the first step is selected from grain or bean.

26. The process according to claim 25, wherein the grains and beans comprise seed husks, germs, leaves, stems, roots or flowers.

27. The process according to claim 25, wherein the grain is selected from the group consisting of buckwheat, amaranth, rice, wheat, barley, corn, oats, rye, foxtail millet, barnyard millet, millet, adlay, and sorghum.

28. The process according to claim 25, wherein the bean is selected from the group consisting of adsuki beans, kidney beans, green peas, green beans, and soy beans.

* * * * *